(12) United States Patent
Rogulja et al.

(10) Patent No.: US 11,439,675 B2
(45) Date of Patent: Sep. 13, 2022

(54) METHOD FOR TREATING DAMAGE INDUCED BY SLEEP DEPRIVATION

(71) Applicant: PRESIDENT AND FELLOWS OF HARVARD COLLEGE, Cambridge, MA (US)

(72) Inventors: Dragana Rogulja, Brookline, MA (US); Alexandra Vaccaro, Arlington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/629,222

(22) PCT Filed: Jul. 5, 2018

(86) PCT No.: PCT/US2018/040839
§ 371 (c)(1),
(2) Date: Jan. 7, 2020

(87) PCT Pub. No.: WO2019/010254
PCT Pub. Date: Jan. 10, 2019

(65) Prior Publication Data
US 2020/0129572 A1 Apr. 30, 2020

Related U.S. Application Data

(60) Provisional application No. 62/529,627, filed on Jul. 7, 2017.

(51) Int. Cl.
*A61K 35/744* (2015.01)
*A61K 35/747* (2015.01)
(Continued)

(52) U.S. Cl.
CPC ............ *A61K 35/747* (2013.01); *A23L 33/12* (2016.08); *A23L 33/135* (2016.08); *A23L 33/15* (2016.08);
(Continued)

(58) Field of Classification Search
CPC .................................................. A61K 35/744
See application file for complete search history.

(56) References Cited

U.S. PATENT DOCUMENTS

2014/0212389 A1 7/2014 Degonda et al.
2015/0071993 A1 3/2015 Patel et al.

FOREIGN PATENT DOCUMENTS

CN 103937709 A 7/2014
CN 106539995 A * 3/2017 ............. A61K 36/11

OTHER PUBLICATIONS

Ramanathan et al., "Sleep deprivation decreases superoxide dismutase activity in rat hippocampus and brainstem," NeuroReport 13(11):1387-1390, 2002.*

(Continued)

*Primary Examiner* — Rosanne Kosson
(74) *Attorney, Agent, or Firm* — Nixon Peabody LLP; David S. Resnick; Mark J. FitzGerald

(57) ABSTRACT

Described herein are methods and compositions for the use of treating damage induced by SD. Aspects of the invention relate to administering to a subject in need thereof an agent that reduces reactive oxygen species. In some embodiments, administration of an agent that reduces reactive oxygen species repairs SD-induced damage in the gut.

8 Claims, 58 Drawing Sheets
Specification includes a Sequence Listing.

(51) Int. Cl.
    *A23L 33/12*     (2016.01)
    *A23L 33/18*     (2016.01)
    *A23L 33/175*     (2016.01)
    *A23L 33/15*     (2016.01)
    *A23L 33/135*     (2016.01)
    *A61P 25/20*     (2006.01)
    *A61K 31/05*     (2006.01)
    *A61K 31/137*     (2006.01)
    *A61K 31/355*     (2006.01)
    *A61K 31/375*     (2006.01)
    *A61K 31/385*     (2006.01)
    *A61K 31/4045*     (2006.01)
    *A61K 31/465*     (2006.01)
    *A61K 31/515*     (2006.01)
    *A61K 38/06*     (2006.01)
    *A61K 38/44*     (2006.01)
    *A61K 38/45*     (2006.01)
    *A61K 45/06*     (2006.01)

(52) U.S. Cl.
    CPC ............ *A23L 33/175* (2016.08); *A23L 33/18* (2016.08); *A61K 31/05* (2013.01); *A61K 31/137* (2013.01); *A61K 31/355* (2013.01); *A61K 31/375* (2013.01); *A61K 31/385* (2013.01); *A61K 31/4045* (2013.01); *A61K 31/465* (2013.01); *A61K 31/515* (2013.01); *A61K 38/063* (2013.01); *A61K 38/446* (2013.01); *A61K 38/45* (2013.01); *A61K 45/06* (2013.01); *A61P 25/20* (2018.01)

(56) References Cited

OTHER PUBLICATIONS

Alzoubi et al., "The neuroprotective effect of vitamin E on chronic sleep deprivation-induced memory impairment: the role of oxidative stress." Behavioural Brain Research 226(1):205-210 (2012).

Brown et al., "Aging induced endoplasmic reticulum stress alters sleep and sleep homeostasis." Neurobiology of Aging 35(6):1431-1441 (2014).

Chapot-Chartier et al., "Cell wall structure and function in lactic acid bacteria." Microbial Cell Factories 13(9):1-23 (2014).

Del Carmen et al., "Genetically engineered immunomodulatory *Streptococcus thermophilus* strains producing antioxidant enzymes exhibit enhanced anti-inflammatory activities." Applied and Environmental Microbiology 80(3):869-877 (2014).

Khanijow et al., "Sleep dysfunction and gastrointestinal diseases." Gastroenterology & Hepatology 11(12):817-825 (2015).

Penetar et al., "Amphetamine effects on recovery sleep following total sleep deprivation." Human Psychopharmacology: Clinical and Experimental 6(4):319-323 (1991).

* cited by examiner

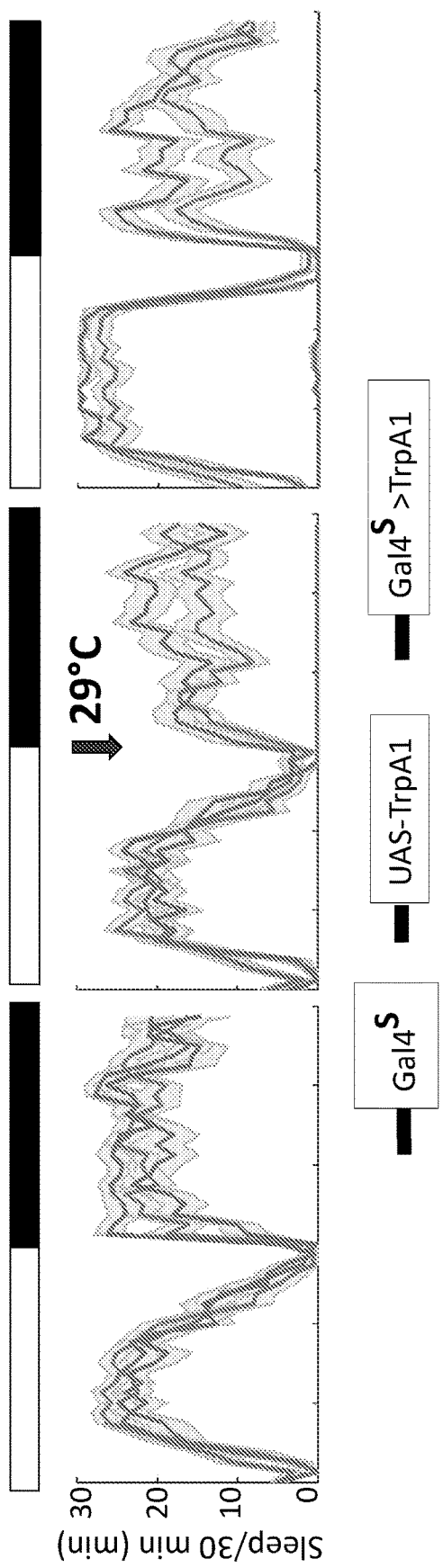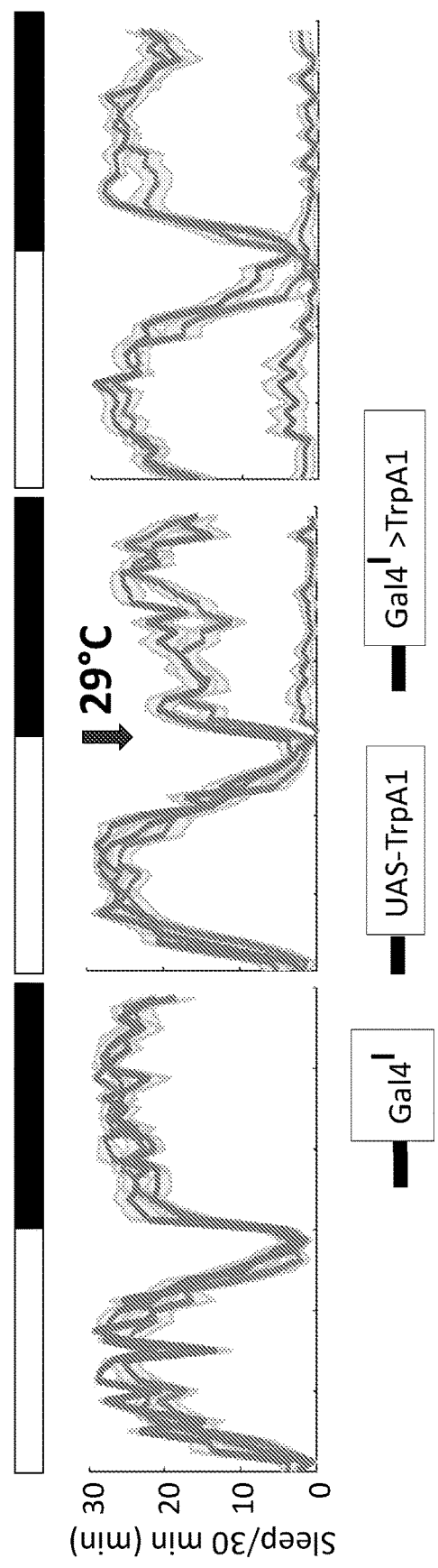

SEQUENCE LISTING

```
<160> NUMBER OF SEQ ID NOS: 8

<210> SEQ ID NO 1
<211> LENGTH: 1548
<212> TYPE: DNA
<213> ORGANISM: Lactococcus lactis

<400> SEQUENCE: 1
tttatttgag agtttgatcc tggctcagga cgaacgctgg cggcgtgcct aatacatgca      60
agttgagcgc tgaaggttgg tacttgtacc gactggatga gcagcgaacg ggtgagtaac     120
gcgtggggaa tctgcctttg agcggggggac aacatttgga aacgaatgct aataccgcat    180
aaaaacttta aacacaagtt ttaagtttga aagatgcaat tgcatcactc aaagatgatc     240
ccgcgttgta ttagctagtt ggtgaggtaa aggctcacca aggcgatgat acatagccga     300
cctgagaggg tgatcggcca cattgggact gagacacggc ccaaactcct acgggaggca     360
gcagtaggga atcttcggca atggacgaaa gtctgaccga gcaacgccgc gtgagtgaag     420
aaggttttcg gatcgtaaaa ctctgttggt agagaagaac gttggtgaga gtggaaagct     480
catcaagtga cggtaactac ccagaaaggg acggctaact acgtgccagc agccgcggta     540
```

```
atacgtaggt cccgagcgtt gtccggattt attgggcgta aagcgagcgc aggtggttta    600
ttaagtctgg tgtaaaaggc agtggctcaa ccattgtatg cattggaaac tggtagactt    660
gagtgcagga gaggagagtg gaattccatg tgtagcggtg aaatgcgtag atatatggag    720
gaacaccggt ggcgaaagcg gctctctggc ctgtaactga cactgaggct cgaaagcgtg    780
gggagcaaac aggattagat accctggtag tccacgccgt aaacgatgag tgctagatgt    840
agggagctat aagttctctg tatcgcagct aacgcaataa gcactccgcc tggggagtac    900
gaccgcaagg ttgaaactca aggaattga cgggggcccg cacaagcggt ggagcatgtg    960
gtttaattcg aagcaacgcg aagaaccta ccaggtcttg acatactcgt gctattccta   1020
gagataggaa gttccttcgg gacacgggat acaggtggtg catggttgtc gtcagctcgt   1080
gtcgtgagat gttgggttaa gtcccgcaac gagcgcaacc cctattgtta gttgccatca   1140
ttaagttggg cactctaacg agactgccgg tgataaaccg aggaaggtg gggatgacgt   1200
caaatcatca tgccccttat gacctgggct acacacgtgc tacaatggat ggtacaacga   1260
gtcgcgagac agtgatgttt agctaatctc ttaaaaccat tctcagttcg gattgtaggc   1320
tgcaactcgc ctacatgaag tcggaatcgc tagtaatcgc ggatcagcac gccgcggtga   1380
atacgttccc gggccttgta cacaccgccc gtcacaccac gggagttggg agtacccgaa   1440
gtaggttgcc taaccgcaag gagggcgctt cctaaggtaa gaccgatgac tggggtgaag   1500
tcgtaacaag gtagccgtat cggaaggtgc ggctggatca cctcctttt                1548

<210> SEQ ID NO 2
<211> LENGTH: 201
<212> TYPE: PRT
<213> ORGANISM: Streptococcus thermophilus

<400> SEQUENCE: 2

Met Ala Ile Ile Leu Pro Asp Leu Pro Tyr Ala Tyr Asp Ala Leu Glu
1               5                   10                  15

Pro Tyr Ile Asp Ala Glu Thr Met Thr Leu His His Asp Lys His His
            20                  25                  30

Ala Thr Tyr Val Ala Asn Ala Asn Ala Ala Leu Glu Lys His Pro Glu
        35                  40                  45

Ile Gly Glu Asp Leu Glu Ala Leu Leu Ala Asp Val Glu Lys Ile Pro
    50                  55                  60

Ala Asp Ile Arg Gln Ala Leu Ile Asn Asn Gly Gly His Leu Asn
65                  70                  75                  80

His Ala Leu Phe Trp Glu Leu Leu Ser Pro Glu Lys Gln Glu Pro Thr
                85                  90                  95

Ala Glu Val Ala Ala Ile Asn Glu Ala Phe Gly Ser Phe Glu Ala
            100                 105                 110

Phe Gln Glu Val Phe Thr Thr Ala Ala Thr Thr Arg Phe Gly Ser Gly
        115                 120                 125

Trp Ala Trp Leu Val Val Asn Ala Glu Gly Lys Leu Glu Val Val Ser
    130                 135                 140

Thr Pro Asn Gln Asp Thr Pro Ile Ser Asp Gly Lys Lys Pro Ile Leu
145                 150                 155                 160

Ala Leu Asp Val Trp Glu His Ala Tyr Tyr Leu Lys Tyr Arg Asn Val
                165                 170                 175

Arg Pro Asn Tyr Ile Lys Ala Phe Phe Glu Ile Ile Asn Trp Asn Lys
            180                 185                 190
```

```
Val Ala Glu Leu Tyr Ala Glu Ala Lys
        195                 200
```

<210> SEQ ID NO 3
<211> LENGTH: 205
<212> TYPE: PRT
<213> ORGANISM: Lactobacillus casei

<400> SEQUENCE: 3

```
Met Thr Phe Val Leu Pro Asp Leu Pro Phe Asp Tyr Ala Ala Leu Glu
1               5                   10                  15

Pro Tyr Ile Asp Ala Thr Thr Met His Leu His His Asp Lys His His
            20                  25                  30

Gln Thr Tyr Ile Asp Lys Leu Asn Ala Ser Leu Asp Gly Val Pro Gln
        35                  40                  45

Ala Ala Gly Lys Ser Ile Glu Gln Leu Leu Thr Gly Leu Asp Ala Leu
    50                  55                  60

Pro Glu Ser Val Arg Val Ser Val Arg Asn Asn Gly Gly His Tyr
65                  70                  75                  80

Asn His Ser Leu Phe Trp Thr Met Leu Ser Pro Glu Ser Thr Ile Lys
                85                  90                  95

Pro Asp Gly Gln Leu Leu Ala Asp Leu Glu Ser Thr Phe Asp Ser Phe
            100                 105                 110

Asp Lys Phe Lys Ala Glu Phe Ser Gln Ala Ala Leu Ser Val Phe Gly
        115                 120                 125

Ser Gly Trp Ala Trp Leu Val Lys Asp Asn Ala Thr Leu Lys Ile Val
    130                 135                 140

Thr Thr Ala Asn Gln Asp Ser Pro Ile Thr Tyr His Gln Tyr Pro Leu
145                 150                 155                 160

Leu Gly Leu Asp Val Trp Glu His Ala Tyr Tyr Leu His Tyr Gln Asn
                165                 170                 175

Arg Arg Pro Glu Tyr Val Asp Ala Phe Phe Lys Val Ile Asn Trp Gln
            180                 185                 190

Thr Val Glu Asn Arg Leu Met His Pro Asp Thr Asn Ala
        195                 200                 205
```

<210> SEQ ID NO 4
<211> LENGTH: 206
<212> TYPE: PRT
<213> ORGANISM: Lactococcus lactis

<400> SEQUENCE: 4

```
Met Ala Phe Thr Leu Pro Glu Leu Pro Tyr Ala Pro Asn Ala Leu Glu
1               5                   10                  15

Pro Phe Asp Asp Ala Thr Met Arg Leu His His Gly Lys His His
            20                  25                  30

Gln Thr Tyr Val Asn Asn Leu Asn Ala Ala Ile Glu Lys His Asn Glu
        35                  40                  45

Leu Asp Asp Leu Ser Leu Glu Glu Leu Leu Thr Asp Leu Ser Ala Ile
    50                  55                  60

Pro Glu Asp Ile Arg Thr Ala Val Arg Asn Asn Gly Gly Gly His Leu
65                  70                  75                  80

Asn His Ser Gln Phe Trp Leu Trp Leu Arg Pro Asn Thr Asp Gly Ser
                85                  90                  95

Glu Asn His Ala Asp Gly Glu Ile Gly Asp Ala Ile Ala Lys Glu Phe
            100                 105                 110
```

Gly Ser Phe Glu Thr Phe Lys Thr Glu Phe Lys Val Ala Ala Thr Gly
            115                 120                 125

Arg Phe Gly Ser Gly Trp Ala Trp Leu Val Val Asp Glu Ala Gly Lys
130                 135                 140

Leu Lys Val Val Ser Thr Ala Asn Gln Asp Asn Pro Ile Ser Glu Gly
145                 150                 155                 160

Leu Thr Pro Val Leu Gly Leu Asp Val Trp Glu His Ala Tyr Tyr Leu
                165                 170                 175

Lys Tyr His Asn Val Arg Pro Asp Tyr Ile Glu Ala Phe Phe Asn Leu
            180                 185                 190

Val Asn Trp Asp Lys Val Asn Glu Leu Tyr Ala Lys Ala Lys
        195                 200                 205

<210> SEQ ID NO 5
<211> LENGTH: 205
<212> TYPE: PRT
<213> ORGANISM: Lactobacillus paracasei

<400> SEQUENCE: 5

Met Thr Phe Val Leu Pro Asp Leu Pro Phe Asp Tyr Ala Ala Leu Glu
1               5                   10                  15

Pro Tyr Ile Asp Ala Thr Thr Met His Leu His Asp Lys His His
            20                  25                  30

Gln Thr Tyr Ile Asp Lys Leu Asn Ala Ser Leu Asp Gly Val Pro Gln
        35                  40                  45

Ala Ala Gly Lys Ser Ile Glu Gln Leu Leu Thr Gly Leu Asp Ala Leu
    50                  55                  60

Pro Glu Ser Val Arg Val Ser Val Arg Asn Asn Gly Gly His Tyr
65                  70                  75                  80

Asn His Ser Leu Phe Trp Thr Met Leu Ser Pro Glu Ser Thr Ile Lys
                85                  90                  95

Pro Asp Gly Gln Leu Leu Ala Asp Leu Glu Ser Thr Phe Asp Ser Phe
            100                 105                 110

Asp Lys Phe Lys Ala Glu Phe Ser Gln Ala Ala Leu Ser Val Phe Gly
        115                 120                 125

Ser Gly Trp Ala Trp Leu Val Lys Asp Asn Ala Thr Leu Lys Ile Val
    130                 135                 140

Thr Thr Ala Asn Gln Asp Ser Pro Ile Thr Tyr His Gln Tyr Pro Leu
145                 150                 155                 160

Leu Gly Leu Asp Val Trp Glu His Ala Tyr Tyr Leu His Tyr Gln Asn
                165                 170                 175

Arg Arg Pro Glu Tyr Val Asp Ala Phe Phe Lys Val Ile Asn Trp Gln
            180                 185                 190

Thr Val Glu Asn Arg Leu Met His Pro Asp Thr Asn Ala
        195                 200                 205

<210> SEQ ID NO 6
<211> LENGTH: 1509
<212> TYPE: DNA
<213> ORGANISM: Streptococcus thermophilus

<400> SEQUENCE: 6
agagtttgat cctggctcag gacgaacgct ggcggcgtgc ctaatacatg caagtagaac      60
gctgaagaga ggagcttgct cttcttggat gagttgcgaa cgggtgagta acgcgtaggt     120
aacctgcctt gtagcggggg ataactattg gaaacgatag ctaataccgc ataacaatgg    180

| | |
|---|---|
| atgacacatg tcatttattt gaaaggggca attgctccac tacaagatgg acctgcgttg | 240 |
| tattagctag taggtgaggt aatggctcac ctaggcgacg atacatagcc gacctgagag | 300 |
| ggtgatcggc cacactggga ctgagacacg gcccagactc ctacgggagg cagcagtagg | 360 |
| gaatcttcgg caatggggc aaccctgacc gagcaacgcc gcgtgagtga agaaggtttt | 420 |
| cggatcgtaa agctctgttg taagtcaaga acgggtgtga gagtggaaag ttcacactgt | 480 |
| gacggtagct taccagaaag ggacggctaa ctacgtgcca gcagccgcgg taatacgtag | 540 |
| gtcccgagcg ttgtccggat ttattgggcg taaagcgagc gcaggcggtt tgataagtct | 600 |
| gaagttaaag gctgtggctc aaccatagtt cgctttggaa actgtcaaac ttgagtgcag | 660 |
| aaggggagag tggaattcca tgtgtagcgg tgaaatgcgt agatatatgg aggaacaccg | 720 |
| gtggcgaaag cggctctctg gtctgtaact gacgctgagg ctcgaaagcg tggggagcga | 780 |
| acaggattag ataccctggt agtccacgcc gtaaacgatg agtgctaggt gttggatcct | 840 |
| ttccgggatt cagtgccgca gctaacgcat taagcactcc gcctggggag tacgaccgca | 900 |
| aggttgaaac tcaaaggaat tgacggggc ccgcacaagc ggtggagcat gtggtttaat | 960 |
| tcgaagcaac gcgaagaacc ttaccaggtc ttgacatccc gatgctattt ctagagatag | 1020 |
| aaagttactt cggtacatcg gtgacaggtg gtgcatggtt gtcgtcagct cgtgtcgtga | 1080 |
| gatgttgggt taagtcccgc aacgagcgca accctattg ttagttgcca tcattcagtt | 1140 |
| gggcactcta gcgagactgc cggtaataaa ccggaggaag gtgggatga cgtcaaatca | 1200 |
| tcatgcccct tatgacctgg gctacacacg tgctacaatg gttggtacaa cgagttgcga | 1260 |
| gtcggtgacg gcgagctaat ctcttaaagc caatctcagt tcggattgta ggctgcaact | 1320 |
| cgcctacatg aagtcggaat cgctagtaat cgcggatcag cacgccgcgg tgaatacgtt | 1380 |
| cccgggcctt gtacacaccg cccgtcacac cacgagagtt tgtaacaccc gaagtcggtg | 1440 |
| aggtaacctt ttggagccag ccgcctaagg tgggacagat gattggggtg aagtcgtaac | 1500 |
| aaggtaacc | 1509 |

```
<210> SEQ ID NO 7
<211> LENGTH: 1520
<212> TYPE: DNA
<213> ORGANISM: Lactobacillus casei
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (1511)..(1511)
<223> OTHER INFORMATION: a, c, t, g, unknown or other
<220> FEATURE:
<221> NAME/KEY: modified_base
<222> LOCATION: (1516)..(1516)
<223> OTHER INFORMATION: a, c, t, g, unknown or other
<220> FEATURE:
<221> NAME/KEY: modified_base
<222> LOCATION: (1518)..(1518)
<223> OTHER INFORMATION: a, c, t, g, unknown or other

<400> SEQUENCE: 7
```

| | |
|---|---|
| gatsaacgst sgcggcgtgc ctaatacatg caagtcgaac gagttctcgt tgatgatcgg | 60 |
| tgcttgcacc gagattcaac atggaacgwg tgncggacgg gtgagtaaca cgtgggtaac | 120 |
| ctgcccttaa gtgggggata acatttggaa acagatgcta ataccgcata gatccaagaa | 180 |
| ccgcatggtt cttggctgaa agatggcgta agctatcgct tttggatgga cccgcggcgt | 240 |
| attagctagt tggtgaggta atggctcacc aaggcgatga tacgtagccg aactgagagg | 300 |

```
ttgatcggcc acattgggac tgagacacgg cccaaactct acgggaggca gcagtaggga      360
atcttccaca atggacgcaa gtctgatgga gcaacgccgc gtgagtgaag aaggctttcg      420
ggtcgtaaaa ctctgttgtt ggagaagaat ggtcggcaga gtaactgttg tcggcgtgac      480
ggtatccaac cagaaagcca cggctaacta cgtgccagca gccgcggtaa tacgtaggtg      540
gcaagcgtta tccggattta ttgggcgtaa agcgagcgca ggcggttttt taagtctgat      600
gtgaaagccc tcggcttaac cgaggaagcg catcggaaac tgggaaactt gagtgcagaa      660
gaggacagtg gaactccatg tgtagcggtg aaatgcgtag atatatggaa gaacaccagt      720
ggcgaaggcg gctgtctggt ctgtaactga cgctgaggct cgaaagcatg ggtagcgaac      780
aggattagat accctggtag tccatgccgt aaacgatgaa tgctaggtgt tgagggtttt      840
ccgcccttca gtgccgcagc taacgcatta agcattccgc ctggggagta cgaccgcaag      900
gttgaaactc aaaggaattg acgggggccc gcacaagcgg tggagcatgt ggtttaattc      960
gaagcaacgc gaagaacctt accaggtctt gacatctttt gatcacctga gagatcaggt     1020
ttccccttcg ggggcaaaat gacaggtggt gcatggttgt cgtcagctcg tgtcgtgaga     1080
tgttgggtta agtcccgcaa cgagcgcaac ccttatgact agttgccagc atttagttgg     1140
gcactctagt aagactgccg gtgacaaacc ggaggaaggt ggggatgacg tcaaatcatc     1200 atgccccttat gacctgggc tacacacgtg ctacaatgga tggtacaacg agttgcgaga     1260
ccgcgaggtc aagctaatct cttaaagcca ttctcagttc ggactgtagg ctgcaactcg     1320
cctacacgaa gtcggaatcg ctagtaatcg cggatcagca cgccgcggtg aatacgttcc     1380
cgggccttgt acacaccgcc cgtcacacca tgagagtttg taacacccga agccggtggc     1440 gtaaccctt tagggagcga gccgtctaag gtgggacaaa tgattagggt gaagtcgtaa     1500
caaggtagcc ntaggngnac                                                1520
```

`<210>` SEQ ID NO 8
`<211>` LENGTH: 1497
`<212>` TYPE: DNA
`<213>` ORGANISM: Lactobacillus paracasei

`<400>` SEQUENCE: 8

```
gcgtgctata catgcaagtc gaacgagttc tcgttgatga ttggtgcttg caccgagatt      60
caacatggaa cgagtggcgg acgggtgagt aacacgtggg taacctgccc ttaagtgggg     120
gataacattt ggaaacagat gctaataccg catagatcca agaaccgcat ggttcttggc     180
tgaaagatgg cgtaagctat cgcttttgga tggacccgcg gcgtattagc tagttggtga     240
ggtaacggct caccaaggcg atgatacgta gccgaactga gaggttgatc ggccacattg     300
ggactgagac acgcccaaa ctcctacggg aggcagcagt agggaatctt ccacaatgga     360
cgcaagtctg atggagcaac gccgcgtgag tgaagaaggc tttcgggtcg taaaactctg     420
ttgttggaga agaatggtcg gcagagtaac tgttgccggc gtgacggtat ccaaccagaa     480
agccacggct aactacgtgc cagcagccgc ggtaatacgt aggtggcaag cgttatccgg     540
atttattggg cgtaaagcga gcgcaggcgg ttttttaagt ctgatgtgaa agccctcggc     600
ttaaccgagg aagcgcatcg gaaactggga aacttgagtg cagaagagga cagtggaact     660
ccatgtgtag cggtgaaatg cgtagatata tggaagaaca ccagtggcga aggcggctgt     720
ctggtctgta actgacgctg aggctcgaaa gcatgggtag cgaacaggat tagatacccc     780
tggtagtcca tgccgtaaac gatgaatgct aggtgttgga gggtttccgc ccttcagtgc     840
```

-continued

```
cgcagctaac gcattaagca ttccgcctgg ggagtacgac cgcaaggttg aaactcaaag        900
gaattgacgg gggcccgcac aagcggtgga gcatgtggtt taattcgaag caacgcgaag        960
aaccttacca ggtcttgaca tcttttgatc acctgagaga tcaggtttcc ccttcggggg       1020
caaaatgaca ggtggtgcat ggttgtcgtc agctcgtgtc gtgagatgtt gggttaagtc       1080
ccgcaacgag cgcaaccctt atgactagtt gccagcattt agttgggcac tctagtaaga       1140
ctgccggtga caaaccggag gaaggtgggg atgacgtcaa atcatcatgc cccttatgac       1200
ctgggctaca cacgtgctac aatggatggt acaacgagtt gcgagaccgc gaggtcaagc       1260
taatctctta aagccattct cagttcggac tgtaggctgc aactcgccta cacgaagtcg       1320
gaatcgctag taatcgcgga tcagcacgcc gcggtgaata cgttcccggg ccttgtacac       1380
accgcccgtc acaccatgag agtttgtaac acccgaagcc ggtggcgtaa ccctttttagg      1440 gagcgagccg tctaaggtgg gacaaatgat tagggaagt cgaacaagag cgagccg          1497
```

METHOD FOR TREATING DAMAGE INDUCED BY SLEEP DEPRIVATION

CROSS-REFERENCE TO RELATED APPLICATION

This Application is a 35 U.S.C. § 371 National Phase Entry Application of International Application No. PCT/US2018/040839 filed Jul. 5, 2018, which designates the U.S. and claims benefit under 35 U.S.C. § 119(e) of the U.S. Provisional Application No. 62/529,627 filed Jul. 7, 2017, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 24, 2018, is named 002806-089380WOPT_SL.txt and is 16,245 bytes in size.

FIELD OF THE INVENTION

The field of the invention relates to methods for the treatment or prevention of sleep deprivation-induced damage.

BACKGROUND

Sleep is an essential, widespread behavior which becomes fragmented and shortened with age. This negatively affects cognitive functions like learning, remembering and decision-making, and is a major risk factor for multiple diseases. Poor sleep is not limited to the elderly though—most of us experience significant sleep problems at least occasionally. Our knowledge of the molecular basis of sleep regulation has increased in recent years, in large part due to the establishment of *Drosophila* as a model system for sleep studies. One question, however, remains completely mysterious: what goes wrong when we don't sleep enough? Research described herein addresses this question by identifying changes that occur in the body after sleep deprivation, and demonstrates ways to counter those changes to offset or ameliorate its negative effect.

SUMMARY

The methods and compositions disclosed herein are based, in part, on the discovery that damage associated with sleep deprivation (SD) is reversed following treatment with a probiotic or agent that reduces reactive oxygen species. Accordingly, aspects disclosed herein are related to a method of treating or preventing damage associated with sleep deprivation. Generally, the method comprises administering a therapeutically effective amount of a probiotic or agent that reduces reactive oxygen species to a subject in need thereof. In one embodiment, methods of treating or preventing damage due to SD as described herein include a step, prior to administering a probiotic or an agent, of selecting an individual who is or is at risk of becoming sleep-deprived. In one embodiment, the damage induced by sleep deprivation occurs in the brain, gastrointestinal tract, mouth, throat, lungs, heart, liver, gut, stomach, kidney, skin, bones, large intestine, small intestine, bladder, and muscular system. In one embodiment, the damage induced by sleep deprivation occurs in the gut.

The methods and compositions described herein are applicable to counter or prevent the effects of both chronic and acute SD. Chronic SD is characterized as a long-lasting condition, whereas acute SD occurs in a short duration with sudden onset.

In some embodiments of various aspects of the technology, the probiotic or agent that reduces reactive oxygen species can be a probiotic, a compound, a small molecule, a food additive, or an enzyme.

In one embodiment, the agent is synthetic. In another embodiment, the agent is naturally occurring.

In some embodiments of various aspects, the probiotic expresses a superoxide dismutase polypeptide. Optionally, the superoxide dismutase polypeptide is a superoxide dismutase A (SodA) polypeptide.

Exemplary probiotics that reduce reactive oxygen species include, but are not limited to *Streptococcus thermophilus, Lactobacillus casei, Lactococcus lactis*, and *Lactobacillus paracasei*.

In other embodiments of various aspects, a probiotic species has been engineered to express a superoxide dismutase polypeptide, which can include, but is not limited to a SodA polypeptide. The superoxide dismutase can be homologous or heterologous to the probiotic species, and can be, for example, overexpressed relative to expression of a superoxide dismutase naturally expressed by such probiotic.

In one embodiment of various aspects, the probiotic is sensitive to lysozyme. In such embodiments, exposure of a probiotic that expresses a superoxide dismutase to lysozyme can cause lysis of the bacterium, with release of the superoxide dismutase enzyme.

In other embodiments of various aspects, the probiotic is *Lactococcus lactis* or a probiotic with a 16S rRNA sequence comprising at least 90% sequence identity to a 16S rRNA sequence from *Lactococcus lactis*.

Exemplary compounds that reduce reactive oxygen species include, but are not limited to Tyrosol, Quercetin, N-Acetyl Cysteine (NAC), Metformin, Catechin, 4-phenylbutyrate (PBA), Melatonin, Ursodeoxycholic acid, Nordihydroguaiaretic acid (NDGA), Coenzyme Q10 (ubiquinone), Vitamin E, Vitamin C, lipoic acid, and β-carotene.

An exemplary small molecule that reduces reactive oxygen species includes, but is not limited to, Tirilazad.

In one embodiment of various aspects, the agent can be a food additive and is administered in a food product. Alternatively, such additive can be administered directly, i.e., without being administered in a food product.

Some exemplary food additives that reduce reactive oxygen species include, but are not limited to, Ascorbic acid, Sodium ascorbate, Calcium ascorbate, Fatty acid esters of ascorbic acid, Tocopherols, Alpha-tocopherol, Gamma-tocopherol, Delta-tocopherol, Propyl gallate, Octyl gallate, Dodecyl gallate, Erythorbic acid, Sodium erythorbate, Dodecyl gallate, Tertiary-butyl hydroquinone (TBHQ), Butylated hydroxyanisole (BHA), Butylated hydroxytoluene (BHT), Citric Acid, and 4-Hexylresorcinol.

Some exemplary enzymes that reduce reactive oxygen species can be superoxide dismutase, thioredoxin reductase, glutathione reductase, glutathione peroxidase, or glutathione S-transferase.

Another aspect of the invention described herein relates to the composition of a probiotic or agent that reduces reactive oxygen species, and a sedative.

Exemplary sedatives include, but are not limited to, a barbiturate, a benzodiazepine, a non-benzodiazepine hypnotic, a methoaqualone, a first generation antihistamine, an antidepressant, an antipsychotic, an herbal sedative, ethanol, an opioid, a general anesthetic, a melatonin agonist, an orexin antagonist, and a skeletal muscle relaxant, or a combination of two or more of these.

Another aspect of the technology described herein relates to a composition comprising a probiotic or agent that reduces reactive oxygen species, and a stimulant.

Exemplary stimulants include, but are not limited to an herbal stimulant, an amphetamine, a methamphetamine, cocaine, a methylxanthine, ephedrine, a cathinone, mephedrone, methylenedioxypyrovalerone, methylenedioxymethamphetamine, nicotine, propylhexedrine, and pseudoephedrine, or a combination of two or more of these.

In one embodiment of all aspects, the inhibitor of reactive oxygen species is an inhibitor of nitric oxide synthase. Exemplary inhibitors of nitric oxide synthase include L-NMMA (NG-Methyl-L-arginine, acetate salt); L-NIO (N5-(1-Iminoethyl)-L-ornithine, dihydrochloride); L-NIL (N6-(1-Iminoethyl)-lysine, hydrochloride); L-NI (L-Nitroindazole).

In some embodiments of the various aspects disclosed herein, the composition further comprises a pharmaceutically acceptable carrier.

Another aspect of the technology relates to a method for treating, preventing, or reducing the amount of damage induced by SD, the method comprising administering to an individual who is sleep deprived an agent or composition as described herein. In some embodiments, the agent or composition is administered to a mammal that is sleep deprived or at risk thereof. In one embodiment, the mammal is human. In another embodiment, the agent or composition is administered to a human that is sleep deprived or at risk thereof.

Definitions

As used herein, the term "sleep deprivation" refers to an individual getting at least 10% less sleep than recommended for their age group, and includes at least 20%, or at least 30%, or at least 40%, or at least 50%, or at least 60%, or at least 70%, or at least 80%, or at least 90% or even a greater percentage less sleep than recommended for their age group.

The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease", "reduction", or "inhibition" is used in the context of the reactive oxygen species levels or activity, it refers to a reduction in reactive oxygen species in a cell, a tissue, a cell extract, or a cell supernatant.

The terms "increased", "increase", or "activate" are all used herein to mean an increase by a statically significant amount. In some embodiments, the terms "increased", "increase", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

The terms "significantly different than," "statistically significant," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder, for example damage induced by SD. Treatment is generally "effective" if one or more symptoms or clinical markers are reduced. Alternatively, treatment is "effective" if the progression of a disease is reduced or halted. That is, "treatment" includes not just the improvement of symptoms or markers, but can also include a cessation or at least slowing of progress or worsening of symptoms that would be expected in absence of treatment. Beneficial or desired clinical results include, but are not limited to, alleviation of one or more symptom(s) of a disease or disorder, diminishment of extent of a disease or disorder, stabilized (i.e., not worsening) state of a disease or disorder, delay or slowing of progression of a disease or disorder, amelioration or palliation of the disease or disorder state, and remission (whether partial or total), whether detectable or undetectable. The term "treatment" of a disease or disorder also includes providing relief from the symptoms or side-effects of the disease (including palliative treatment).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material that maintains a drug or other agent in a form for delivery to a subject. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

The terms "administered" and "subjected" are used interchangeably in the context of treatment of a disease or disorder. Both terms refer to a subject being treated with an effective dose of pharmaceutical composition comprising a composition as described herein by methods of administration such as parenteral or systemic administration.

The term "optional" or "optionally" means that the subsequent described event, circumstance or substituent may or may not occur, and that the description includes instances where the event or circumstance occurs and instances where it does not.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of elements that do not materially affect the basic and novel or functional characteristic(s) of that embodiment of the invention.

BRIEF DESCRIPTION OF THE DRAWINGS

FIGS. 1A-1C shows thermogenetic sleep deprivation (SD) using a GAL4/UAS system to express TrpA1. A marked percent decrease in sleep is observed TrpA1 is expressed via the GAL4/UAS system. Strong SD is 100% SD; Intermediate SD is 90% SD, Mild SD is 60% SD. FIG. 1A shows thermogenetic sleep deprivation (SD) using GAL4/UAS system to express TrpA1. GAL4$^S$=strong GAL4 driver for strong SD. FIG. 1B shows thermogenetic sleep deprivation (SD) using GAL4/UAS system to express TrpA1. GAL4$^I$=intermediate GAL4 driver for intermediate SD. FIG. 1C shows thermogenetic sleep deprivation (SD) using GAL4/UAS system to express TrpA1. GAL4$^M$=mild GAL4 driver for mild SD.

FIG. 6A shows survival when expressing the indicated construct. FIG. 6B shows reactive oxygen species (D.H.E. levels) in indicated tissue. FIG. 6C show immunofluorescence imaging of reactive oxygen species (D.H.E. levels) in indicated tissues.

FIG. 7A shows survival when expressing the indicated construct. FIG. 7B shows reactive oxygen species (D.H.E. levels) in indicated tissue. FIG. 7C show immunofluorescence imaging of reactive oxygen species (D.H.E. levels) in indicated tissues.

FIG. 60A show fluorescent images of the brain, small intestine, and large intestine at the indicated time points. Samples are stained for dihydroethidium (DHE), e.g., to show reactive oxygen species levels. FIGS. 60B and 60C show immunofluorescent staining for 53BP1 (e.g., to show DNA damage), TIA1 (e.g., to show stress granules fromation), and Cleaved-caspase 3 (e.g., to show apoptotic cell death), at the indicated time points in the small intestine (FIG. 60B) or brain (FIG. 60C).

FIG. 61A shows survival when expressing the indicated construct. FIG. 61B shows reactive oxygen species (D.H.E. levels) in indicated tissue.

FIG. 62A shows that increased D.H.E. levels due to strong (100%) SD are reduced upon recovery (e.g., removal of 100% SD). FIG. 62B shows survival during strong (100%) SD (shown at 29° C.) and recovery, e.g., removal of 100% SD (shown at 21° C.).

DETAILED DESCRIPTION

Figure 1C:
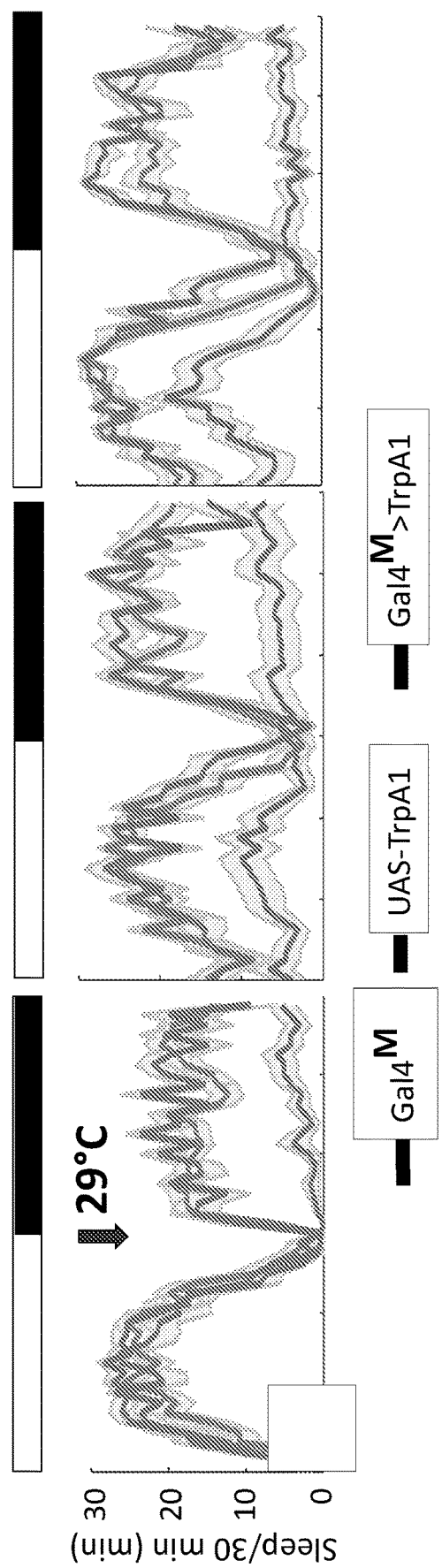

Sleep deprivation or sleep disruption can occur as a symptom of a number of disorders, as well as from the pressures and demands of life in present times. Apart from medical disorders, certain occupations and life circumstances can lead to chronic or acute SD and to the negative consequences thereof. For examples, soldiers, doctors, students, travelers and parents of newborns or babies, jet-lagged travelers, among others, frequently experience at least acute SD. As described herein, the inventors have discovered that SD induces damage in the intestinal gut, resulting in increased apoptosis of the tissue and death of an model animal. It was found that SD increased reactive oxygen species (ROS) in the affected tissue. Damage was ameliorated following the administration of an agent that reduces reactive oxygen species. Thus, reducing reactive oxygen species in a sleep deprived individual reversed damage associated with SD and can provide an effective treatment for at least some of the negative effects of SD. The following discusses the methods, compositions, and consideration necessary to practice the technology described herein.

Sleep Deprivation (SD)

SD is generally when an individual gets less sleep than needed to feel awake and alert. SD includes the absence of sleep in at least a consecutive 24 hour period, as well as a reduced amount of sleep (e.g., reduced by at least 20%, but including, for example, reduced by at least 30%, at least 40%, at least 50%, at least 60%, at least 70%, at least 80%, at least 90% or more) in at least a consecutive 24 hour period relative to that recommended for an individual in a given age and health status group. Individuals vary in the amount of sleep they require, largely depending upon age. Some, such as older adults, tend to be more resistant to the effects of sleep deprivation, while others, especially children and young adults, are more vulnerable. The National Sleep Foundation (NSF) recommendations for appropriate sleep durations for specific age groups are: newborns (0-3 months): 14-17 hours each day, infants (4-11 months): 12-15 hours, toddlers (1-2 years): 11-14 hours, preschoolers (3-5): 10-13 hours, school-age children (6-13): 9-11 hours, teenagers (14-17): 8-10 hours, adults (18-64): 7-9 hours, older adults (65+): 7-8 hours.

In some embodiments, SD is acute. Acute sleep deprivation refers to a period of seven or fewer, e.g., six or fewer, five or fewer, four or fewer, three or fewer, two or fewer consecutive 24 hour days in which an individual gets at least 20% less sleep than is recommended for an individual of their age and health status. Acute SD is frequently, but not always, associated with certain occupations or circumstances, e.g., physicians in training or on call, emergency responders or disaster workers, soldiers, travelers, and students studying for exams. Jetlag generally involves acute SD, or at least acute disturbance of the normal sleep pattern, and is contemplated as a condition that can benefit from the compositions and methods described herein.

In some embodiments, SD is chronic. Chronic sleep deprivation refers to a prolonged period of time (weeks, months, or years) without sufficient sleep or with reduced sleep (e.g., reduced by at least 10%) relative to that recommended for a subject's age group. Chronic sleep deprivation is frequently, but not necessarily, associated with medical conditions or anxiety that perturb the normal sleep pattern.

In the short term, a lack of adequate sleep can affect judgment, mood, ability to learn and retain information, and may increase the risk of serious accidents and injury. In the long term, chronic sleep deprivation may lead to a host of health problems including obesity, diabetes, cardiovascular disease, and even early mortality. SD may result in, or increase the risk for, depression, loss of memory, hallucinations, psychosis, increased blood pressure, increased stress hormone levels, seizures, headaches, weight gain or weight loss, increased risk of diabetes, and an increased risk of fibromyalgia.

Extensive tissue damage has been found in sleep deprived individuals in various organs in animal models. Cell death, cell death signaling, and cellular damage have been observed following SD. After several nights of SD, it has been observed that locus coeruleus (LC) brain cells died in a mouse model. In the liver, a strong increase in cellular damage, including DNA damage, was observed in a SD rat. In the lung and spleen of the SD rat, an increase in cell death signaling and cellular damage was observed. In the intestine, cellular damage, including DNA damage, and cell death have been observed following SD.

In various embodiments of the aspects described herein, SD-induced cellular damage and/or death occurs in various organs and/or sites within the body. Non-limiting examples of sites where SD-induced damage can occur include brain, gastrointestinal tract, mouth, throat, lungs, heart, liver, gut, stomach, kidney, skin, bones, large intestine, small intestine, bladder, and muscular system.

Reactive Oxygen Species Accumulation with SD

In some embodiments, SD-induced cellular damage is associated with an increase in reactive oxygen species (ROS). For example, it is demonstrated herein that reactive oxygen species accumulate in the intestinal gut of sleep-deprived animals, and that agents that counter reactive oxygen species are effective in preventing or reducing such accumulation and/or preventing or reducing damage caused by such accumulation.

Reactive oxygen species are reactive chemical species containing oxygen. Non-limiting examples include peroxides, superoxide, hydroxyl radical, nitric oxide, and singlet oxygen. In a biological context, reactive oxygen species are formed as a natural byproduct of the normal metabolism of oxygen and have important roles in cell signaling and homeostasis. However, during times of environmental stress (e.g., UV, heat exposure, or SD), reactive oxygen species levels can increase dramatically. This may result in damage to cell structures. When reactive oxygen species accumulate to levels at which naturally occurring antioxidants in the cell or body cannot counter them, this is known as oxidative stress.

Effects of reactive oxygen species on cell metabolism are well documented in a variety of species. These include not only roles in apoptosis (programmed cell death) but also positive effects such as the induction of host defense genes and mobilization of ion transport systems. This implicates them in control of cellular function. In particular, platelets involved in wound repair and blood homeostasis release reactive oxygen species to recruit additional platelets to sites of injury. These also provide a link to the adaptive immune system via the recruitment of leukocytes.

In general, harmful effects of reactive oxygen species on the cell most often include damage to DNA or RNA, oxidation of polyunsaturated fatty acids in lipids (lipid peroxidation), oxidation of amino acids in proteins, and oxidative deactivation of specific enzymes by oxidation of co-factors. The cytotoxic nature of reactive oxygen species is a driving force behind apoptosis, but in even higher amounts, reactive oxygen species can result in both apoptosis and necrosis, a form of uncontrolled cell death. Numerous studies have shown the pathways and associations between reactive oxygen species levels and apoptosis, but a newer line of study has connected reactive oxygen species levels and autophagy. Reactive oxygen species can also induce cell death through autophagy, which is a self-catabolic process involving sequestration of cytoplasmic contents (exhausted or damaged organelles and protein aggregates) for degradation in lysosomes. Therefore, autophagy can also regulate the cell's health in times of oxidative stress.

Reactive oxygen species can be measured by methods known to those of ordinary skill in the art. At a minimum, as necessary for the practice of the methods described herein, reactive oxygen species can be measured using the reagent dihydroethidium (DHE), which is a superoxide indicator. DHE emits a blue fluorescence in the cytosol before becoming oxidized by superoxide. Upon oxidation, DHE intercalates into a cell's DNA and emits a bright red fluorescence as an indicator of the presence or accumulation of superoxide reactive oxygen species. See, e.g., Johnson-Cadwell et al., J. Neurochem. 6: 1619-1631 (2007). Other indicators of cellular oxidative stress include, for example, the CellROX™ reagents (ThermoFisher) that emit fluorescent light indicative of cellular oxidative status at any of several different wavelengths, including "Deep Red," green and orange. Methods for staining cells using such reagents are known to those of skill in the art and/or described in product literature.

Agents that Counter Reactive Oxygen Species

Agents that counter reactive oxygen species include antioxidant agents or as well as, for example, enzymes or probiotics that express enzymes or produce products that counter reactive oxygen species.

Antioxidants are effective in countering the accumulation of reactive oxygen species. As used herein, the term "antioxidant" refers to a molecule that inhibits and/or reduces the oxidation of other molecules. Oxidation is a chemical reaction that can produce free radicals, leading to chain reactions that may damage cells. Antioxidants, for example thiols or ascorbic acid (vitamin C), terminate these chain reactions.

Probiotics are live bacteria and yeasts that provide a health benefit for their host higher organisms, e.g., humans. Probiotics are naturally found in the body, or can be administered exogenously either as a pharmaceutical preparation or as components of a food product or supplement. Many types of bacteria are classified as probiotics. Various species can have different benefits, but the most common probiotic species come from two groups, the lactic acid bacteria (e.g., Lactobacilli or Lactococci) and Bifadobacteria. Lactic acid bacteria may be the most common probiotics exogenously administered or consumed, often found in yogurt and other fermented foods. Different strains can help with diarrhea and may help those who cannot efficiently digest lactose, the sugar in milk. Bifidobacteria are also found in some fermented dairy products. They may help ease the symptoms of irritable bowel syndrome (IBS), among other conditions.

In one embodiment, probiotics useful in the methods and compositions described herein produce or secrete the enzyme superoxide dismutase (SOD). SOD is an enzyme that alternately catalyzes the dismutation (or partitioning) of the superoxide ($O_2$—) radical into either ordinary molecular oxygen ($O_2$) or hydrogen peroxide ($H_2O_2$). Superoxide is produced as a by-product of oxygen metabolism and, if not regulated, causes many types of cell damage. Thus, SOD is an important antioxidant defense in nearly all living cells exposed to oxygen. Hydrogen peroxide is also damaging and is degraded by other enzymes such as catalase, which can also provide a benefit when expressed by probiotics.

Superoxide is one of the main reactive oxygen species in the cell. As a consequence, SOD serves a key antioxidant role. Mammals and most vertebrates have three different forms of SOD, SOD1 (generally cytoplasmic), SOD2 (generally mitochondrial), and SOD3 (generally extracellular). The physiological importance of SODs is illustrated by the severe pathologies evident in mice genetically engineered to lack these enzymes. Mice lacking SOD2 die several days after birth, amid massive oxidative stress. Mice lacking SOD1 develop a wide range of pathologies, including hepatocellular carcinoma, an acceleration of age-related muscle mass loss, an earlier incidence of cataracts and a reduced lifespan. Mice lacking SOD3 do not show any obvious defects and exhibit a normal lifespan, though they are more sensitive to hyperoxic injury. Knockout mice of any SOD enzyme are more sensitive to the lethal effects of superoxide-generating compounds, such as paraquat and diquat (herbicides). Aerobic and facultative anaerobic or microaerophilic bacteria generally encode one or more SOD enzymes. To determine if a bacterial cell expresses SOD, SOD activity can be measured by one skilled in the art using the commercially available Superoxide Dismutase Activity Assay Kit (ab65354, Abcam; Cambridge, Mass.). In addition, one skilled in the art can detect levels of SOD expression using rtPCR analysis with oligonucleotides specific to the SOD coding region for the cell, e.g., bacterial cell, of interest.

In some embodiments, a probiotic as described herein expresses the SOD gene, sodA. sodA encodes the SodA protein, which functions to destroy superoxide anion radicals. One skilled in the art can use PCR-based assays with primers appropriate for the sodA gene of interest to detect the presence and/or activity of the sodA gene in a bacterial cell. Table 1 shows the NCBI references/accession numbers for sodA genes in selected bacterial strains.

TABLE 1 sodA genes from selected bacterial strains

| NCBI Reference Sequence | Bacteria | Sequence | SEQ ID NO. |
| --- | --- | --- | --- |
| WP_011680996.1 | *Streptococcus thermophilus* | maiilpdlpy aydalepyid aetmtlhhdk hhatyvanan aalekhpeig edlealladv ekipadirqa linnggghln halfwellsp ekqeptaeva aaineafgsf eafqevftta attrfgsgwa wlvvnaegkl evvstpnqdt pisdgkkpil aldvwehayy lkyrnvrpny ikaffeiinw nkvaelyaea k | SEQ ID NO.: 2 |
| WP_003595009.1 | *Lactobacillus casei* | mtfvlpdlpf dyaalepyid attmhlhhdk hhqtyidkln asldgvpqaa gksieqlltg ldalpesvrv svrnnggghy nhslfwtmls pestikpdgq lladlestfd sfdkfkaefs qaalsvfgsg wawlvkdnat lkivttanqd spityhqypl lgldvwehay ylhyqnrrpe yvdaffkvin wqtvenrlmh pdtna | SEQ ID NO.: 3 |
| AMQ26179.1 | *Lactococcus lactis* subsp. *lactis* | maftlpelpy apnalepffd datmrlhhgk hhqtyvnnln aaiekhneld dlsleelltd lsaipedirt avrnnggghl nhsqfwlwlr pntdgsenha dgeigdaiak efgsfetfkt efkvaatgrf gsgwawlvvd eagklkvvst anqdnpiseg ltpvlgldvw ehayylkyhn vrpdyieaff nlvnwdkvne lyakak | SEQ ID NO.: 4 |
| YP_807049.1 | *Lactobacillus paracasei* | mtfvlpdlpf dyaalepyid attmhlhhdk hhqtyidkln asldgvpqaa gksieqlltg ldalpesvry svrnnggghy nhslfwtmls pestikpdgq lladlestfd sfdkfkaefs qaalsvfgsg wawlvkdnat lkivttanqd spityhqypl lgldvwehay ylhyqnrrpe yvdaffkvin wqtvenrlmh pdtna | SEQ ID NO.: 5 |

Non-limiting examples of probiotics that express a sodA gene include *Streptococcus thermophilus, Lactobacillus casei, Lactococcus lactis,* and *Lactobacillus paracasei.* Strains of these species will have 16S rDNA sequence at least 90% identical, and optionally at least 91% identical, at least 92% identical, at least 93% identical, least 94% identical, at least 95% identical, at least 96% identical, least 97% identical, at least 98% identical, at least 99% identical or more, to reference 16S rDNA sequences as provided herein.

*Streptococcus thermophilus* strain DL1 16S rDNA has the following nucleotide sequence:

```
                                                          (SEQ ID NO: 6)
   1    agagtttgat cctggctcag gacgaacgct ggcggcgtgc ctaatacatg caagtagaac
  61    gctgaagaga ggagcttgct cttcttggat gagttgcgaa cgggtgagta acgcgtaggt
 121    aacctgcctt gtagcggggg ataactattg gaaacgatag ctaataccgc ataacaatgg
 181    atgacacatg tcatttattt gaaaggggca attgctccac tacaagatgg acctgcgttg
 241    tattagctag taggtgaggt aatggctcac ctaggcgacg atacatagcc gacctgagag
 301    ggtgatcggc cacactggga ctgagacacg gcccagactc ctacggggag cagcagtagg
 361    gaatcttcgg caatggggc aaccctgacc gagcaacgcc gcgtgagtga agaaggtttt
 421    cggatcgtaa agctctgttg taagtcaaga acgggtgtga gagtggaaag ttcacactgt
 481    gacggtagct taccagaaag ggacggctaa ctacgtgcca gcagccgcgg taatacgtag
 541    gtcccgagcg ttgtccggat ttattgggcg taaagcgagc gcaggcggtt tgataagtct
 601    gaagttaaag gctgtggctc aaccatagtt cgctttggaa actgtcaaac ttgagtgcag
 661    aagggagag tggaattcca tgtgtagcgg tgaaatgcgt agatatatgg aggaacaccg
 721    gtggcgaaag cggctctctg gtctgtaact gacgctgagg ctcgaaagcg tggggagcga
 781    acaggattag ataccctggt agtccacgcc gtaaacgatg agtgctaggt gttggatcct
 841    ttccgggatt cagtgccgca gctaacgcat taagcactcc gcctggggag tacgaccgca
 901    aggttgaaac tcaaaggaat tgacggggc ccgcacaagc ggtggagcat gtggtttaat
 961    tcgaagcaac gcgaagaacc ttaccaggtc ttgacatccc gatgctattt ctagagatag
1021    aaagttactt cggtacatcg gtgacaggtg gtgcatggtt gtcgtcagct cgtgtcgtga
1081    gatgttgggt taagtcccgc aacgagcgca acccctattg ttagttgcca tcattcagtt
1141    gggcactcta gcgagactgc cggtaataaa ccggaggaag gtggggatga cgtcaaatca
1201    tcatgcccct tatgacctgg gctacacacg tgctacaatg gttggtacaa cgagttgcga
1261    gtcggtgacg gcgagctaat ctcttaaagc caatctcagt tcggattgta ggctgcaact
1321    cgcctacatg aagtcggaat cgctagtaat cgcggatcag cacgccgcgg tgaatacgtt
1381    cccgggcctt gtacacaccg cccgtcacac cacgagagtt tgtaacaccc gaagtcggtg
1441    aggtaacctt ttggagccag ccgcctaagg tgggacagat gattggggtg aagtcgtaac
1501    aaggtaacc (GenBank Accession No. AB200871)
```

*Lactobacillus casei*, strain JCM1171 16S rDNA has the following nucleotide sequence:

```
                                                          (SEQ ID NO: 7)
   1    gatsaacgst sgcggcgtgc ctaatacatg caagtcgaac gagttctcgt tgatgatcgg
  61    tgcttgcacc gagattcaac atggaacgwg tgncggacgg gtgagtaaca cgtgggtaac
 121    ctgcccttaa gtgggggata acatttggaa acagatgcta ataccgcata gatccaagaa
 181    ccgcatggtt cttggctgaa agatggcgta agctatcgct tttggatgga cccgcggcgt
 241    attagctagt tggtgaggta atggctcacc aaggcgatga tacgtagccg aactgagagg
 301    ttgatcggcc acattgggac tgagacacgg cccaaactct acgggaggca gcagtaggga
 361    atcttccaca atggacgcaa gtctgatgga gcaacgccgc gtgagtgaag aaggctttcg
```

-continued

```
 421   ggtcgtaaaa ctctgttgtt ggagaagaat ggtcggcaga gtaactgttg tcggcgtgac
 481   ggtatccaac cagaaagcca cggctaacta cgtgccagca gccgcggtaa tacgtaggtg
 541   gcaagcgtta tccggattta ttgggcgtaa agcgagcgca ggcggttttt taagtctgat
 601   gtgaaagccc tcggcttaac cgaggaagcg catcggaaac tgggaaactt gagtgcagaa
 661   gaggacagtg gaactccatg tgtagcggtg aaatgcgtag atatatggaa gaacaccagt
 721   ggcgaaggcg gctgtctggt ctgtaactga cgctgaggct cgaaagcatg ggtagcgaac
 781   aggattagat accctggtag tccatgccgt aaacgatgaa tgctaggtgt tggagggttt
 841   ccgcccttca gtgccgcagc taacgcatta agcattccgc ctggggagta cgaccgcaag
 901   gttgaaactc aaaggaattg acgggggccc gcacaagcgg tggagcatgt ggtttaattc
 961   gaagcaacgc gaagaacctt accaggtctt gacatctttt gatcacctga gagatcaggt
1021   ttccccttcg ggggcaaaat gacaggtggt gcatggttgt cgtcagctcg tgtcgtgaga
1081   tgttgggtta agtcccgcaa cgagcgcaac ccttatgact agttgccagc atttagttgg
1141   gcactctagt aagactgccg gtgacaaacc ggaggaaggt ggggatgacg tcaaatcatc
1201   atgccccctta tgacctgggc tacacacgtg ctacaatgga tggtacaacg agttgcgaga
1261   ccgcgaggtc aagctaatct cttaaagcca ttctcagttc ggactgtagg ctgcaactcg
1321   cctacacgaa gtcggaatcg ctagtaatcg cggatcagca cgccgcggtg aatacgttcc
1381   cgggccttgt acacaccgcc cgtcacacca tgagagtttg taacacccga agccggtggc
1441   gtaaccctttt tagggagcga gccgtctaag gtgggacaaa tgattagggt gaagtcgtaa
1501   caaggtagcc ntaggngnac (GenBank Accession No. D16550)
```

*L. lactis* subsp. *lactis* 11403 16S rDNA has the following nucleotide sequence:

(SEQ ID NO: 1)
```
   1   tttatttgag agtttgatcc tggctcagga cgaacgctgg cggcgtgcct aatacatgca
  61   agttgagcgc tgaaggttgg tacttgtacc gactggatga gcagcgaacg ggtgagtaac
 121   gcgtggggaa tctgcctttg agcgggggac aacatttgga aacgaatgct aataccgcat
 181   aaaaacttta aacacaagtt ttaagtttga aagatgcaat tgcatcactc aaagatgatc
 241   ccgcgttgta ttagctagtt ggtgaggtaa aggctcacca aggcgatgat acatagccga
 301   cctgagaggg tgatcggcca cattgggact gagacacggc ccaaactcct acgggaggca
 361   gcagtaggga atcttcggca atggacgaaa gtctgaccga gcaacgccgc gtgagtgaag
 421   aaggttttcg gatcgtaaaa ctctgttggt agagaagaac gttggtgaga gtggaaagct
 481   catcaagtga cggtaactac ccagaaaggg acggctaact acgtgccagc agccgcggta
 541   atacgtaggt cccgagcgtt gtccggattt attgggcgta aagcgagcgc aggtggttta
 601   ttaagtctgg tgtaaaaggc agtggctcaa ccattgtatg cattggaaac tggtagactt
 661   gagtgcagga gaggagagtg gaattccatg tgtagcggtg aaatgcgtag atatatggag
 721   gaacaccggt ggcgaaagcg gctctctggc ctgtaactga cactgaggct cgaaagcgtg
 781   gggagcaaac aggattagat accctggtag tccacgccgt aaacgatgag tgctagatgt
 841   agggagctat aagttctctg tatcgcagct aacgcaataa gcactccgcc tggggagtac
 901   gaccgcaagg ttgaaactca aaggaattga cggggcccg cacaagcggt ggagcatgtg
 961   gtttaattcg aagcaacgcg aagaaccta ccaggtcttg acatactcgt gctattccta
1021   gagataggaa gttccttcgg gacacgggat acaggtggtg catggttgtc gtcagctcgt
```

-continued

```
1081   gtcgtgagat gttgggttaa gtcccgcaac gagcgcaacc cctattgtta gttgccatca
1141   ttaagttggg cactctaacg agactgccgg tgataaaccg gaggaaggtg gggatgacgt
1201   caaatcatca tgcccttat gacctgggct acacacgtgc tacaatggat ggtacaacga
1261   gtcgcgagac agtgatgttt agctaatctc ttaaaaccat tctcagttcg gattgtaggc
1321   tgcaactcgc ctacatgaag tcggaatcgc tagtaatcgc ggatcagcac gccgcggtga
1381   atacgttccc gggccttgta cacaccgccc gtcacaccac gggagttggg agtacccgaa
1441   gtaggttgcc taaccgcaag gagggcgctt cctaaggtaa gaccgatgac tggggtgaag
1501   tcgtaacaag gtagccgtat cggaaggtgc ggctggatca cctccttt
                                                                15
```

*Lactobacillus paracasei* strain 10C 16S rDNA has the following nucleotide sequence:

(SEQ ID NO: 8)
```
   1   gcgtgctata catgcaagtc gaacgagttc tcgttgatga ttggtgcttg caccgagatt
  61   caacatggaa cgagtggcgg acgggtgagt aacacgtggg taacctgccc ttaagtgggg
 121   gataacattt ggaaacagat gctaataccg catagatcca agaaccgcat ggttcttggc
 181   tgaaagatgg cgtaagctat cgcttttgga tggacccgcg gcgtattagc tagttggtga
 241   ggtaacggct caccaaggcg atgatacgta gccgaactga gaggttgatc ggccacattg
 301   ggactgagac acggcccaaa ctcctacggg aggcagcagt agggaatctt ccacaatgga
 361   cgcaagtctg atggagcaac gccgcgtgag tgaagaaggc tttcgggtcg taaaactctg
 421   ttgttggaga agaatggtcg gcagagtaac tgttgccggc gtgacggtat ccaaccagaa
 481   agccacggct aactacgtgc cagcagccgc ggtaatacgt aggtggcaag cgttatccgg
 541   atttattggg cgtaaagcga gcgcaggcgg ttttttaagt ctgatgtgaa agccctcggc
 601   ttaaccgagg aagcgcatcg gaaactggga aacttgagtg cagaagagga cagtggaact
 661   ccatgtgtag cggtgaaatg cgtagatata tggaagaaca ccagtggcga aggcggctgt
 721   ctggtctgta actgacgctg aggctcgaaa gcatgggtag cgaacaggat tagataccc
 781   tggtagtcca tgccgtaaac gatgaatgct aggtgttgga gggtttccgc ccttcagtgc
 841   cgcagctaac gcattaagca ttccgcctgg ggagtacgac cgcaaggttg aaactcaaag
 901   gaattgacgg gggcccgcac aagcggtgga gcatgtggtt taattcgaag caacgcgaag
 961   aaccttacca ggtcttgaca tcttttgatc acctgagaga tcaggtttcc ccttcggggg
1021   caaaatgaca ggtggtgcat ggttgtcgtc agctcgtgtc gtgagatgtt gggttaagtc
1081   ccgcaacgag cgcaacccct atgactagtt gccagcattt agttgggcac tctagtaaga
1141   ctgccggtga caaccggag gaaggtgggg atgacgtcaa atcatcatgc ccttatgac
1201   ctgggctaca cacgtgctac aatggatggt acaacgagtt gcgagaccgc gaggtcaagc
1261   taatctctta aagccattct cagttcggac tgtaggctgc aactcgccta cacgaagtcg
1321   gaatcgctag taatcgcgga tcagcacgcc gcggtgaata cgttcccggg ccttgtacac
1381   accgccgtc acaccatgag agtttgtaac acccgaagcc ggtggcgtaa ccctttagg
1441   gagcgagccg tctaaggtgg gacaaatgat taggggaagt cgaacaagag cgagccg
```
(GenBank Accession No. AY773956)

In one embodiment, a probiotic that does not endogenously express the sodA gene can be engineered to express a SodA polypeptide. In one embodiment, the engineered bacterial cell secretes sodA. In another embodiment, the engineered bacterial cell is sensitive to lysozymes, wherein contact between the bacterial cell and the lysozyme results in the bacterial cell lysing, or opening up, allowing for the release of sodA. Nucleic acids encoding SodA can be included on a vector, such as a bacteriophage, plasmid, or other vector. Vectors capable of directing the expression of genes and/or nucleic acid sequence to which they are operatively linked are referred to herein as "expression vectors." In general, expression vectors useful in the methods and compositions described herein are often in the form of plasmids, circular double stranded DNA molecules which, in their vector form are not part of the bacterial chromosome.

Expression vectors can be maintained extrachromosomally relative to the bacterial chromosome, or, alternatively can be integrated in the bacterial chromosome, e.g., via lysogeny. In some embodiments, the nucleic acid sequence or sequences encoding a sodA polypeptide integrates into the chromosomal DNA of a bacterial cell along with components of the vector sequence. In other embodiments, the nucleic acid sequence encoding a sodA polypeptide directly integrates into chromosomal DNA of a bacteria cell, in the absence of any components of the vector by which it was introduced. The number of copies of a sodA polypeptide that integrate into the chromosomal DNA of a bacterial cell can impact the bacterial cell, and thus it is preferred, in some embodiments, that only one copy is integrated per bacterial cell.

Inducible and non-inducible expression vectors can also be used. Other forms of expression vectors known by those skilled in the art which serve the equivalent functions can also be used.

Another type of vector is an episomal vector, i.e., a nucleic acid capable of extra-chromosomal replication. Such plasmids or vectors can include plasmid sequences from bacteria, viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. A vector can be a plasmid, bacteriophage or bacterial artificial chromosome (BAC). A vector can be a single or double-stranded DNA, RNA, or phage vector. In some embodiments, sequence encoding a sodA polypeptide is introduced into a cellular system using a BAC vector.

In certain embodiments, the nucleic acid encoding a sodA polypeptide can be encoded on a vector for CRISPR/Cas mediated integration of the nucleic acid(s) into the genome of a bacteria cell. For example, in regard to using sequences associated with CRISPR, one of skill in the art can insert a short DNA fragment containing the DNA binding domain target site into a guide RNA expression plasmid. The sgRNA expression plasmid contains the DNA binding domain target site (about 20 nucleotides), a form of the tracrRNA sequence (the scaffold) as well as a suitable promoter and necessary elements for proper processing in prokaryotic cells. Such vectors are commercially available (see, for example, Addgene). Many of the systems rely on custom, complementary oligos that are annealed to form a double stranded DNA and then cloned into the sgRNA expression plasmid. In some embodiments, co-expression of the sgRNA and the appropriate Cas enzyme or domain thereof can be achieved using the same or separate plasmids in transfected bacteria cells.

*Lactococcus lactis* (*L. lactis*) is a Gram-positive bacterium used extensively in the production of buttermilk and cheese, but is also noted for having been modified to express IL-10 for the clinical treatment of Crohn's disease (see, e.g., Breat, et al., Clin. Gastroenterol Hepatol. 4:754-759 (2006)). *L. lactis* cells are cocci that group in pairs and short chains, and, depending on growth conditions, appear ovoid with a typical length of 0.5-1.5 μm. *L. lactis* is nonsporulating and nonmotile. They have a homofermentative metabolism, which produces lactic acid from sugars. Based on its history in food fermentation, *L. lactis* has generally recognized as safe (GRAS) status, with few case reports of being an opportunistic pathogen. *L. lactis* is one of the best characterized low G+C Gram positive bacteria for which there is detailed knowledge on genetics, metabolism and biodiversity.

*L. lactis* is mainly isolated from either the dairy environment or plant material. Dairy isolates are thought to have evolved from plant isolates through a process in which genes without benefit for growth in the rich medium, milk, were either lost or down-regulated.

In some embodiments, the probiotic disclosed herein is *Streptococcus thermophilus*, or a species containing 16S rDNA with at least 90% sequence identity to *Streptococcus thermophilus* strain DL1 16S rDNA (SEQ ID NO: 6). In other embodiments, the probiotic comprises a 16S rDNA sequence at least 91%, 92%, 93%, 94%, 95%, 96%, 97%, 98%, or 99% or more identical to the SEQ ID NO:6 16S rDNA sequence from *Streptococcus thermophilus* strain DL1 16S rDNA.

In some embodiments, the probiotic disclosed herein is *L. lactis*, or a species containing 16s rDNA with at least 90% sequence identity to *L. lactis* subsp. *lactis Il*1403 16S rDNA (SEQ ID NO: 1). In other embodiments, the probiotic comprises a 16S rDNA sequence at least 91%, 92%, 93%, 94%, 95%, 96%, 97%, 98%, or 99% or more identical to the SEQ ID NO:1 16S rDNA sequence from *L. lactis* subsp. *lactis Il*1403.

In some embodiments, the probiotic disclosed herein is *Lactobacillus casei*, or a species containing 16s rDNA with at least 90% sequence identity to *Lactobacillus casei* strain JCM1171 16S rDNA (SEQ ID NO: 7). In other embodiments, the probiotic comprises a 16S rDNA sequence at least 91%, 92%, 93%, 94%, 95%, 96%, 97%, 98%, or 99% or more identical to the SEQ ID NO:7 16S rDNA sequence from *Lactobacillus casei* strain JCM1171.

In some embodiments, the probiotic disclosed herein is *Lactibacillus paracasei*, or a species containing 16s rDNA with at least 90% sequence identity to *Lactobacillus paracasei* strain 10C 16S rDNA (SEQ ID NO: 8). In other embodiments, the probiotic comprises a 16S rDNA sequence at least 91%, 92%, 93%, 94%, 95%, 96%, 97%, 98%, or 99% or more identical to the SEQ ID NO:8 16S rDNA sequence from *Lactobacillus paracasei* strain 10C.

In one embodiment, the probiotic that reduces reactive oxygen species is sensitive to lysozymes. *L. lactis* bacterial cells are sensitive to the bacterial lysis-inducing enzyme, lysozyme. Lysis of *L. lactis*, or another lysozyme-sensitive species via lysozyme spills the contents of the bacterium, releasing SodA or other antioxidant enzymes into the cell's environment, allowing such enzymes to reduce reactive oxygen species.

Agents that Reduce Reactive Oxygen Species

In some embodiments, an agent that reduces reactive oxygen species is administered to help counter the effects of SD. As used herein, the term "agent" refers to molecules and/or compositions including, but not limited to chemical compounds and mixtures of chemical compounds, e.g., small organic or inorganic molecules; saccharides; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; aptamers; and antibodies and intrabodies, or antigen-binding fragments thereof.

Table 2 shows a non-limiting list of agents that reduce reactive oxygen species that were effective in reversing SD-induced defects in the animal model.

TABLE 2

Compounds that were effective in increasing survival of sleep-deprived flies

| | Chemical structure | Known biological functions | Therapeutic use |
|---|---|---|---|
| β-Carotene | 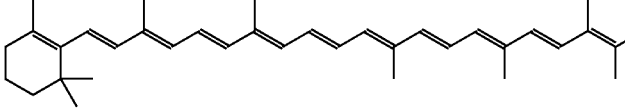 | Most well-known provitamin A Antioxidant | Asthma caused by exercise Certain cancers Heart disease Cataracts and age related macular degeneration AIDS Alcoholism Alzheimer's and Parkinson's diseases Schizophrenia Depression Epilepsy High blood pressure Infertility Rheumatoid arthritis Skin disorders (psoriasis, vitiligo) |
| Catechin | 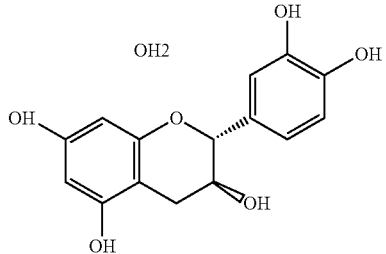 [SMILES: Oc1cc(O)c2c(c1)O[C@H](c1ccc(O)c(O)c1)[C@@H](O)C2 ; O] | Antioxidant Vascular function Possible immune effects | Heart disease Neurological disorders Liver protective Obesity Diabetes Cancer |
| Coenzyme Q10 | 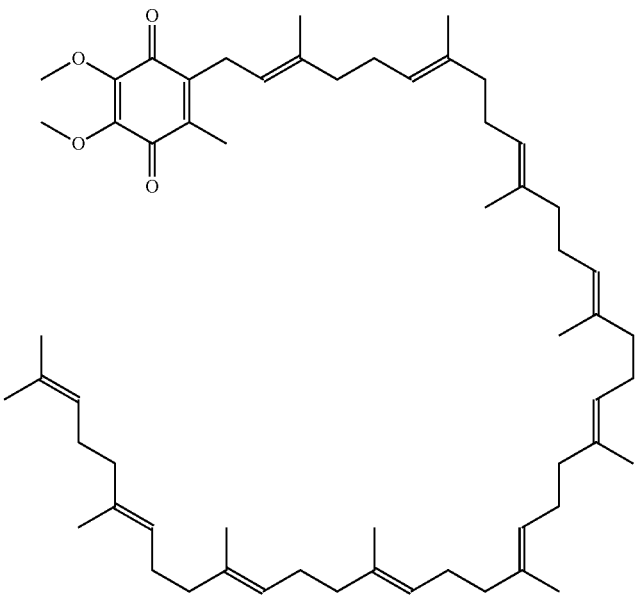 [SMILES: COC1=C(OC)C(=O)C(C/C=C(\C)CC/C=C(\C)CC/C=C(\C)CC/C=C(\C)CC/C=C(\C)CC/C=C(\C)CC/C=C(\C)CC/C=C(\C)CC/C=C(\C)CCC=C(C)C)=C(C)C1=O] | Antioxidant ATP production | Cardioprotective Huntington's and Parkinson's disease Muscular dystrophy Lyme disease Cancer AIDS Infertility |

TABLE 2-continued

Compounds that were effective in increasing survival of sleep-deprived flies

| | Chemical structure | Known biological functions | Therapeutic use |
|---|---|---|---|
| Lipoic acid | 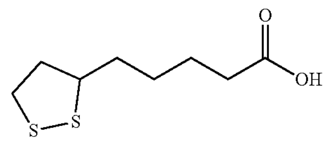 [SMILES: O=C(O)CCCCC1CCSS1] | Antioxidant<br>Restores vitamin levels (vitamins E and C)<br>Improves the function and conduction of neurons in diabetes | Heart disease<br>Lyme disease<br>Diabetes<br>Cancer<br>HIV<br>Liver disease<br>Eye-related disorders<br>Vitiligo |
| Melatonin | 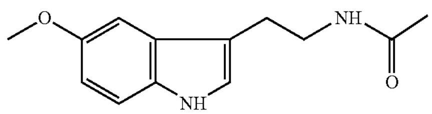 [SMILES: COc1ccc2[nH]cc(CCNC(C)=O)c2c1] | Antioxidant<br>Sleep hormone | Sleep disorders<br>Jet lag<br>Neurological disorders<br>Cancer |
| Metformin | 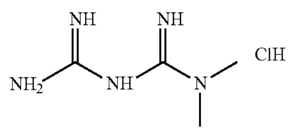 | Antioxidant<br>Decreases liver glucose production and increases insulin sensitivity | Diabetes<br>Cardiovascular disease<br>Cancer |
| NAC | 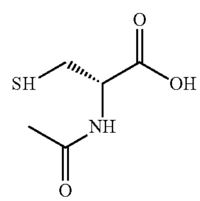 | Antioxidant<br>Increases glutathione levels | Cystic fibrosis or chronic obstructive pulmonary disease<br>Cancer<br>ALS, Alzheimer's disease<br>AIDS<br>Hepatitis<br>Kidney disease |
| NAD | 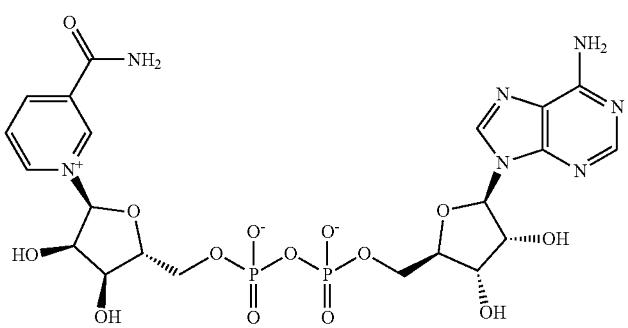 [SMILES: NC(=O)c1ccc[n+]([C@H]2O[C@H](COP(=O)([O-])OP(=O)([O-])OC[C@H]3O[C@@H](n4cnc5c(N)ncnc54)[C@H](O)[C@@H]3O)[C@@H](O)[C@H]2O)c1] | Antioxidant<br>Redox coenzyme<br>Used by sirtuins | Neurological disorders (Alzheimer, Parkinson)<br>Cancer |
| NHGA | 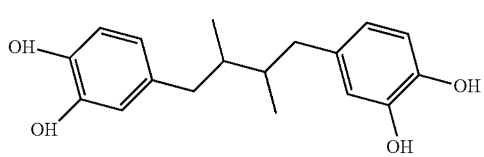 [SMILES: CC(Cc1ccc(O)c(O)c1)C(C)Cc1ccc(O)c(O)c1] | Antioxidant<br>Anti-inflammatory | Cardiovascular diseases<br>Neurological disorders<br>Cancer<br>Inflammation |
| PBA | 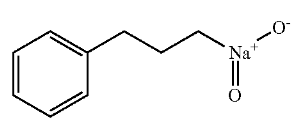 | Antioxidant<br>Histone deacetylase inhibitor<br>Chemical chaperone<br>Anti-inflammatory activity in neurons | Urea cycle disorder<br>Cancer<br>Cystic fibrosis<br>Neurological disorders (Parkinson, Huntington)<br>Motor neuron diseases (ALS) |

TABLE 2-continued

Compounds that were effective in increasing survival of sleep-deprived flies

| | Chemical structure | Known biological functions | Therapeutic use |
|---|---|---|---|
| Quercetin | 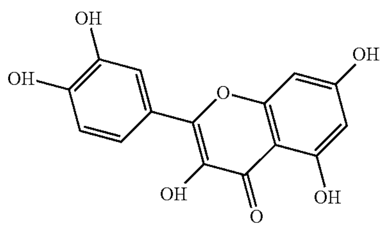 [SMILES: O=c1c(O)c(-c2ccc(O)c(O)c2)oc2cc(O)cc(O)c12] | Antioxidant<br>Non-specific protein kinase enzyme inhibitor | Heart disease<br>Diabetes<br>Cataracts<br>Schizophrenia<br>Gout<br>Cancer |
| Tyrosol | 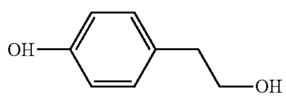 | Antioxidant<br>SIRT1, Akt and eNOS activator | Cancer<br>Heart disease |
| Urso-deoxicholic acid | 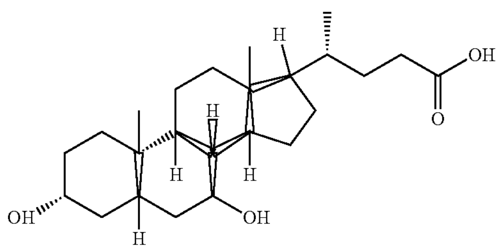 | Antioxidant<br>secondary bile acid (fat digestion) | Bile diseases<br>Liver diseases |
| Vitamin C | 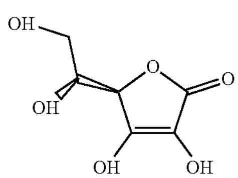 [SMILES: O=C1O[C@H]([C@@H](O)CO)C(O)=C1O] | Antioxidant<br>Repair of tissue | Cardiovascular disease<br>Cancer<br>Age related macular degeneration<br>Rheumatoid arthritis<br><br>Common cold |
| Vitamin E | 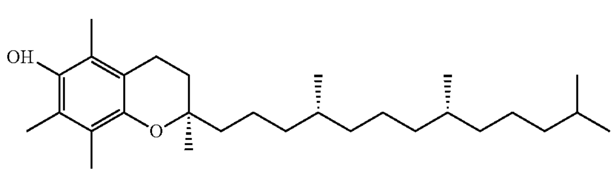 [SMILES: Cc1c(C)c2c(c(C)c1O)CC[C@@](C)(CCC[C@H](C)CCC[C@H](C)CCCC(C)C)O2] | Fat-soluble antioxidant (glutathione peroxidase pathway)<br>Neurological functions<br>Inhibition of<br><br>platelet coagulation | Cardiovascular disease<br>Cancer<br>Neurological disorders |

Table 3 shows a non-limiting list of agents that reduce reactive oxygen species that were ineffective in reversing SD-inducing defects in the animal model in this screen.

TABLE 3

Compounds that were INEFFECTIVE in increasing survival of sleep-deprived flies

| | Chemical structure | Known biological functions | Therapeutic use |
|---|---|---|---|
| Acarbose | [structure] | Anti-diabetic | Diabetes |
| Acetylsalicylic acid | [structure] | Antioxidant Anti-inflammatory | Pain Fever Inflammation Heart attack Cancer |
| alpha-amylase | | Digestive enzyme | Pancreatitis Cancer Immunosuppressive |
| Rapamycin | [structure] | Antioxidant Antibiotic Immunosuppressive | Coronary stent coating Cancer Transplant rejection Lymphangioleiomyomatosis |

In some embodiments, the agent that reduces reactive oxygen species includes the compound β-carotene. β-carotene is an organic, strongly colored red-orange pigment abundant in plants and fruits. It is a member of the carotenes, which are terpenoids (isoprenoids), synthesized biochemically from eight isoprene units and thus having 40 carbons. Among the carotenes, β-Carotene is distinguished by having beta-rings at both ends of the molecule. β-Carotene is biosynthesized from geranylgeranyl pyrophosphate. β-carotene is a carotenoid and an antioxidant.

In some embodiments, the agent that reduces reactive oxygen species includes the compound lipoic acid. Also known as α-lipoic acid, alpha lipoic acid (ALA), and thioctic acid, it is an organosulfur compound derived from octanoic acid. ALA is made in animals normally, and is essential for aerobic metabolism. It is also manufactured and is available as a dietary supplement in some countries where it is marketed as an antioxidant, and is available as a pharmaceutical drug in other countries. While it is generally agreed that ALA has antioxidant effects overall, the mechanism of action of ALA when supplied externally to an organism is not agreed upon. Recent findings suggest therapeutic and anti-aging effects of ALA are due to modulation of signal transduction and gene transcription, which improve the antioxidant status of the cell. However, this likely occurs via pro-oxidant mechanisms, not by direct radical scavenging or reducing effects.

In some embodiments, the agent that reduces reactive oxygen species includes the compound ascorbic acid or "vitamin C." Vitamin C is a monosaccharide oxidation-reduction (redox) catalyst found in both animals and plants. As one of the enzymes needed to make ascorbic acid has been lost by mutation during primate evolution, humans must obtain it from the diet. Ascorbic acid is a redox catalyst which can reduce, and thereby neutralize, reactive oxygen species such as hydrogen peroxide.

In some embodiments, the agent that reduces reactive oxygen species includes the compound vitamin E. Vitamin E is the collective name for a set of eight related tocopherols and tocotrienols, which are fat-soluble vitamins with antioxidant properties. Of these, α-tocopherol has been most studied as it has the highest bioavailability, with the body preferentially absorbing and metabolizing this form. While not wishing to be bound by theory, some view the α-tocopherol form as the most important lipid-soluble antioxidant, as it protects membranes from oxidation by reacting with lipid radicals produced in the lipid peroxidation chain reaction. This removes the free radical intermediates and prevents the propagation of the reaction. This reaction produces oxidized α-tocopheroxyl radicals that can be recycled back to the active reduced form through reduction by other antioxidants, such as ascorbate, retinol or ubiquinol. This is in line with findings showing that α-tocopherol, but not water-soluble antioxidants, efficiently protects glutathione peroxidase 4 (GPX4)-deficient cells from cell death. GPX4 is the only known enzyme that efficiently reduces lipid-hydroperoxides within biological membranes.

In some embodiments, the agent that reduces reactive oxygen species is the compound Coenzyme Q10 (ubiquinone). Ubiquinone is a coenzyme that is ubiquitous in the bodies of most animals. It is a 1,4-benzoquinone, where Q refers to the quinone chemical group and 10 refers to the number of isoprenyl chemical subunits in its tail. There are three redox states of $CoQ_{10}$: fully oxidized (ubiquinone), semiquinone (ubisemiquinone), and fully reduced (ubiquinol). The capacity of this molecule to act as a two-electron carrier (moving between the quinone and quinol form) and a one-electron carrier (moving between the semiquinone and one of these other forms) is central to its role in the electron transport chain due to the iron-sulfur clusters that can only accept one electron at a time, and as a free radical-scavenging antioxidant.

In some embodiments, the agent that reduces reactive oxygen species includes the compound Nordihydroguaiaretic acid (NDGA). NDGA is an antioxidant compound found in the creosote bush (*Larrea tridentata*).

In some embodiments, the agent that reduces reactive oxygen species includes the compound ursodeoxycholic acid. Ursodeoxycholic acid also known as ursodiol (USAN) and the abbreviation UDCA, is one of the secondary bile acids, which are metabolic byproducts of intestinal bacteria. UDCA has direct antioxidant properties, which are especially relevant against Fe(3+)- and hydroxyl-radical dependent biomolecular oxidative damage; such properties are evident at therapeutically relevant drug concentrations, indicating that UDCA can act as an antioxidant in vivo.

In some embodiments, the agent that reduces reactive oxygen species includes the compound melatonin. Melatonin, also known as N-acetyl-5-methoxy tryptamine, is a hormone that is produced by the pineal gland in animals and regulates sleep and wakefulness. Melatonin is also produced in plants where it functions as a first line of defense against oxidative stress. In animals, melatonin is involved in the entrainment (synchronization) of the circadian rhythms including sleep-wake timing, blood pressure regulation, seasonal reproduction, and many others. Many of its biological effects in animals are produced through activation of melatonin receptors, while others are due to its role as an antioxidant, with a particular role in the protection of nuclear and mitochondrial DNA. Melatonin is a powerful antioxidant, and easily crosses cell membranes and the blood-brain barrier. Unlike other antioxidants, melatonin does not undergo redox cycling, which is the ability of a molecule to undergo repeated reduction and oxidation. Redox cycling may allow other antioxidants (such as vitamin C) to act as pro-oxidants and promote free radical formation. Melatonin, once oxidized, cannot be reduced to its former state because it forms several stable end-products upon reacting with free radicals. Therefore, it has been referred to as a terminal (or suicidal) antioxidant.

In some embodiments, an agent that reduces reactive oxygen species includes the small molecule 4-phenylbutyrate (PBA). This compound is used to treat urea cycle disorders, because its metabolites offer an alternative pathway to the urea cycle to allow excretion of excess nitrogen. It is an orphan drug, marketed by Ucyclyd Pharma under the trade name Buphenyl, by Swedish Orphan International (Sweden) as Ammonaps, and by Fyrlklövern Scandinavia as triButyrate. Phenylbutyrate is a prodrug—in the human body it is first converted to phenylbutyryl-CoA and then metabolized by mitochondrial beta-oxidation, mainly in the liver and kidneys, to the active form, phenylacetate. PBA has also been shown to induce expression of SOD (Benzer, et al. 2001. PNAS).

In some embodiments, an agent that reduces reactive oxygen species is the small molecule catechin. Catechin is a flavan-3-ol, a type of natural phenol and antioxidant. It is a plant secondary metabolite. It belongs to the group of flavan-3-ols (or simply flavanols), part of the chemical family of flavonoids. Catechin possesses two benzene rings (called the A- and B-rings) and a dihydropyran heterocycle (the C-ring) with a hydroxyl group on carbon 3. The A ring is similar to a resorcinol moiety while the B ring is similar to a catechol moiety. There are two chiral centers on the molecule on carbons 2 and 3. Therefore, it has four diastereoisomers. Two of the isomers are in trans configuration and are called catechin and the other two are in cis configuration and are called epicatechin.

In some embodiments, an agent that reduces reactive oxygen species includes the small molecule metformin. Metformin is marketed under the trade name Glucophage™ (Bristol Myers Squibb) among others, is the first-line medication for the treatment of type 2 diabetes, but is a strong antioxidant. There is evidence that metformin reduces cell mutations and DNA damage, and it likely does so by reducing levels of reactive oxygen species.

In some embodiments, an agent that reduces reactive oxygen species includes the small molecule N-Acetyl Cysteine (NAC). Also known N-acetyl-L-cysteine, NAC is an antioxidant medication used to treat paracetamol (acetaminophen) overdose, which causes oxidative damage to the liver.

In some embodiments, an agent that reduces reactive oxygen species includes the small molecule nicotinamide-adenine dinucleotide (NAD). NAD is a coenzyme found in all living cells. The compound is a dinucleotide, consisting of two nucleotides joined through phosphate groups. One nucleotide contains an adenine base and the other nicotinamide. Nicotinamide adenine dinucleotide exists in two forms, an oxidized and reduced form abbreviated as $NAD^+$ and NADH respectively. The nicotinamide moiety can be attached in two orientations to an anomeric carbon atom. Because of these two possible structures, the compound exists as two diastereomers. It is the β-nicotinamide diastereomer of $NAD^+$ that is found in organisms. Nicotinamide adenine dinucleotide has several essential roles in metabolism. It acts as a coenzyme in redox reactions, as a donor of ADP-ribose moieties in ADP-ribosylation reactions, as a precursor of the second messenger molecule cyclic ADP-ribose, as well as acting as a substrate for bacterial DNA ligases and a group of sirtuin enzymes that use $NAD^+$ to remove acetyl groups from proteins. In some embodiments, an agent that reduces reactive oxygen species is an NAD precursor. Non-limiting examples of NAD precursors include nicotinic acid, nicotinamide, and nicotinamide riboside.

In some embodiments, the agent that reduces reactive oxygen species includes quercetin. Quercetin is a plant polyphenol from the flavonoid group, found in many fruits, vegetables, leaves, and grains. Quercetin has been reported to inhibit the oxidation of other molecules and hence is classified as an antioxidant. Quercetin contains a polyphenolic chemical substructure that stops oxidation by acting as a scavenger of free radicals that are responsible for oxidative chain reactions.

In some embodiments the agent that reduces reactive oxygen species includes tyrosol. Tyrosol is a phenylethanoid, a derivative of phenethyl alcohol. It is a natural phenolic antioxidant present in a variety of natural sources. The principal source in the human diet is olive oil. It is also one of the main natural phenols in argan oil.

In some embodiments, the agent that reduces reactive oxygen species is a nitric oxide synthase inhibitor. In one embodiment, the nitric oxide synthase inhibitor is L-NMMA (NG-Methyl-L-arginine, acetate salt). L-NMMA is a competitive inhibitor of nitric oxide synthase. Additional inhibitors of nitric oxide synthase include, but are not limited to, —NIO (N5-(1-Iminoethyl)-L-ornithine, dihydrochloride); L-NIL (N6-(1-Iminoethyl)-lysine, hydrochloride); L-NI (L-Nitroindazole).

Additional, non-limiting examples of agents that can reduce reactive oxygen species include, but are not limited to Ascorbic acid, Sodium ascorbate, Calcium ascorbate, Fatty acid esters of ascorbic acid, Tocopherols, Gamma-tocopherol, Delta-tocopherol, Propyl gallate, Octyl gallate, Dodecyl gallate, Erythorbic acid, Sodium erythorbate, Dodecyl gallate, Tertiary-butyl hydroquinone (TBHQ), Butylated hydroxyanisole (BHA), Butylated hydroxytoluene (BHT), Citric Acid, and 4-Hexylresorcinol. These agents have been used as food additive for their antioxidant properties, and are generally recognized as safe.

A further non-limiting example of an additional small molecule that reduce reactive oxygen species is Tirilazad, which inhibits lipid peroxidation.

Enzymes that Act on Reactive Oxygen Species

In some embodiments, rather than directly reducing reactive oxygen species by chemical reaction with reactive oxygen species, an agent as described herein is an enzyme that catalyzes a reaction that connects one or more reactive oxygen species species to either a less reactive species or a species such as $H_2O_2$ that is further inactivated, e.g., another enzyme such as a catalase. Non-limiting examples of enzymes that reduce reactive oxygen species include catalase, superoxide dismutase, thioredoxin reductase, glutathione reductase, glutathione peroxidase, and glutathione S-transferase. The enzymes can be of bacterial, fungal, or other origin, including enzymes of mammalian origin. In one embodiment, the enzyme is a superoxide dismutase, which can include, among others, a bacterial SodA polypeptide.

Therapeutic Compositions and Methods

In various embodiments, the damaging effects of SD, and in particular embodiments, the damaging effects of SD on the gut, can be prevented, treated or ameliorated by administration of a probiotic and/or an agent that reduces reactive oxygen species as described herein. Therapeutic methods, as well as formulations are discussed in the following.

In one embodiment, a composition for treating the damaging effects of SD includes a probiotic and/or an agent that reduces reactive oxygen species as described herein or as known in the art. In one aspect, a composition comprising a probiotic and/or an agent that reduces reactive oxygen species is administered to an individual who is, or is likely to become, sleep-deprived, to treat and/or prevent SD-induced accumulation of reactive oxygen species and/or oxidative tissue damage. In one embodiment, the accumulation of reactive oxygen species and/or oxidative tissue damage occurs in the intestinal gut. In one embodiment of this and other aspects described herein, the method of treatment or prevention further comprises the step, before the administering step, of selecting an individual who is or is at risk of becoming sleep-deprived. Probiotics useful in such embodiments reduce the amount or accumulation of reactive oxygen species, e.g., by expressing and/or secreting one or more factor(s) that reduce reactive oxygen species, either directly by chemical reaction with reactive oxygen species, or by catalyzing one or more reactions that reduce the amount or accumulation of reactive oxygen species. The probiotics, as described herein above, can express and/or secrete the factor(s) naturally, or be engineered to express such factor(s).

Agents that reduce reactive oxygen species as described herein or as known in the art can be administered in amounts and formulations as described herein or as known in the art to exert effects on levels or activities of reactive oxygen species. Similarly, a probiotic that reduces reactive oxygen species can be administered in amounts and formulations as described herein or as known in the art to exert effects on levels or activities of reactive oxygen species, e.g., reactive oxygen species in their environments. Such probiotic can, in some embodiments, be sensitive to lysozyme, such that lysis of the cell when exposed to lysozyme releases a factor or enzyme that reduces reactive oxygen species.

In one aspect, a composition for treating the damaging effects of SD includes a probiotic and/or an agent that reduces reactive oxygen species as described herein or as known in the art and a sedative. In one aspect, a composition comprising a probiotic and/or an agent that reduces reactive oxygen species and a sedative is administered to an individual who is sleep-deprived to treat and/or prevent the accumulation or activity of reactive oxygen species and/or oxidative tissue damage that occurs with SD. In one embodiment of these aspects, the administration of a composition comprising a probiotic and/or an agent that reduces reactive oxygen species is to an individual who is likely to become sleep-deprived, so as to ameliorate and/or prevent SD-induced accumulation of reactive oxygen species and/or oxidative tissue damage. In another embodiment of these aspects, the administration prevents or treats the accumulation of reactive oxygen species and/or oxidative tissue damage in the intestinal gut. In one embodiment, the method of treatment or prevention further comprises the step, before the administering step, of selecting an individual who is or is at risk of becoming sleep-deprived. Probiotics useful in such embodiments reduce the amount or accumulation of reactive oxygen species, e.g., by expressing and/or secreting one or more factor(s) that reduce reactive oxygen species, either directly by chemical reaction with reactive oxygen species, or by catalyzing one or more reactions that reduce the amount or accumulation of reactive oxygen species. The probiotics, as described elsewhere herein, can express and/or secrete the factor(s) naturally, or be engineered to express such factor(s).

A "sedative" is a substance that induces sedation by reducing irritability or excitement. Sedatives can promote or induce sleep. It is contemplated that administration of a sedative, in conjunction with a probiotic or agent that reduces reactive oxygen species as described herein can both assist sleep in an individual who is unable to fall asleep or to remain asleep, and counter or ameliorate the accumulation of reactive oxygen species and/or tissue damage that normally occurs with SD. It is contemplated that administering a sedative, in conjunction with a probiotic or agent that reduces reactive oxygen species as described herein can also promote more rapid recovery from SD than would occur without such administration. Doses of sedatives such as benzodiazepines, when used as a hypnotic to induce sleep, tend to be higher than amounts used to relieve anxiety, whereas only low doses are needed to provide a peaceful effect. As used herein, the term "sedation" refers to calm, relaxation, or sleep due to the intake of a sedative.

Non-limiting examples of sedatives include barbiturates, benzodiazepines, non-benzodiazepine hypnotics, methoaqualones, first generation antihistamines, antidepressants, antipsychotics, herbal sedatives, alcohol, opioids, general anesthetics, melatonin agonists, orexin antagonists, and skeletal muscle relaxants. For purposes of compositions including a sedative, it should be understood that the sedative is present and administered in an amount sufficient to have a sedative effect. For example, while alcohol (ethanol) can have a sedative effect, it is also used as a solvent for some pharmaceutical formulations; however, in these instances, the ethanol is generally not present in an amount sufficient to have a significant sedative effect.

In one aspect, a composition for treating the damaging effects of SD includes a probiotic and/or an agent that reduces reactive oxygen species as described herein or as known in the art, and a stimulant. In another aspect, a composition comprising a probiotic and/or an agent that reduces reactive oxygen species and a stimulant is administered to an individual who is sleep-deprived to treat and/or prevent SD-induced tissue damage. In one embodiment of these aspects, the administration of a composition comprising a probiotic and/or an agent that reduces reactive oxygen species and a stimulant is to an individual who is likely to become sleep-deprived, so as to ameliorate and/or prevent SD-induced accumulation of reactive oxygen species and/or oxidative tissue damage. In another embodiment of these aspects, the administration prevents or treats the accumulation of reactive oxygen species and/or oxidative tissue damage in the intestinal gut. In another embodiment, the method of treatment or prevention further comprises the step, before the administering step, of selecting an individual who is or is at risk of becoming sleep-deprived. Probiotics useful in such embodiments reduce the amount or accumulation of reactive oxygen species, e.g., by expressing and/or secreting one or more factor(s) that reduce reactive oxygen species, either directly by chemical reaction with reactive oxygen species, or by catalyzing one or more reactions that reduce the amount or accumulation of reactive oxygen species. The probiotics, as described elsewhere herein, can express and/or secrete the factor(s) naturally, or be engineered to express such factor(s).

"Stimulant" is an overarching term that encompasses drugs that increase alertness or activity of the body, drugs that are invigorating, and/or drugs that have sympathomimetic effects. In general, a stimulant can keep an individual awake longer than they would remain awake without the stimulant. It is contemplated that administration of a stimulant, in conjunction with a probiotic or agent that reduces reactive oxygen species as described herein can both keep awake an individual who needs to stay awake, and prevent, or at least ameliorate the accumulation of reactive oxygen species and/or tissue damage that normally occurs with SD. Stimulants are widely used throughout the world as prescription medicines as well as without a prescription (either legally or illicitly) as performance-enhancing or recreational drugs.

Non-limiting examples of stimulants include herbal stimulants, amphetamines, methamphetamines, cocaine, methylxanthines, ephedrine, cathinones, mephedrone, methylenedioxypyrovalerone, methylenedioxymethamphetamine, nicotine, propylhexedrine, and pseudoephedrine.

As used herein, the term "reducing" with respect to targeting of reactive oxygen species refers to attenuating chemical reactivity and/or levels of such reactive oxygen species.

Various embodiments noted herein involve selecting an individual who is sleep-deprived, or administering a probiotic or an agent that reduces reactive oxygen species to an individual who is sleep deprived. A sleep deprived individual is defined as one who is getting at least 10%, or at least 20%, or at least 30%, or at least 40%, or at least 50%, or at least 60%, or at least 70%, or at least 80%, or at least 90% or more, less sleep than recommended for their age group.

As used herein, the term "reduce" when used in reference to the level or activity of a targeted product, e.g., reactive oxygen species, refers to a decrease in the level and/or activity of the targeted product by at least 10% or more, e.g. by 10% or more, 50% or more, 70% or more, 80% or more, 90% or more, 95% or more, or 98% or more. The efficacy of an inhibitor of a particular target, e.g. its ability to decrease the level and/or activity of the target can be determined, e.g. by measuring the level of an expression product and/or the activity of the target. Any appropriate method can be used, however one way to measure the levels of reactive oxygen species uses, for example, a DCFDA-Cellular reactive oxygen species detection assay kit (ab113851, Abcam; Cambridge, Mass.). Additional methods are known in the art and/or described in the Examples herein.

Dosage Forms and Administration

The dosages of probiotics and/or agents that reduce reactive oxygen species to be administered can be determined by one of ordinary skill in the art depending on the clinical severity of the disorder (e.g., SD), the age and weight of the patient, the exposure of the patient to conditions that may precipitate sleep deprivation, and other pharmacokinetic factors generally understood in the art, such as liver and kidney metabolism. The interrelationship of dosages for animals of various sizes and species and humans based on mg/m$^3$ of surface area is described by E. J. Freireich et al., "Quantitative Comparison of Toxicity of Anticancer Agents in Mouse, Rat, Hamster, Dog, Monkey and Man," Cancer Chemother. Rep. 50: 219-244 (1966). Adjustments in the dosage regimen can be made to optimize the therapeutic response. Doses can be divided and administered on a daily basis or the dose can be reduced proportionally depending on the therapeutic situation.

In some embodiments, probiotics that reduce reactive oxygen species are administered to a subject who is sleep-deprived to treat and/or prevent damage due to SD. Parts of the microorganisms and/or spores can be separated and selected, using any one of a number of methods that are well known to those of ordinary skill in the art, for their bioactive properties to help ensure and improve the rate of reactive oxygen species reduction. An effective amount of microorganisms and/or their spores is an amount sufficient to reduce excess reactive oxygen species levels that cause cellular damage due to SD. In accordance with these embodiments, an effective amount of microorganisms is from 100 thousand to 500 thousand, from 500 thousand to 1 million, from 1 million to 50 million, from 50 million to 100 million, from 100 million to 500 million, from 500 million to 1 billion, from 1 billion to 50 billion, from 50 billion to 100 billion, from 100 billion to 500 billion, from 500 billion to 600 billion CFU per dose, where the dose is administered about one or more times per week, or as often as about one to three times daily.

The dosage range depends upon the potency, and includes amounts large enough to produce the desired effect, e.g., a decrease cellular damage. The dosage should not be so large as to cause unacceptable adverse side effects. Generally, the dosage will vary with the type of agent (e.g., an antibody or fragment, small molecule, siRNA, etc.), and with the age, condition, and sex of the patient. The dosage can be determined by one of skill in the art and can also be adjusted by the individual physician in the event of any complication. Typically, the dosage will range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

The means by which the probiotics or agents described herein should be administered should be appropriate for the given probiotic or agent. Typically, but not necessarily, these probiotics or agents are administered orally. Probiotics can be administered in a suspension in liquid form, in a slurry in a capsule, or, for example, in dried form in a capsule. Methods for maintaining viability of probiotics throughout the drying process are known to those of skill in the art. Probiotics, including, but not limited to dried preparations, can also be formulated in enteric-coated or other forms such that when administered orally the probiotics avoid killing in the harsh acidic conditions of the stomach and are only released to re-hydrate/reactivate in the relatively safer environment of the intestine. Probiotics can also be administered in admixture with a food or beverage product, including, but not limited to a yogurt, kefir or other dairy product, or as dried microbes in, for example, a bar of cereal, granola, etc. Probiotics useful in the methods and compositions described herein can also be prepared and/or administered in admixture with one or more prebiotic compositions that promote the maintenance, establishment and/or growth of the probiotic. Prebiotics include any of a number of compositions that are generally not directly digestible by humans, but that are readily digestible by and promote the growth or establishment of probiotic microbes. Non-limiting examples of prebiotics include inulin, fructooligosaccharides, galactooligosaccharides, hemicelluloses (e.g., arabinoxylan, xylan, xyloglucan, and glucomannan), chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

Agents that reduce reactive oxygen species can be administered, for example, in conventional pill or liquid form. If administered in pill form, they can be administered in conventional formulations with excipients, fillers, preservatives, and other typical ingredients used in pharmaceutical formations in pill form. Typically, the drugs are administered in a conventional pharmaceutically acceptable formulation, typically including a pharmaceutically acceptable carrier. Conventional pharmaceutically acceptable carriers known in the art can include alcohols, e.g., ethyl alcohol, serum proteins, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and the like. A pharmaceutically-acceptable carrier within the scope of the present technology meets industry standards for sterility, isotonicity, stability, and non-pyrogenicity.

A pharmaceutically acceptable formulation can also be in pill, tablet, or lozenge form as is known in the art, and can include excipients or other ingredients for greater stability or acceptability. For the tablets, the excipients can be inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc, along with the agent that reduces reactive oxygen species and other ingredients.

Agents that reduce reactive oxygen species can also be administered in liquid form in conventional formulations that can include preservatives, stabilizers, coloring, flavoring, and other generally accepted pharmaceutical ingredients. Typically, when the drugs are administered in liquid form, they will be in aqueous solution. The aqueous solution can contain buffers, and can contain alcohols such as ethyl alcohol or other pharmaceutically tolerated compounds.

An agent can comprise, for example, at least 0.1%, or at least 1%, or at least 2%, or at least 3%, or at least 4%, or at least 5%, or at least 6%, or at least 7%, or at least 8%, or at least 9%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% by weight of a formulation useful in the methods and compositions described herein.

A variety of means for administering agents that reduce reactive oxygen species to subjects are known to those of skill in the art. Such methods can include, but are not limited to oral, parenteral, intravenous, subcutaneous, transdermal, airway (aerosol), pulmonary, cutaneous, topical, or injection. Administration can be local or systemic. When administered to treat, prevent or ameliorate the accumulation of reactive oxygen species or oxidative tissue damage to the gut, oral administration is preferred, although administration via the rectum, e.g., via suppository or other appropriate dosage form is contemplated.

The probiotic or agent can be administered from once per day up to at least five times per day, depending on the severity of the SD-induced damage and anticipated duration of SD, the total dosage to be administered, and the judgment of the treating physician. In some cases, the drugs need not be administered on a daily basis, but can be administered every other day, every third day, or on other such schedules, again depending upon the anticipated duration of SD.

Therapeutic compositions containing a probiotic or agent that reduces reactive oxygen species can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

A therapeutically effective amount is an amount of an agent that reduces reactive oxygen species sufficient to produce a statistically significant, measurable change in e.g., reversal of damage, etc. (see "Efficacy Measurement" below). Such effective amounts can be gauged in clinical trials as well as animal studies for a given reduction agent.

Efficacy Measurement

The efficacy of a given treatment or prevention for damage caused by sleep deprivation can be determined by the skilled clinician. However, a treatment is considered "effective treatment," as the term is used herein, if any one or all of the signs or symptoms of, as but one example, damage localized to a site are altered in a beneficial manner, or other clinically accepted symptoms or markers of disease are improved or ameliorated, e.g., by at least 10% following treatment with a probiotic and/or agent that reduces reactive oxygen species as described herein. Efficacy can also be measured by failure of an individual to worsen as assessed by need for medical interventions (e.g., progression of damage or accumulation of reactive oxygen species is halted or at least slowed). Markers for inflammatory bowel disease, a disease characterized by its cellular damage, are ideal markers for assessing SD-induced damage. These markers include increased levels of proinflammatory cytokines, such as interleukin-1 and -8 and tumor necrosis factor, and increased calprotectin or lactoferrin. Methods of measuring these indicators are known to those of skill in the art and/or described herein. Treatment includes any treatment of a disease in an individual or an animal (some non-limiting examples include a human, or a mammal) and includes: (1) inhibiting the damage, e.g., arresting, or slowing damage induced by SD; or (2) relieving the damage, e.g., causing regression of symptoms, reducing the damage by at least 10%; and (3) preventing or reducing the likelihood of the further damage.

An effective amount for the treatment of SD-induced damage means that amount which, when administered to a mammal in need thereof, is sufficient to result in effective treatment as that term is defined herein, for that defect. Efficacy of an agent can be determined by assessing physical indicators of SD-induced damage, such as e.g., cellular damage, and apoptosis, as well as by evaluating the well-being and alertness of the subject receiving treatment.

The term "effective amount" as used herein refers to the amount of a probiotic or agent that reduces reactive oxygen species described herein needed to alleviate at least one or more symptom of SD, and relates to a sufficient amount of pharmacological composition to provide the desired effect. The term "therapeutically effective amount" therefore refers to an amount of a composition that is sufficient to provide a particular anti-damage effect when administered to a sleep deprived, typical subject. An effective amount as used herein, in various contexts, would also include an amount sufficient to delay the development of a symptom of the disorder, alter the course of a symptom (for example but not limited to, slowing the progression of a symptom of the disorder), or reverse a symptom of the disorder. Thus, it is not generally practicable to specify an exact "effective amount." However, for any given case, an appropriate "effective amount" can be determined by one of ordinary skill in the art using only routine experimentation. The term "effective amount" is used interchangeably with the term "therapeutically effective amount" and refers to the amount of at least one agent, e.g., probiotic and/or agent that reduced reactive oxygen species, of a pharmaceutical composition, at dosages and for periods of time necessary to achieve the desired therapeutic result, for example, to reduce or stop at least one symptom of SD-induced damage, in the subject.

Effective amounts, toxicity, and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from in vivo assays. Also, a dose can be formulated in animal models to achieve a circulating plasma concentration range that includes the $IC_{50}$ (i.e., the concentration of the active ingredient, which achieves a half-maximal inhibition of symptoms). Levels in plasma can be measured, for example, by high performance liquid chromatography or other appropriate technique. It is contemplated that the relevant level for an agent that reduced reactive oxygen species may also be the level achieved in the lumen of the gut, as opposed to a circulating level. The effects of any particular dosage can be monitored by a suitable bioassay. The dosage can be determined by a physician and adjusted, as necessary, to suit observed effects of the treatment.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1) A method for treating damage induced by sleep deprivation (SD), the method comprising: administering to an individual who is sleep deprived a probiotic that reduces reactive oxygen species.
2) The method of paragraph 1, wherein the damage occurs at a site selected from the group consisting of: brain, gastrointestinal tract, mouth, throat, lungs, heart, liver, gut, stomach, kidney, skin, bones, large intestine, small intestine, bladder, and muscular system.
3) The method of paragraph 1, wherein the damage occurs in the gut.
4) The method of paragraph 1, wherein SD is chronic or acute.
5) The method of paragraph 1, wherein the probiotic expresses a superoxide dismutase polypeptide.
6) The method of paragraph 5, wherein the superoxide dismutase polypeptide is a superoxide dismutase A (SodA) polypeptide.
7) The method of paragraph 1, wherein the probiotic is selected from the group consisting of: *Streptococcus thermophilus, Lactobacillus casei, Lactococcus lactis,* and *Lactobacillus paracasei.*
8) The method of paragraph 1, wherein the probiotic is sensitive to lysozymes.
9) The method of paragraph 1, wherein the probiotic is *Lactococcus lactis* or a probiotic with a 16S rRNA sequence comprising at least 90% sequence identity to a 16S rRNA sequence from *Lactococcus lactis.*
10) A method for treating damage induced by SD, the method comprising: administering to an individual who is sleep deprived an agent that reduces reactive oxygen species.
11) The method of paragraph 10, wherein the damage occurs at a site selected from the group consisting of: brain, gastrointestinal tract, mouth, throat, lungs, heart, liver, gut, stomach, kidney, skin, bones, large intestine, small intestine, bladder, and muscular system.
12) The method of paragraph 10, wherein the damage occurs in the gut.
13) The method of paragraph 10, wherein SD is chronic or acute.
14) The method of paragraph 10, wherein the agent is selected from the group consisting of: a compound, a small molecule, a food additive, and an enzyme.
15) The method of paragraph 10, wherein the agent is synthetic.
16) The method of paragraph 10, wherein the agent is naturally occurring.
17) The method of paragraph 14, wherein the compound is selected from the group consisting of: Tyrosol, Quercetin, N-Acetyl Cysteine (NAC), Metformin, Catechin, 4-phenylbutyrate (PBA), Melatonin, Ursodeoxycholic acid, Nordihydroguaiaretic acid (NDGA), Coenzyme Q10 (ubiquinone), Vitamin E, Vitamin C, lipoic acid, and β-carotene.
18) The method of paragraph 14, wherein the small molecule is 4-phenylbutyrate (PBA).
19) The method of paragraph 14, wherein the food additive is selected from the group consisting of: Ascorbic acid, Sodium ascorbate, Calcium ascorbate, Fatty acid esters of ascorbic acid, Tocopherols, Alpha-tocopherol, Gamma-tocopherol, Delta-tocopherol, Propyl gallate, Octyl gallate, Dodecyl gallate, Erythorbic acid, Sodium erythorbate, Dodecyl gallate, Tertiary-butyl hydroquinone (TBHQ), Butylated hydroxyanisole (BHA), Butylated hydroxytoluene (BHT), Citric Acid, and 4-Hexylresorcinol.
20) The method of paragraph 14, wherein the enzyme is selected from the group consisting of: superoxide dismutase, thioredoxin reductase, glutathione reductase, glutathione peroxidase, and glutathione S-transferase.
21) A composition for treating or preventing damage induced by SD, the composition comprising: a probiotic that reduces reactive oxygen species and a sedative.
22) The composition of paragraph 21, wherein the probiotic expresses a superoxide dismutase polypeptide.
23) The composition of paragraph 22, wherein the superoxide dismutase polypeptide is a superoxide dismutase A (SodA) polypeptide.
24) The composition of paragraph 21, wherein the probiotic is selected from the group consisting of: *Streptococcus thermophilus, Lactobacillus casei, Lactococcus lactis,* and *Lactobacillus paracasei.*
25) The composition of paragraph 21, wherein the probiotic is *Lactococcus lactis* or a probiotic with a 16S rRNA sequence comprising at least 90% sequence identity to a 16S rRNA sequence from *Lactococcus lactis.*
26) The composition of paragraph 21, wherein the sedative is selected from a group consisting of: a barbiturate, a benzodiazepine, a non-benzodiazepine hypnotic, a methoaqualone, a first generation antihistamine, an antidepressant, an antipsychotics, an herbal sedative, alcohol, an opioid, a general anesthetic, a melatonin agonist, a orexin antagonists, and a skeletal muscle relaxant.

27) The composition of paragraph 21, wherein the composition further comprises a pharmaceutically acceptable carrier.
28) A composition for treating or preventing damage induced by SD, the composition comprising: an agent that reduces reactive oxygen species and a sedative.
29) The composition of paragraph 28, wherein the agent is selected from the group consisting of: a compound, a small molecule, a therapeutic, and a food additive.
30) The composition of paragraph 28, wherein the agent is synthetic.
31) The composition of paragraph 28, wherein the agent is naturally occurring.
32) The composition of paragraph 28, wherein the stimulant is selected from a group consisting of: an herbal stimulant, an amphetamine, a methamphetamine, cocaine, a methylxanthine, ephedrine, a cathinone, mephedrone, methylenedioxypyrovalerone, methylenedioxymethamphetamine, nicotine, propylhexedrine, and pseudoephedrine.
33) The composition of paragraph 28, wherein the compound is selected from the group consisting of: ascorbic acid, glutathione, lipoic acid, uric acid, carotene, alpha-tocopherol, and ubiquinol.
34) The composition of paragraph 28, wherein the small molecule is PBA.
35) The composition of paragraph 28, wherein the food additive is selected from the group consisting of: Ascorbic acid, Sodium ascorbate, Calcium ascorbate, Fatty acid esters of ascorbic acid, Tocopherols, Alpha-tocopherol, Gamma-tocopherol, Delta-tocopherol, Propyl gallate, Octyl gallate, Dodecyl gallate, Erythorbic acid, Sodium erythorbate, Dodecyl gallate, Tertiary-butyl hydroquinone (TBHQ), Butylated hydroxyanisole (BHA), Butylated hydroxytoluene (BHT), Citric Acid, and 4-Hexylresorcinol.
36) The composition of paragraph 28, wherein the enzyme is selected from the group consisting of: superoxide dismutase, thioredoxin reductase, glutathione reductase, glutathione peroxidase, and glutathione S-transferase.
37) The composition of paragraph 28, wherein the composition further comprises a pharmaceutically acceptable carrier.
38) A composition for treating or preventing damage induced by SD, the composition comprising: a probiotic that reduces reactive oxygen species and a stimulant.
39) The composition of paragraph 38, wherein the probiotic expresses a superoxide dismutase polypeptide.
40) The composition of paragraph 39, wherein the superoxide dismutase polypeptide is a superoxide dismutase A (SodA) polypeptide.
41) The composition of paragraph 38, wherein the probiotic is selected from the group consisting of: *Streptococcus thermophilus, Lactobacillus casei, Lactococcus lactis*, and *Lactobacillus paracasei*.
42) The composition of paragraph 38, wherein the probiotic is *Lactococcus lactis* or a probiotic with a 16S rRNA sequence comprising at least 90% sequence identity to a 16S rRNA sequence from *Lactococcus lactis*.
43) The composition of paragraph 38, wherein the stimulant is selected from a group consisting of: an herbal stimulant, an amphetamine, a methamphetamine, cocaine, a methylxanthine, ephedrine, a cathinone, mephedrone, methylenedioxypyrovalerone, methylenedioxymethamphetamine, nicotine, propylhexedrine, and pseudoephedrine.
44) The composition of paragraph 38, wherein the composition further comprises a pharmaceutically acceptable carrier.
45) A composition for treating or preventing damage induced by SD, the composition comprising: an agent that reduces reactive oxygen species and a stimulant.
46) The composition of paragraph 45, wherein the agent is selected from the group consisting of: a compound, a small molecule, a therapeutic, and a food additive.
47) The composition of paragraph 45, wherein the agent is synthetic.
48) The composition of paragraph 45, wherein the agent is naturally occurring.
49) The composition of paragraph 45, wherein the stimulant is selected from a group consisting of: an herbal stimulant, an amphetamine, a methamphetamine, cocaine, a methylxanthine, ephedrine, a cathinone, mephedrone, methylenedioxypyrovalerone, methylenedioxymethamphetamine, nicotine, propylhexedrine, and pseudoephedrine.
50) The composition of paragraph 45, wherein the compound is selected from the group consisting of: ascorbic acid, glutathione, lipoic acid, uric acid, carotene, alpha-tocopherol, and ubiquinol.
51) The composition of paragraph 45, wherein the small molecule is PBA.
52) The composition of paragraph 45, wherein the food additive is selected from the group consisting of: Ascorbic acid, Sodium ascorbate, Calcium ascorbate, Fatty acid esters of ascorbic acid, Tocopherols, Alpha-tocopherol, Gamma-tocopherol, Delta-tocopherol, Propyl gallate, Octyl gallate, Dodecyl gallate, Erythorbic acid, Sodium erythorbate, Dodecyl gallate, Tertiary-butyl hydroquinone (TBHQ), Butylated hydroxyanisole (BHA), Butylated hydroxytoluene (BHT), Citric Acid, and 4-Hexylresorcinol.
53) The composition of paragraph 45, wherein the enzyme is selected from the group consisting of: superoxide dismutase, thioredoxin reductase, glutathione reductase, glutathione peroxidase, and glutathione S-transferase
54) The composition of paragraph 45, wherein the composition further comprises a pharmaceutically acceptable carrier.
55) A method for treating or preventing damage induced by SD, the method comprising: administering to an individual who is sleep deprived a composition of any one of paragraphs 21 to 54.

EXAMPLES

When we don't sleep enough, we feel it. The brain is likely making us sleepy in order to prevent disastrous consequences of sleep loss. Perhaps it's OK to skip one night of sleep. But how about two? Or three? At some point, no amount of coffee or good will is enough to compensate for healthy sleep. Up to 15% of the United States population suffers from chronic insomnia[1]. Sleep disturbance leads to myriad health problems including impaired performance in motor and cognitive tasks, memory loss and mood disorders[2], with chronic sleep deprivation causing or aggravating conditions such as heart disease, diabetes, depression and cancer[3,4]. The behavioral hallmarks of sleep[5,6], and its molecular basis[7], are highly conserved from flies to humans.

This, combined with the fact that the fly brain consists of only ~100,000 neurons, and that there are multiple tools for manipulating fly genes and neural circuits, makes this animal a good system in which to study sleep.

Example 1

The effects of sleep deprivation on health and longevity were investigated. Experimental setup: No systematic approaches have been taken in any organism to look for changes induced by long-term sleep deprivation (SD). Studying the effects of SD in mammals is complicated by ethics and long natural lifespan. Fortunately, multiple studies showed that short-sleeping flies don't live as long as flies that sleep ad libitum (e.g.[8-10]).

First a reproducible, high-throughput assay for SD was established. Mechanical stimulation was ruled out because it was noticed that even mild mechanical stimuli can induce stress in flies, even when applied during waking hours. Instead, thermogenetic approaches to SD were used. Multiple Gal4 lines which, when used to activate neurons, were used and result in decreased sleep. These lines can be separated into different categories, based on the severity of sleep loss they cause. To activate neurons, Gal4 transgenic flies to were crossed with UAS-TrpA1 transgenic flies. TrpA1 is a heat-sensitive cation channel that is activated by temperatures above 28° C.[11].

Figure 2:
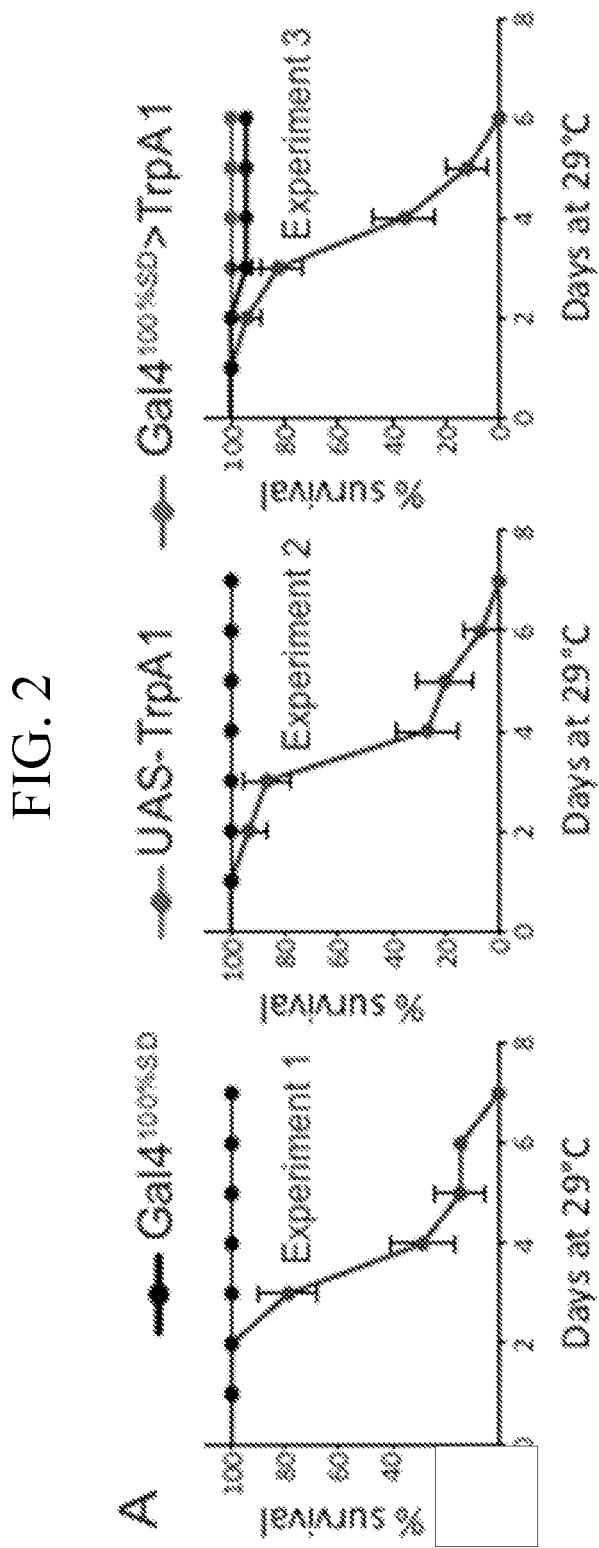
FIG. 2 shows that the effect on survival with strong SD using the GAL4/UAS system to express TrpA1 is reproducible.

Results: Using Gal4 lines that cause strong ($Gal4^S$), intermediate ($Gal4^I$) or mild ($Gal4^M$) SD, the amount of sleep loss correlates with longevity was assessed. The following was observed: First, the effect of each Gal4 line on lifespan is reproducible across multiple experiments (FIGS. 1 and 2). This is important in looking for modifiers of survival after SD.

For each category (S, I, M), multiple non-overlapping Gal4s exist, and all produce similar survival phenotypes. This is important for making sure that it is the loss of sleep, and not the activation of a particular set of neurons, that has negative consequences on health.

Figure 4:
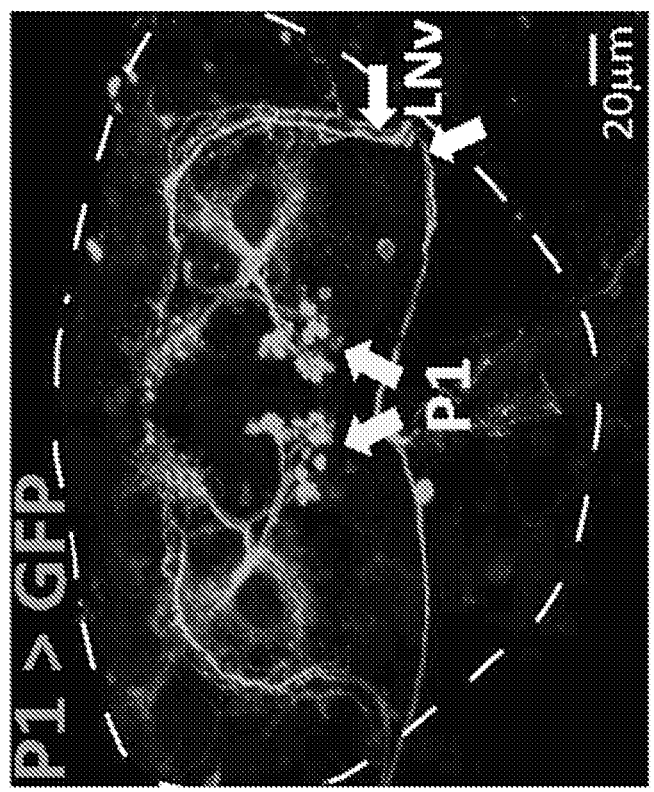
FIG. 4 shows sparse expression of P1-Gal4 (a strong GAL4). Yellow arrows: P1 cell bodies. White arrows: projections from circadian clock neurons LNv. White dashes circumscribe the central brain.

Having established these principles, a $Gal4^S$ line was chosen to focus on. This line is expressed sparsely, mainly in the P1 courtship neurons (FIG. 4). A published study on sexual satiety noticed that males have trouble sleeping when P1 neurons are activated. This line is also expressed in LNvs, a well-known set of circadian clock neurons (FIG. 4, white arrows), but LNvs were ruled out as being responsible for SD for two reasons. First, introduction of a Gal4 inhibitor Gal80 into these clock cells has no consequence on the SD phenotype produced by P1-Gal4. Second, using LNv-Gal4 to activate only LNvs causes no SD. Instead, it is P1 activation that is arousing: when they are activated, males are hypersexual[12]. If no females are present, they court their own reflection, or even inanimate objects. Therefore, sleep deprivation here is a consequence of an excessively aroused brain.

Figure 5:
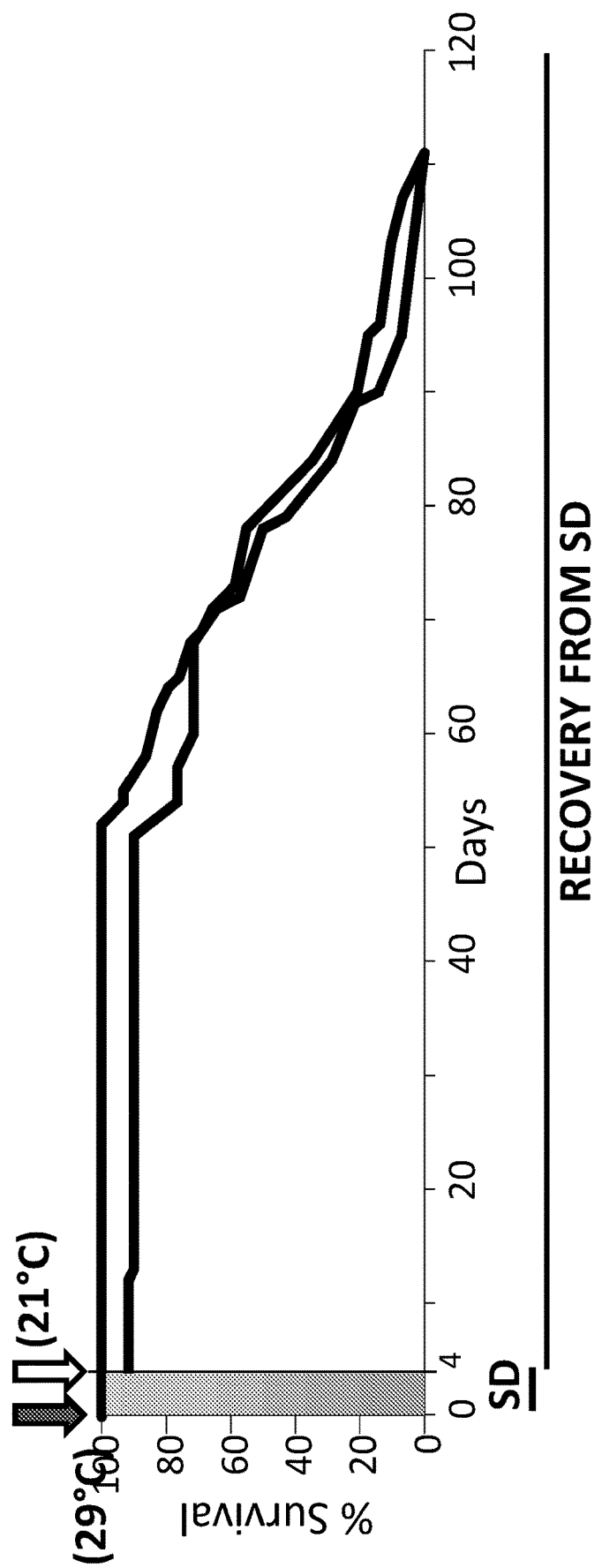
FIG. 5 shows that the effect of SD on survival is reversible to some degree.
Figure 6C:
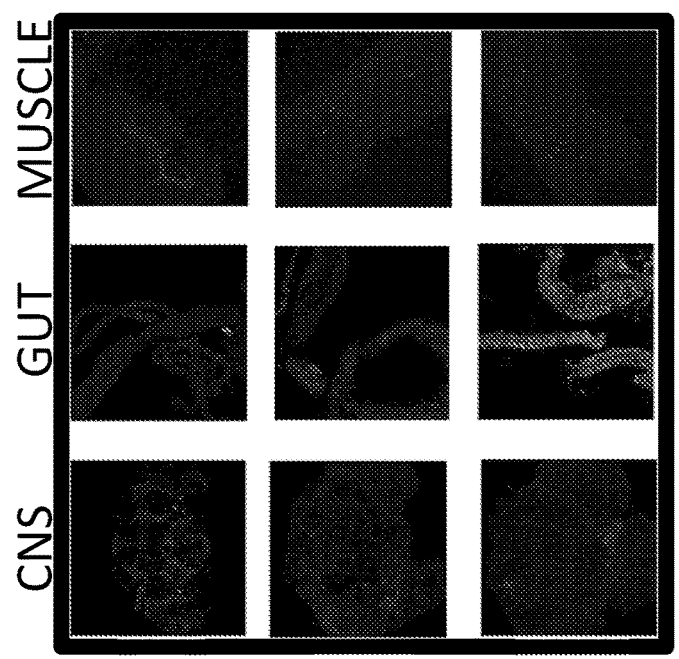
FIG. 6A-6C show reactive oxygen species levels after strong SD (100% SD).
Figure 6A:
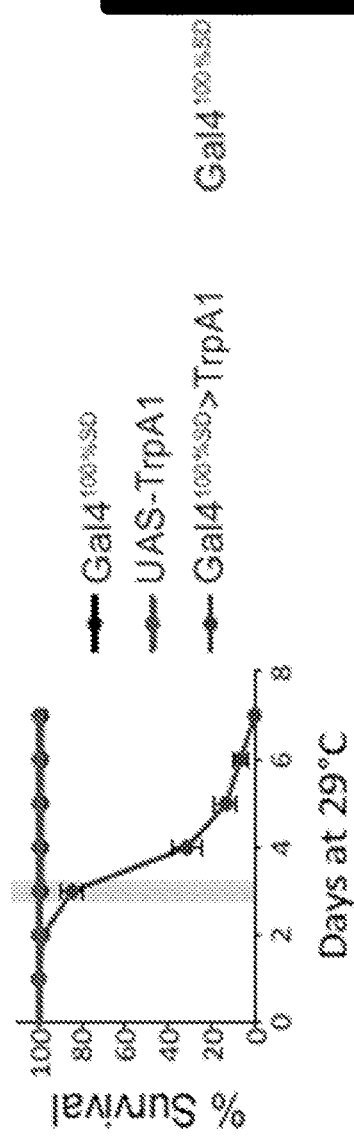
Figure 6B:
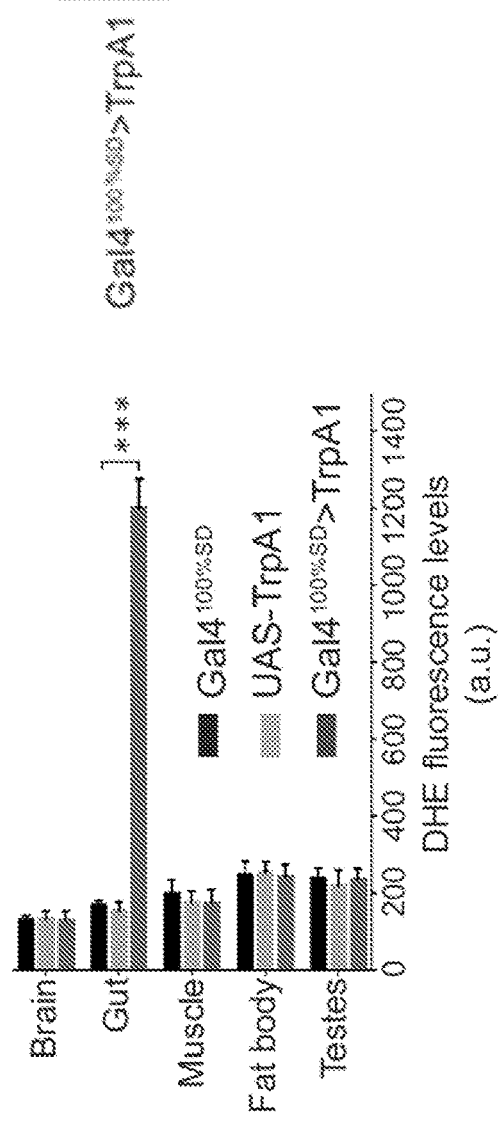
Figure 7C:
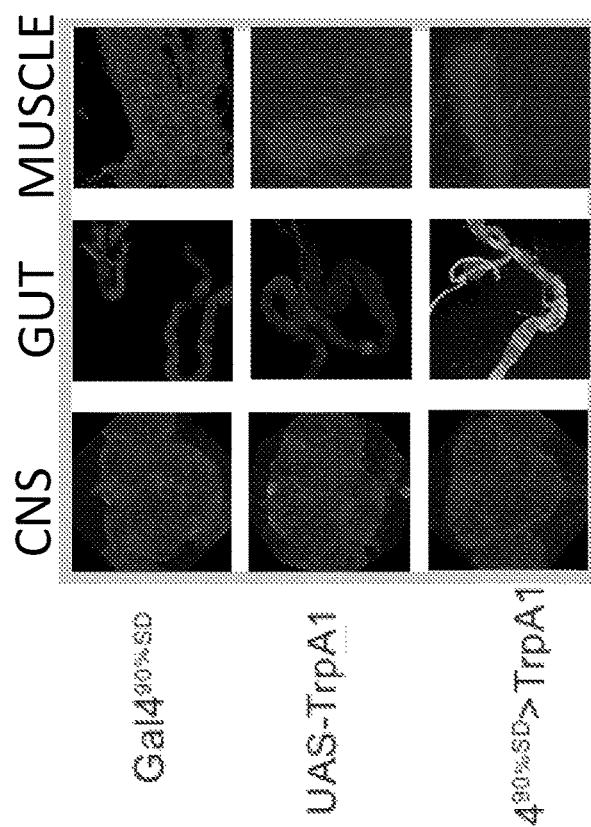
FIG. 7A-7C show reactive oxygen species levels after intermediate SD (90% SD).
Figure 7A:
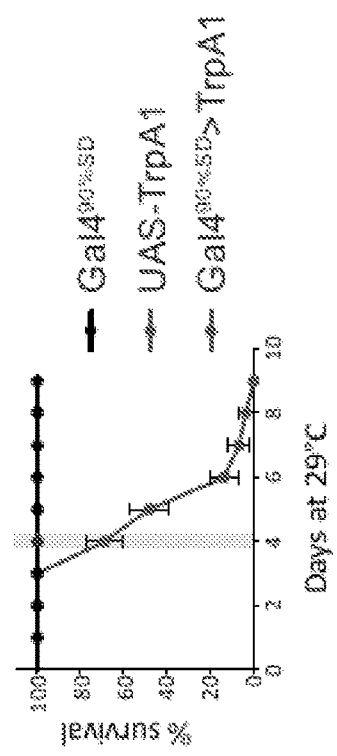
Figure 7B:
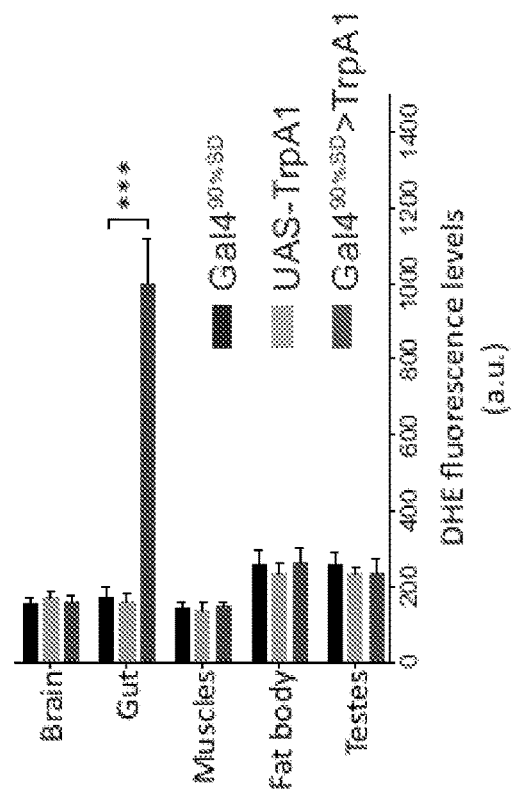

The effect of SD can be reversible: It was determine if flies that are on the verge of dying as a consequence of SD can return to the normal lifespan trajectory if SD is stopped. When P1 neurons are activated (P1>TrpA1, 29° C.), flies die by day 6-7. Before they die, they lay down and stop moving (but move in response to gentle prodding). We placed such animals at 21° C., to stop deprivation. We were shocked to see that they quickly bounce back and catch up to the controls in terms of their lifespan (FIG. 5). This suggests that SD-induced damage can be reversible, at least to a point. Continued SD after a short break resulted in flies dying extremely quickly-indicating that previous SD is remembered, at least for a while.

Figure 3:
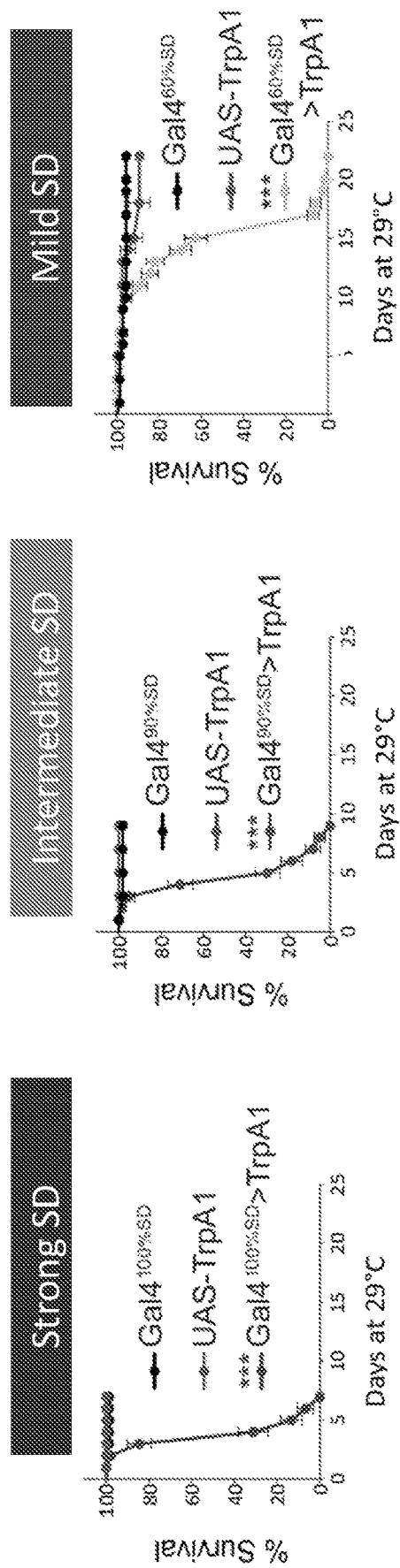
FIG. 3 shows that survival of the animal negatively correlates with the extent of SD. Strong SD is 100% SD; Intermediate SD is 90% SD, Mild SD is 60% SD.
Figure 8:
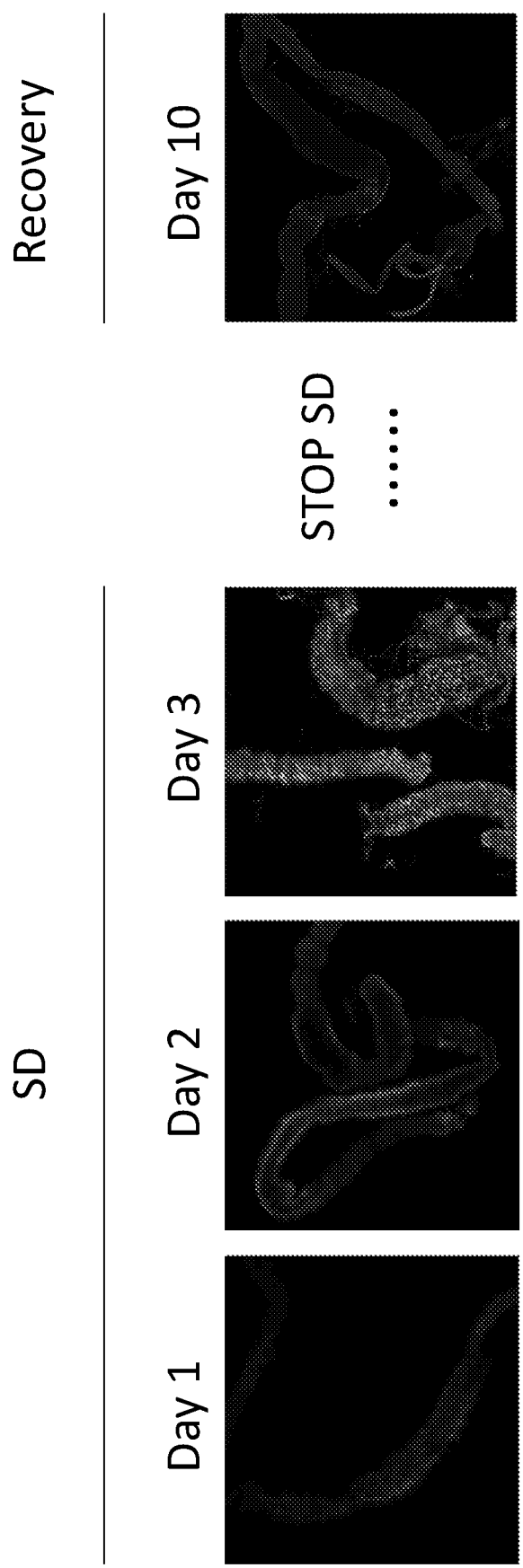
FIG. 8 shows that increased reactive oxygen species levels are decreased upon stopping SD.
Figure 9:
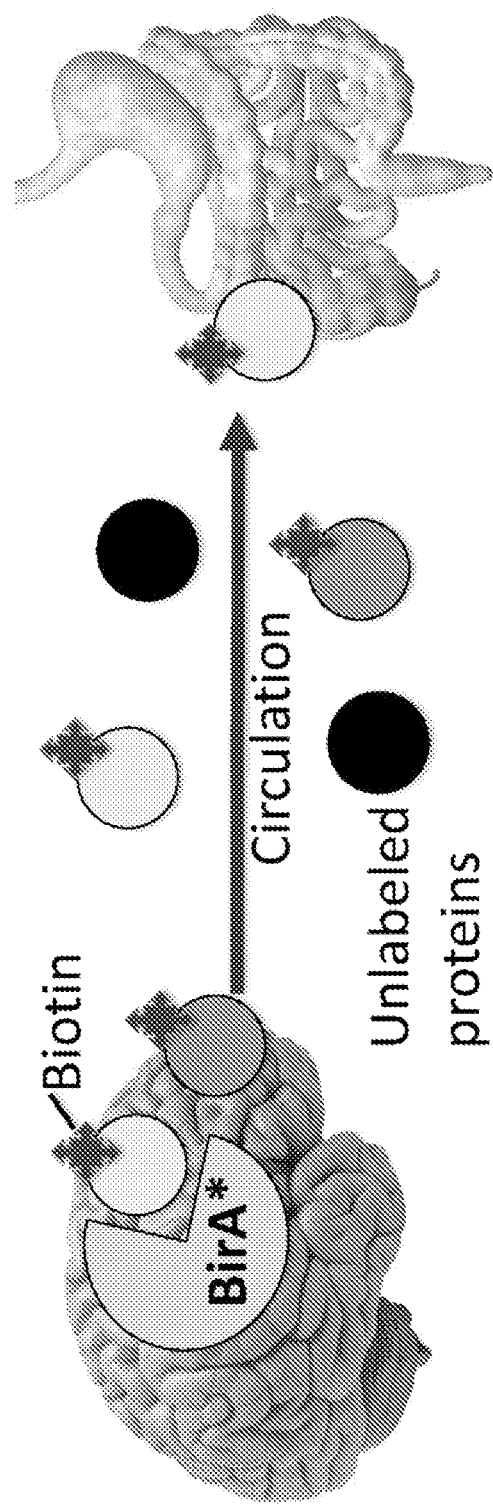
FIG. 9 shows a method for assessing inter-organ communication.
Figure 10:
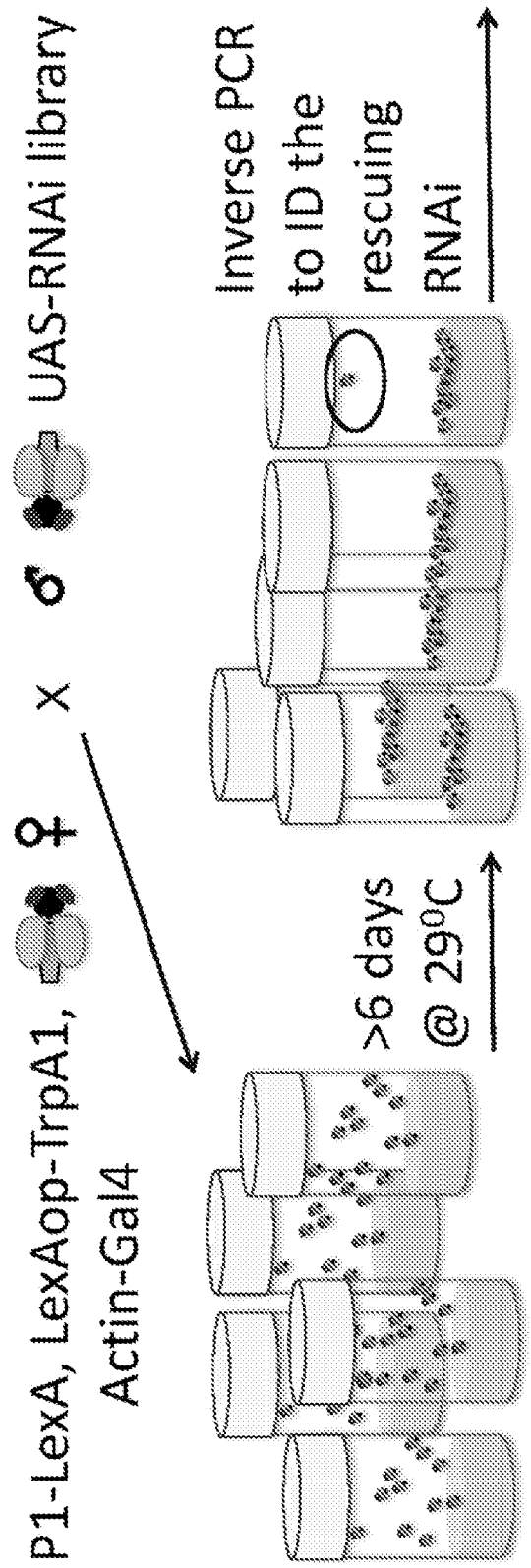
FIG. 10 shows a high-throughput approach for identifying modifies of SD-induced lethality.
Figure 11:
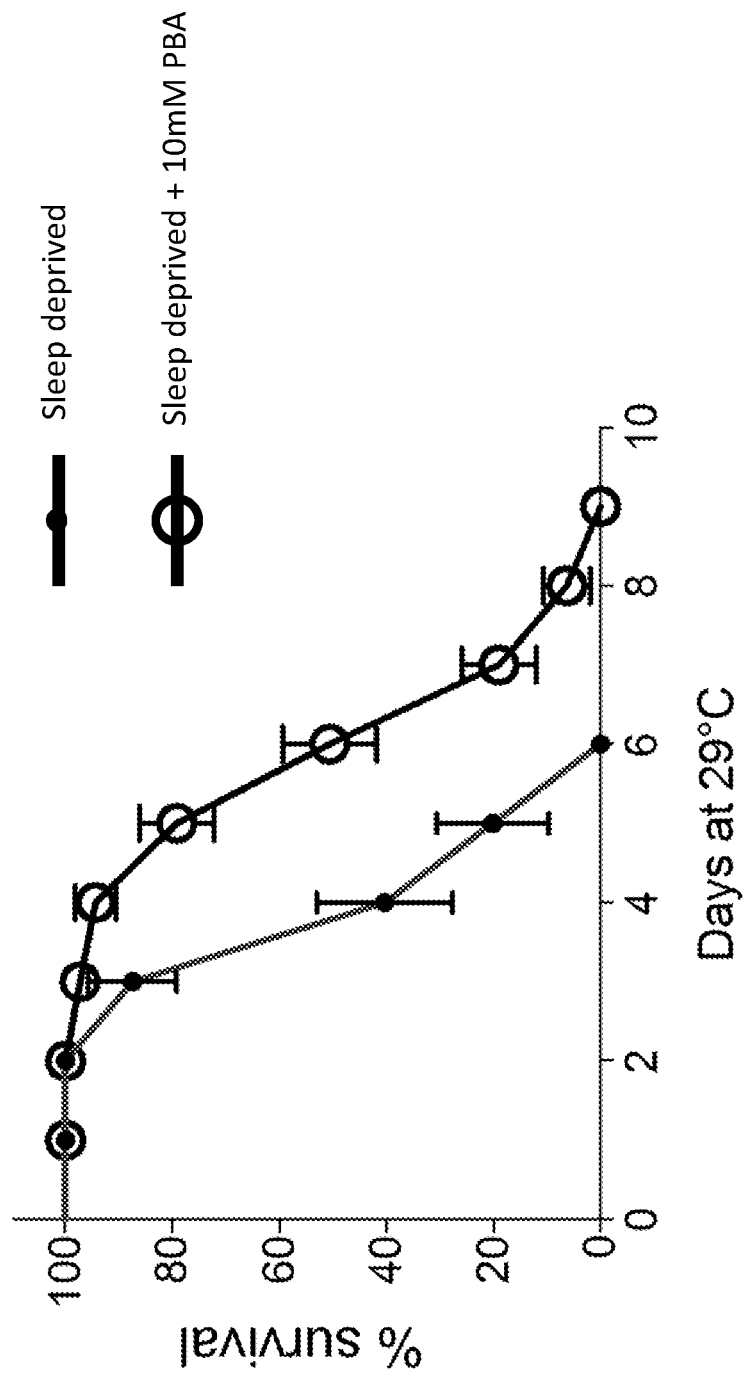
FIG. 11 shows the anti-reactive oxygen species drug 4-phenylbutyrate (PBA) extends survival of the animal following SD.
Figure 12:
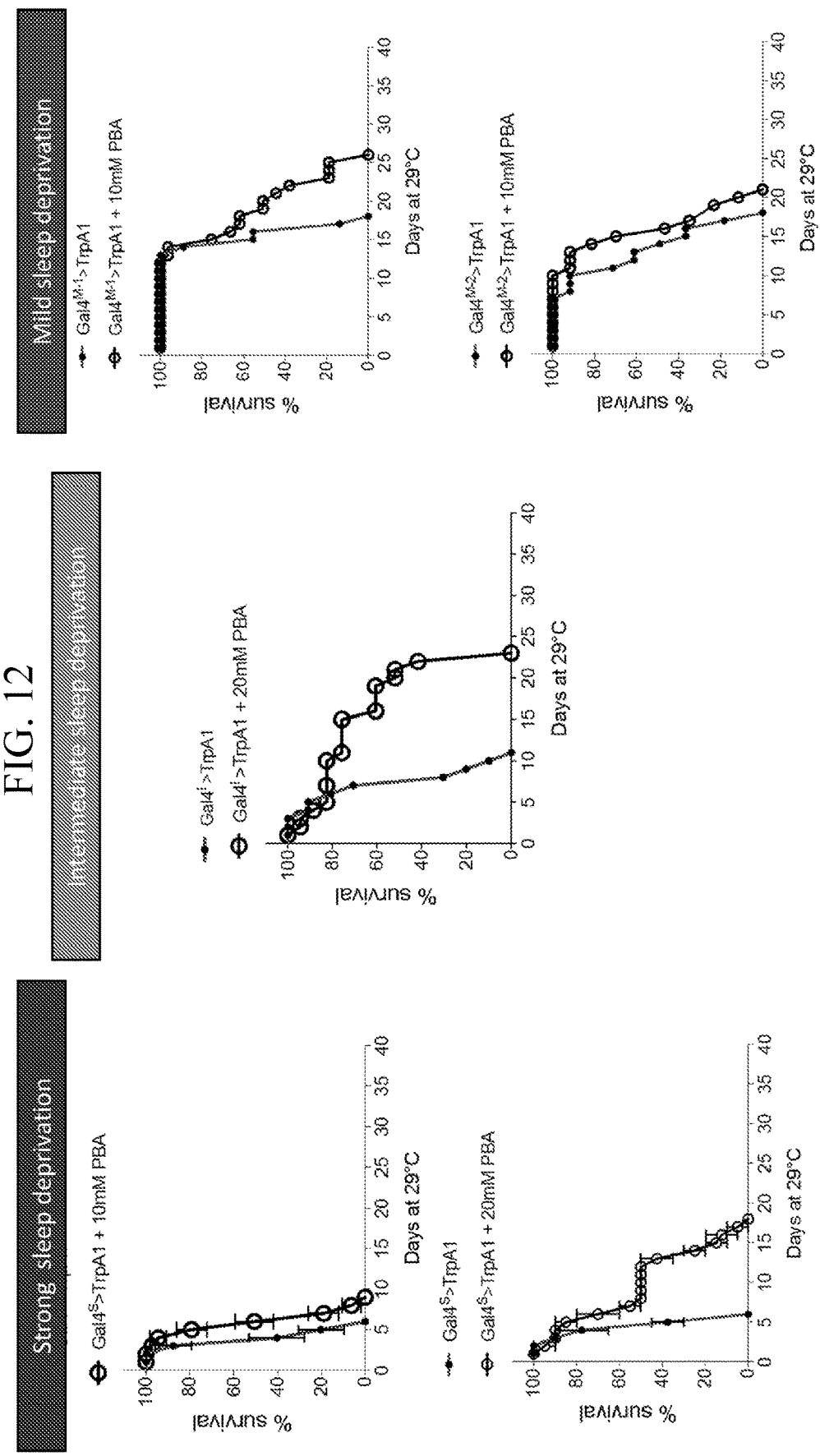
FIG. 12 shows the survival of a strongly sleep deprived (left), an intermediately sleep deprived (middle), and mildly sleep deprived (right) animal following administering 4-Phenylbutyrate (PBA).
Figure 13:
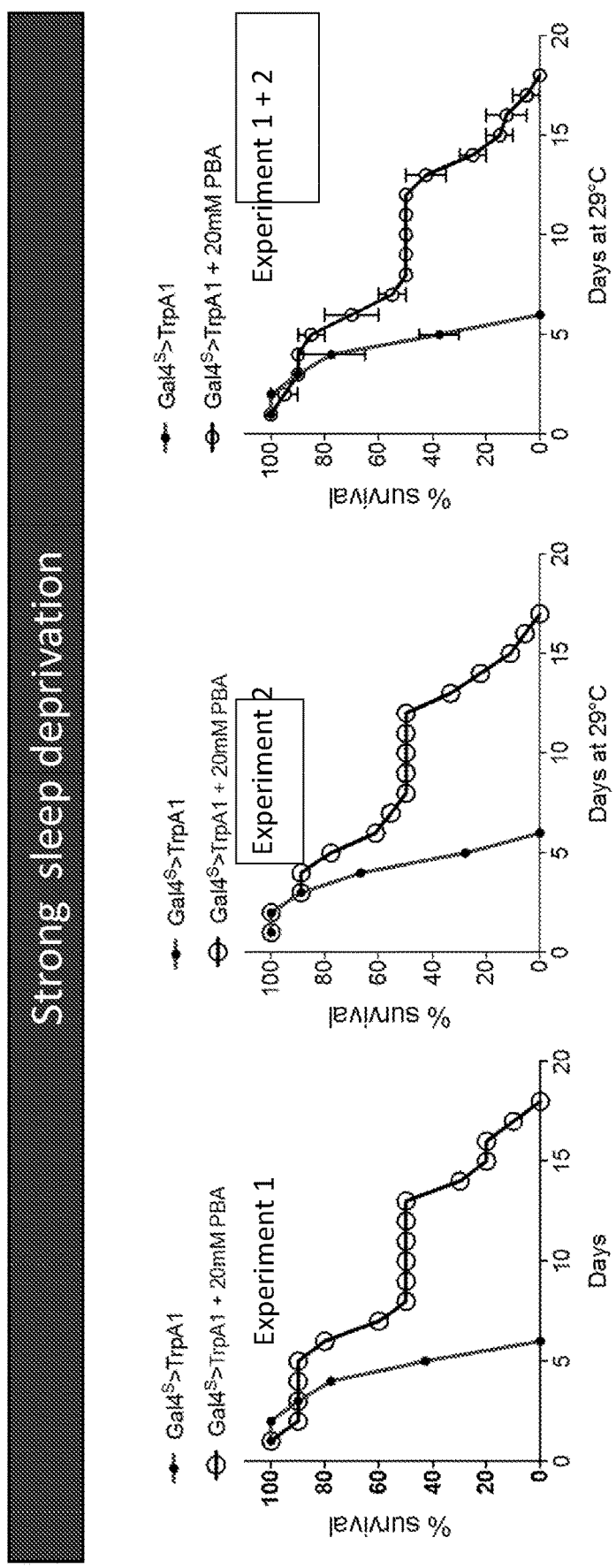
FIG. 13 shows the survival of a strongly sleep deprived animal following administering 4-Phenylbutyrate (PBA).
Figure 14:
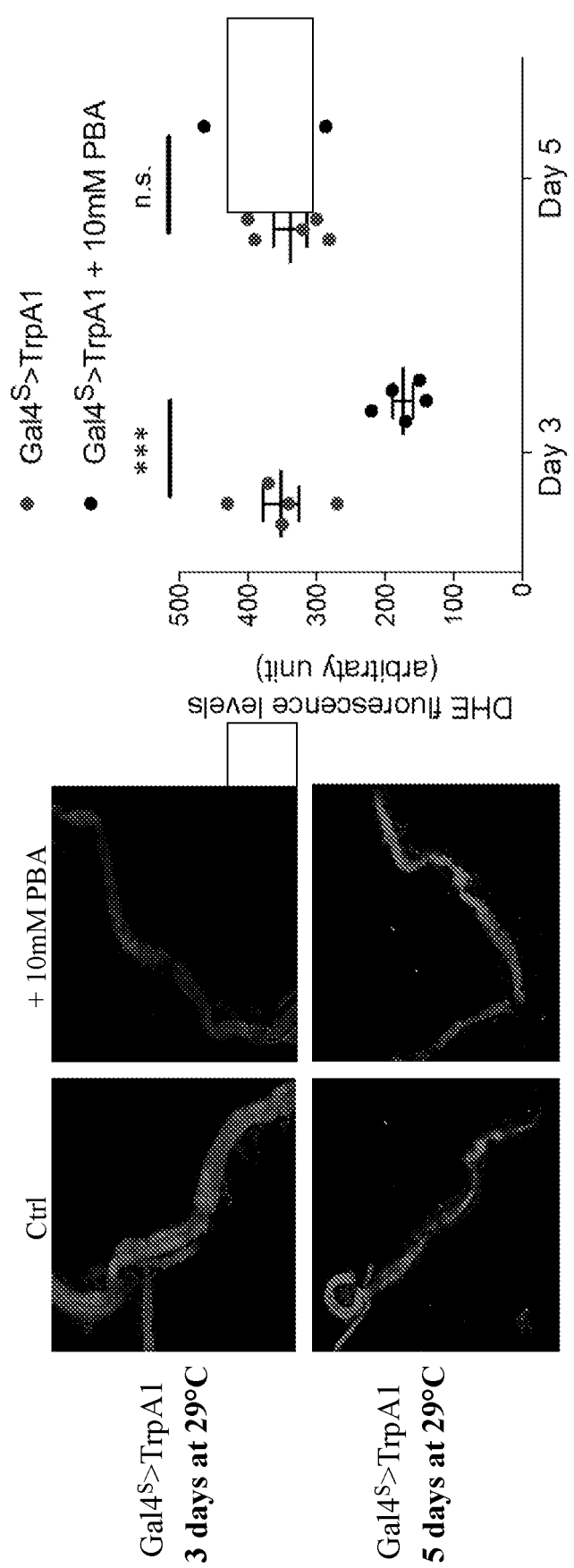
FIG. 14 shows reactive oxygen species levels following administering 10 mM PBA for 3 and 5 days.
Figure 15:
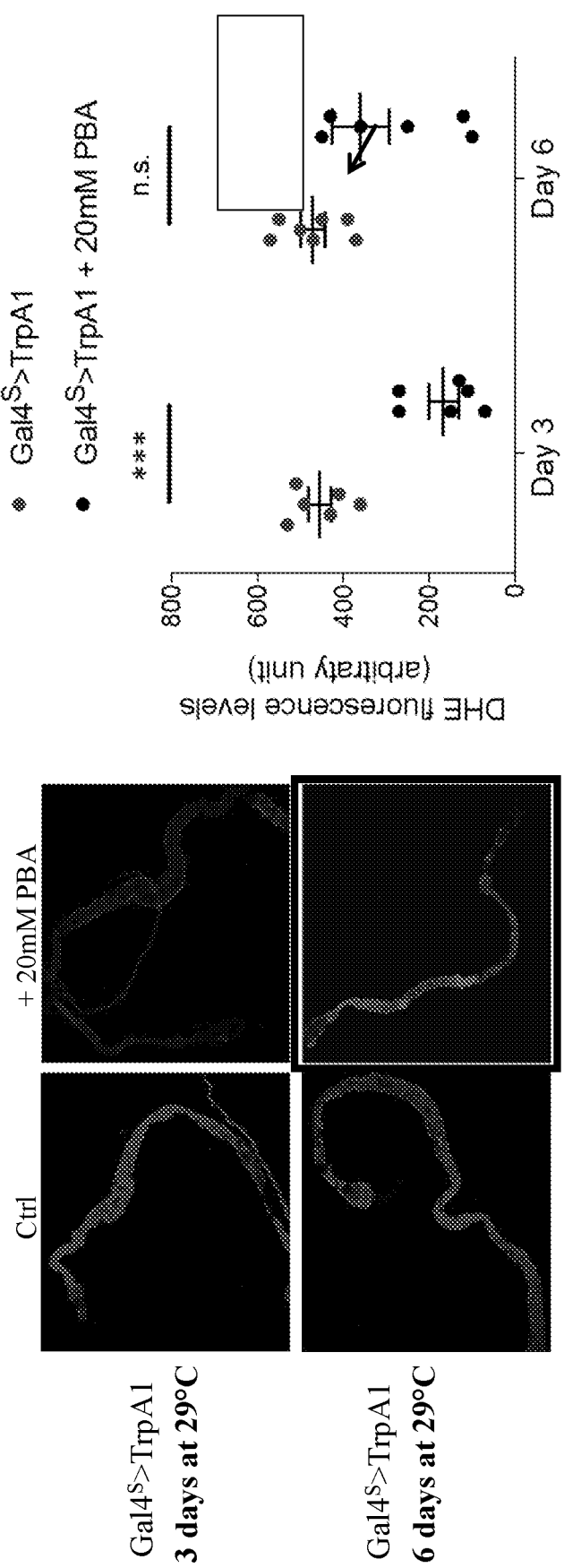
FIG. 15 shows reactive oxygen species levels following administering 20 mM PBA for 3 and 7 days.
Figure 16:
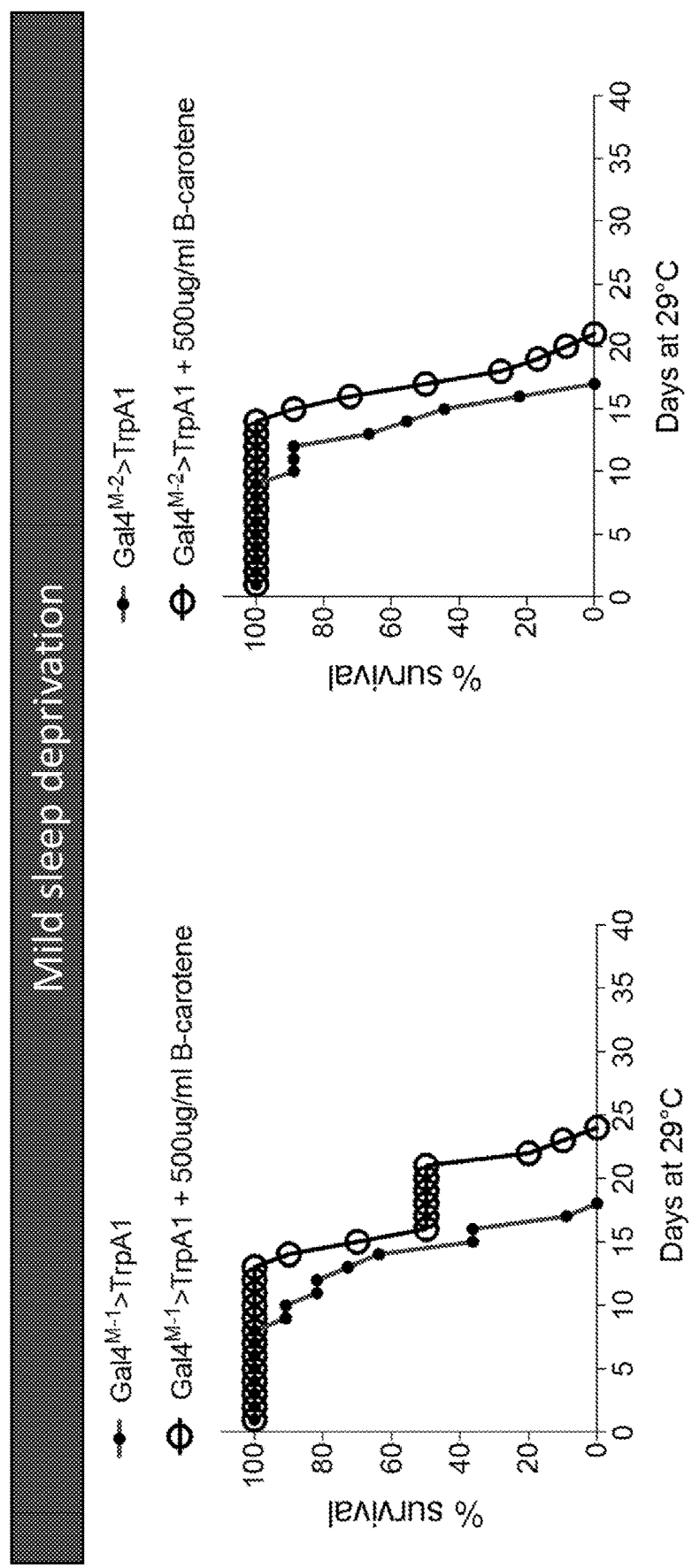
FIG. 16 shows the survival of a mildly sleep deprived animal following administering β-Carotene.
Figure 17:
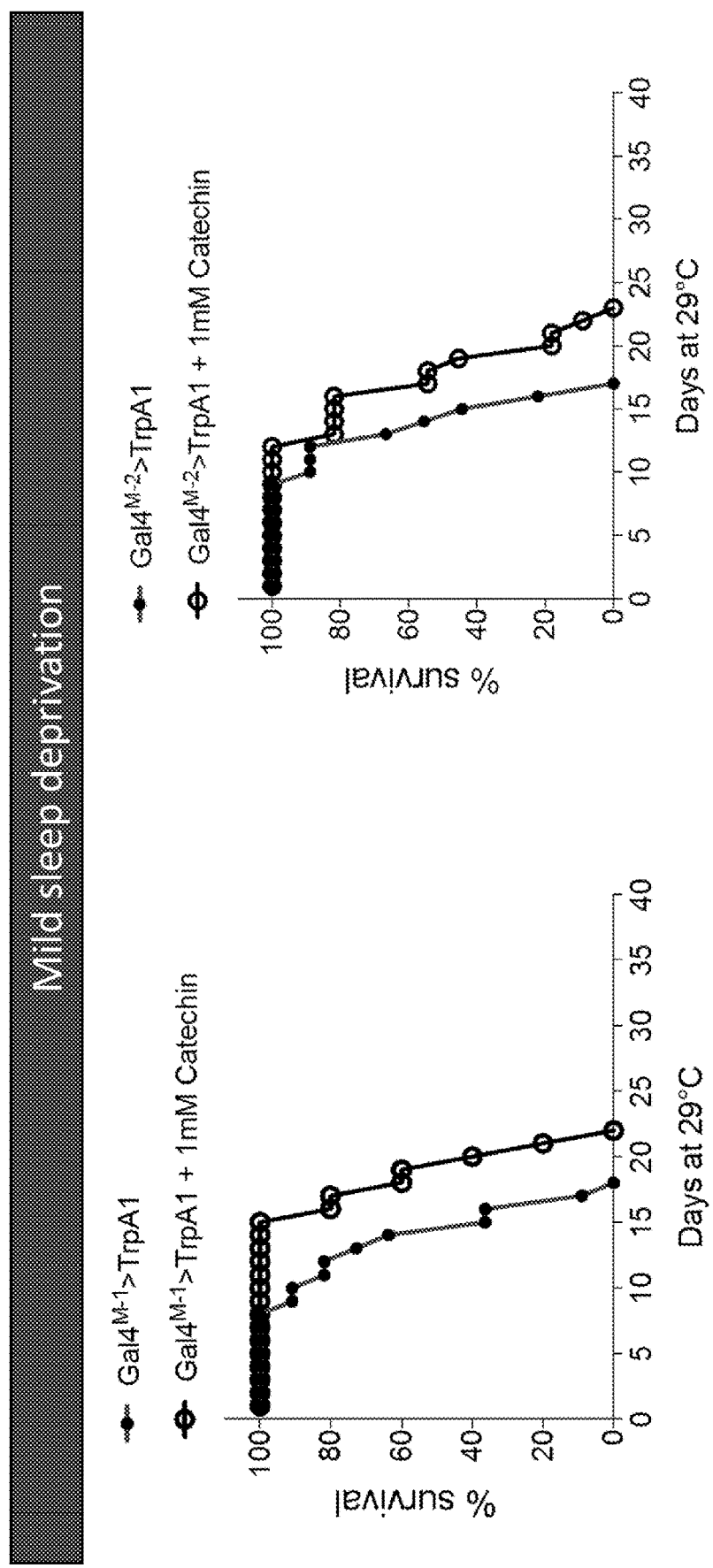
FIG. 17 shows the survival of a mildly sleep deprived animal following administering Catechin.
Figure 18:
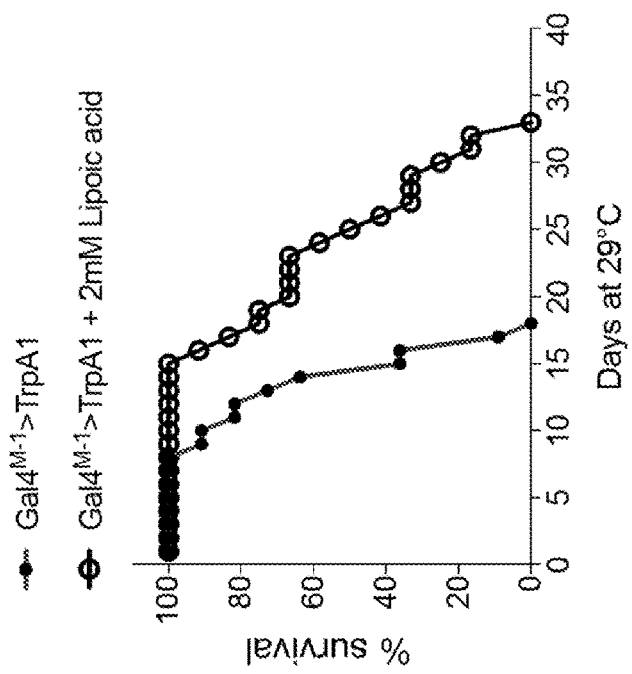
FIG. 18 shows the survival of a mildly sleep deprived animal following administering Lipoic acid.
Figure 19:
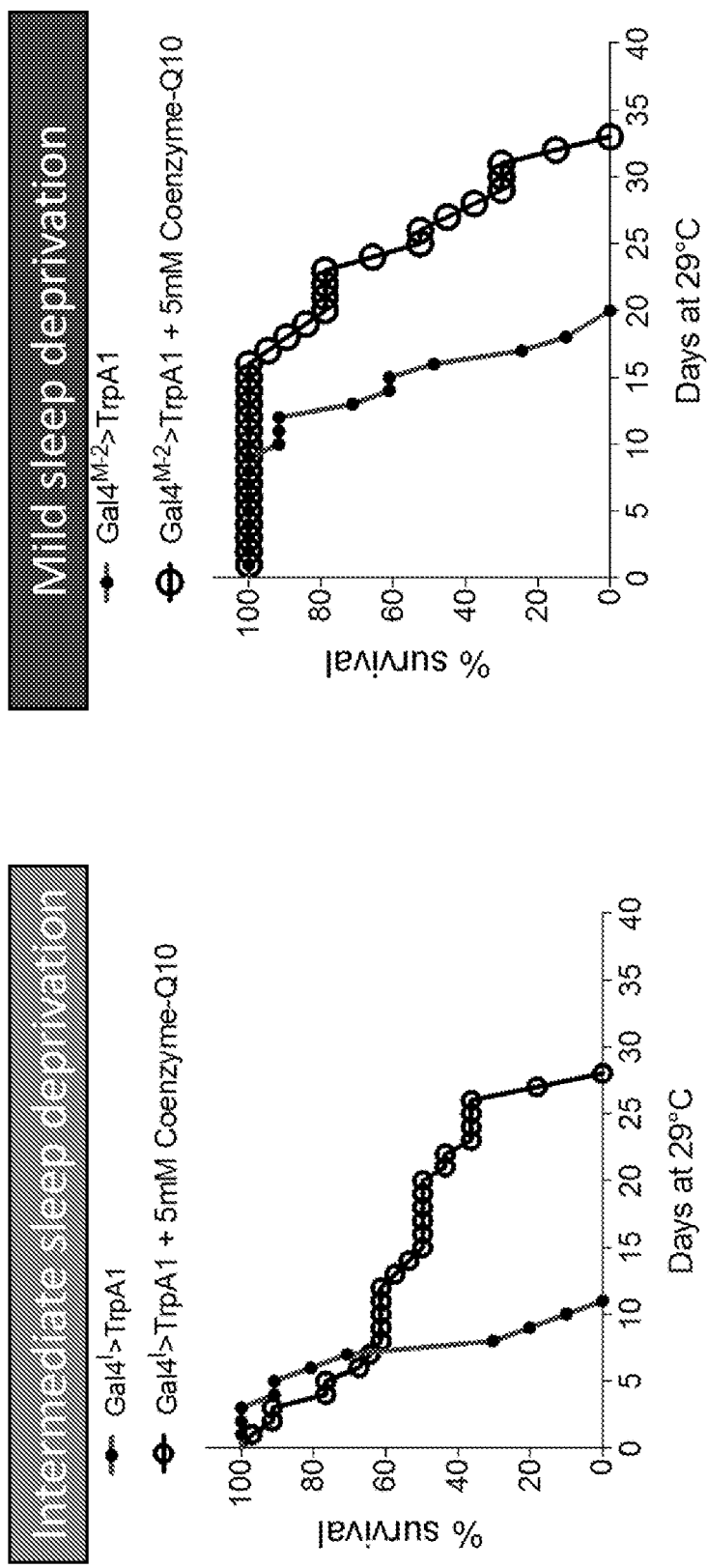
FIG. 19 shows the survival of an intermediately sleep deprived (left) and mildly sleep deprived (right) animal following administering Coenzyme Q10 (ubiquinone).
Figure 20:
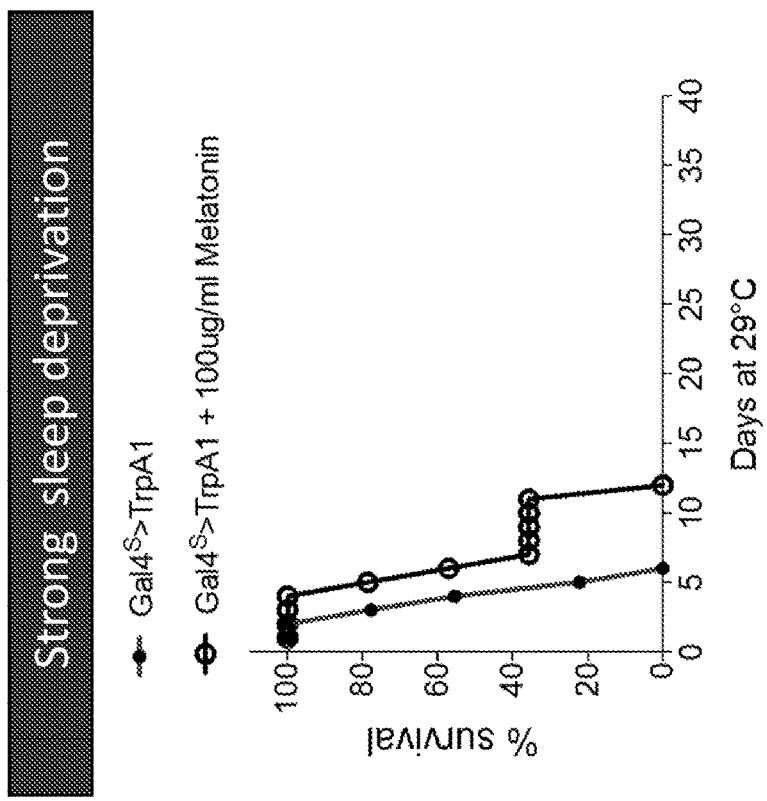
FIG. 20 shows the survival of a strongly sleep deprived (left) and mildly sleep deprived (right) animal following administering melatonin.
Figure 21:
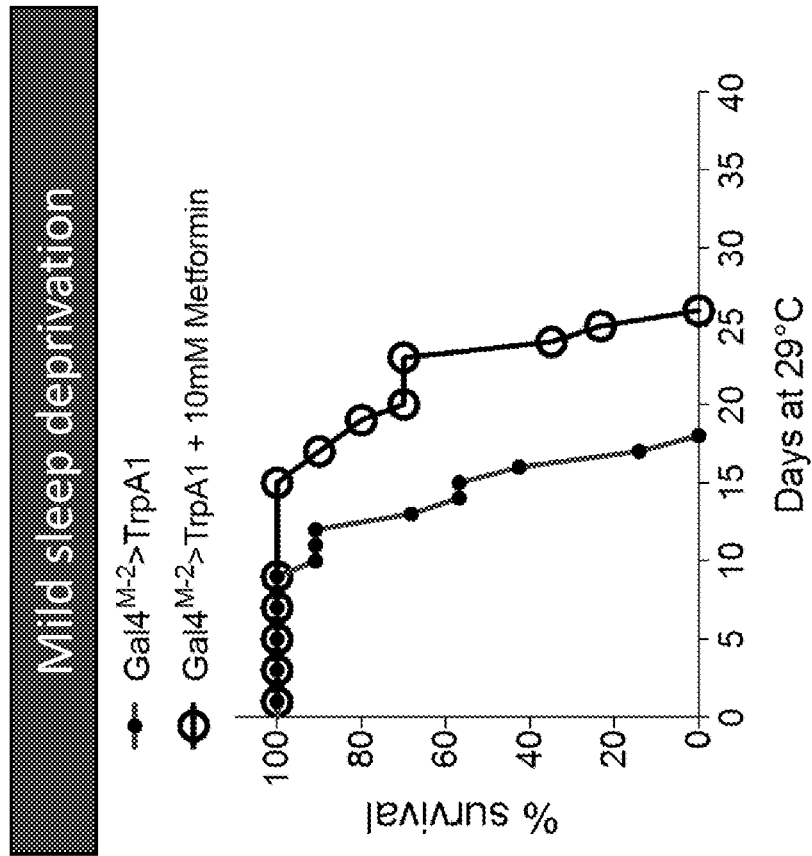
FIG. 21 shows the survival of a mildly sleep deprived animal following administering metformin.
Figure 22:
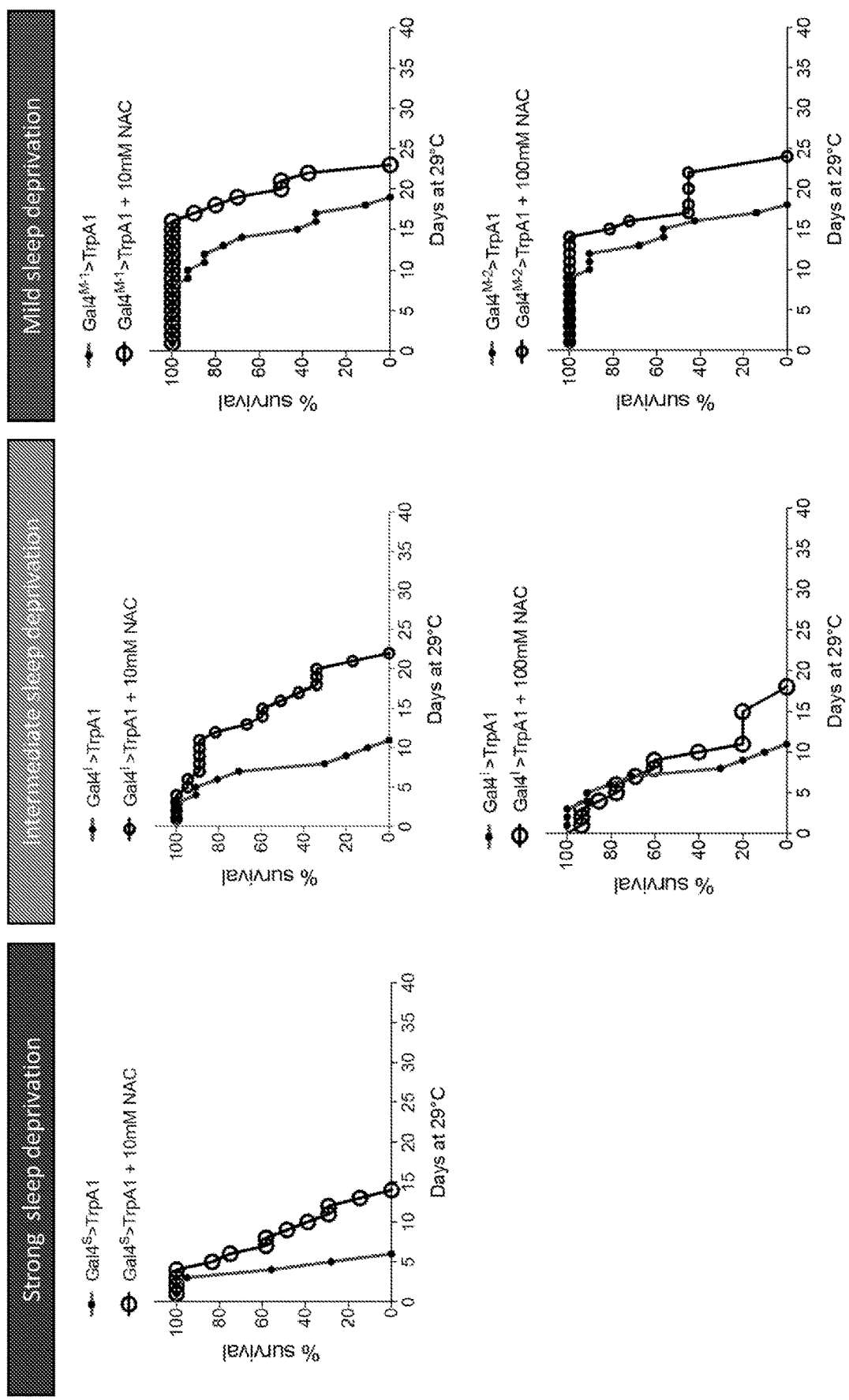
FIG. 22 shows the survival of a strongly sleep deprived (left), an intermediately sleep deprived (middle), and mildly sleep deprived (right) animal following administering N-acetyl Cysteine (NAC).
Figure 23:
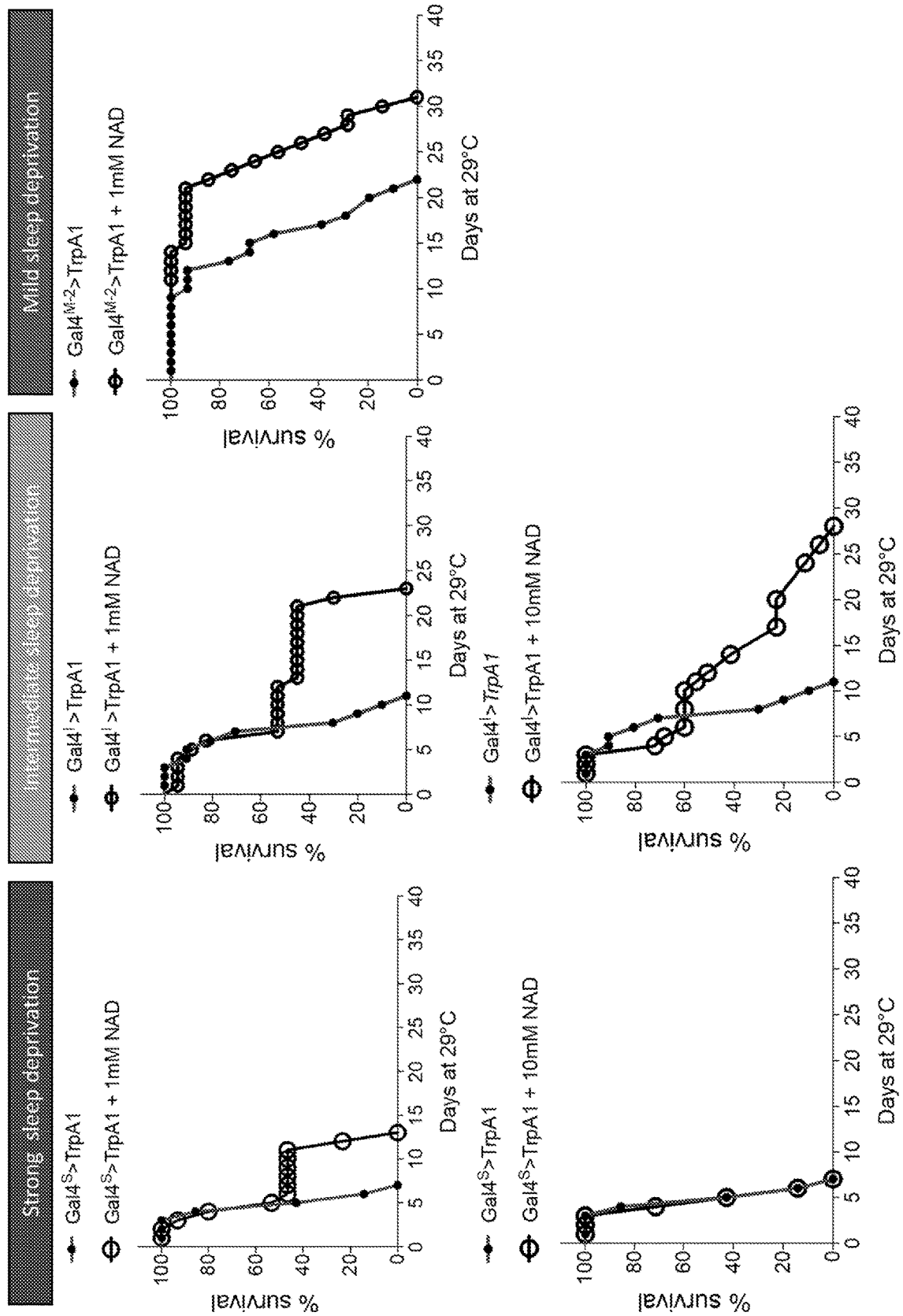
FIG. 23 shows the survival of a strongly sleep deprived (left), an intermediately sleep deprived (middle), and mildly sleep deprived (right) animal following administering Nicotinamide-adenine dinucleotide (NAD).
Figure 24:
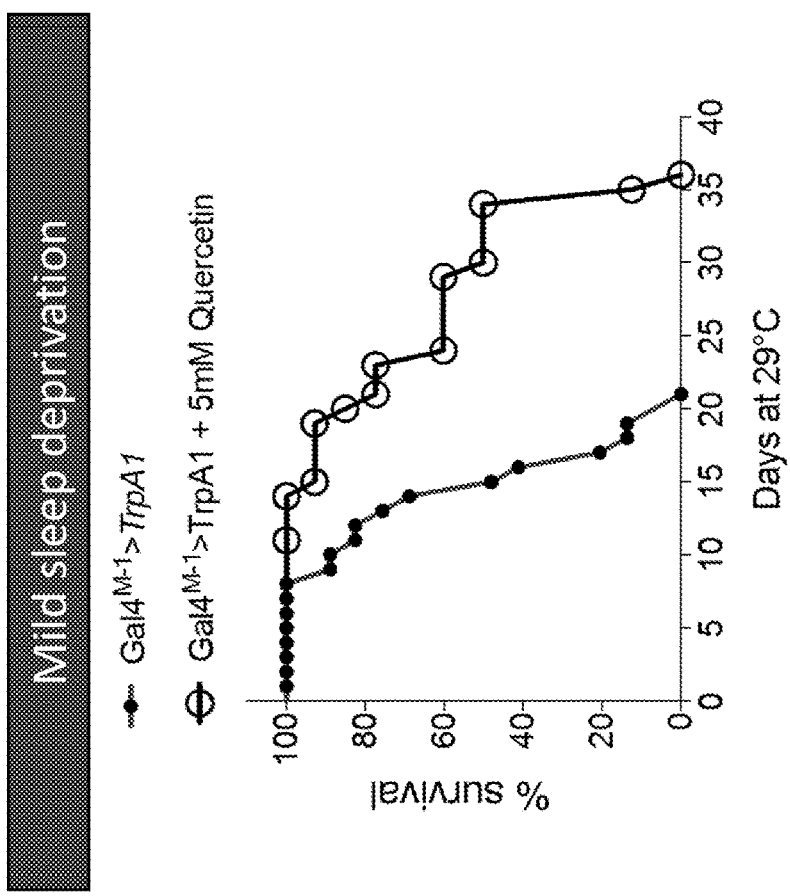
FIG. 24 shows survival of mildly sleep-deprived animals following administering Nordihydroguaiaretic acid (NDGA).
Figure 25:
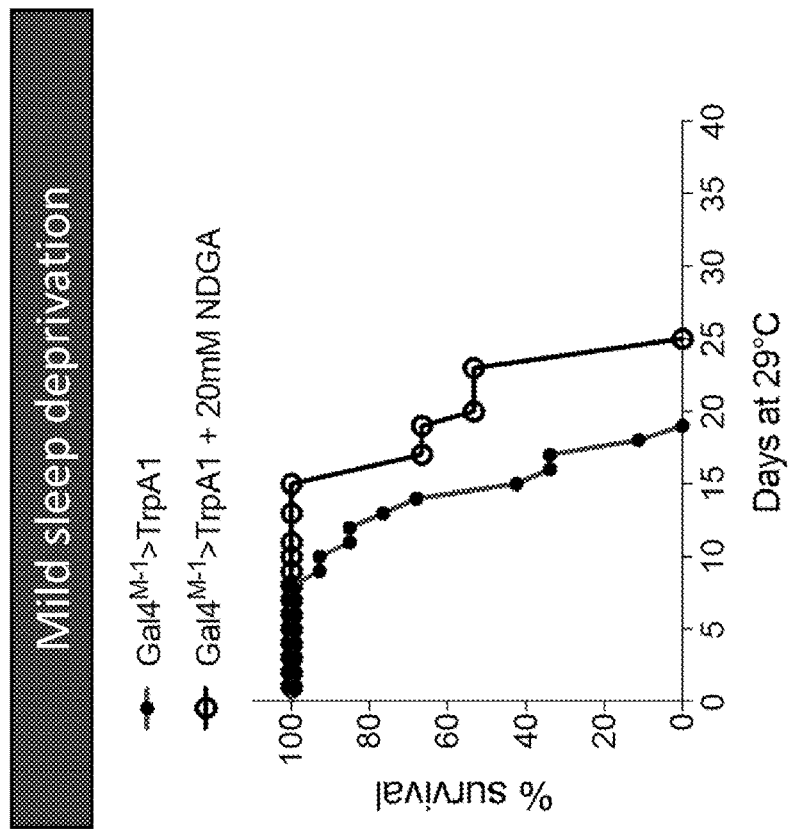
FIG. 25 shows the survival of a mildly sleep deprived animal following administering Quercetin.
Figure 26:
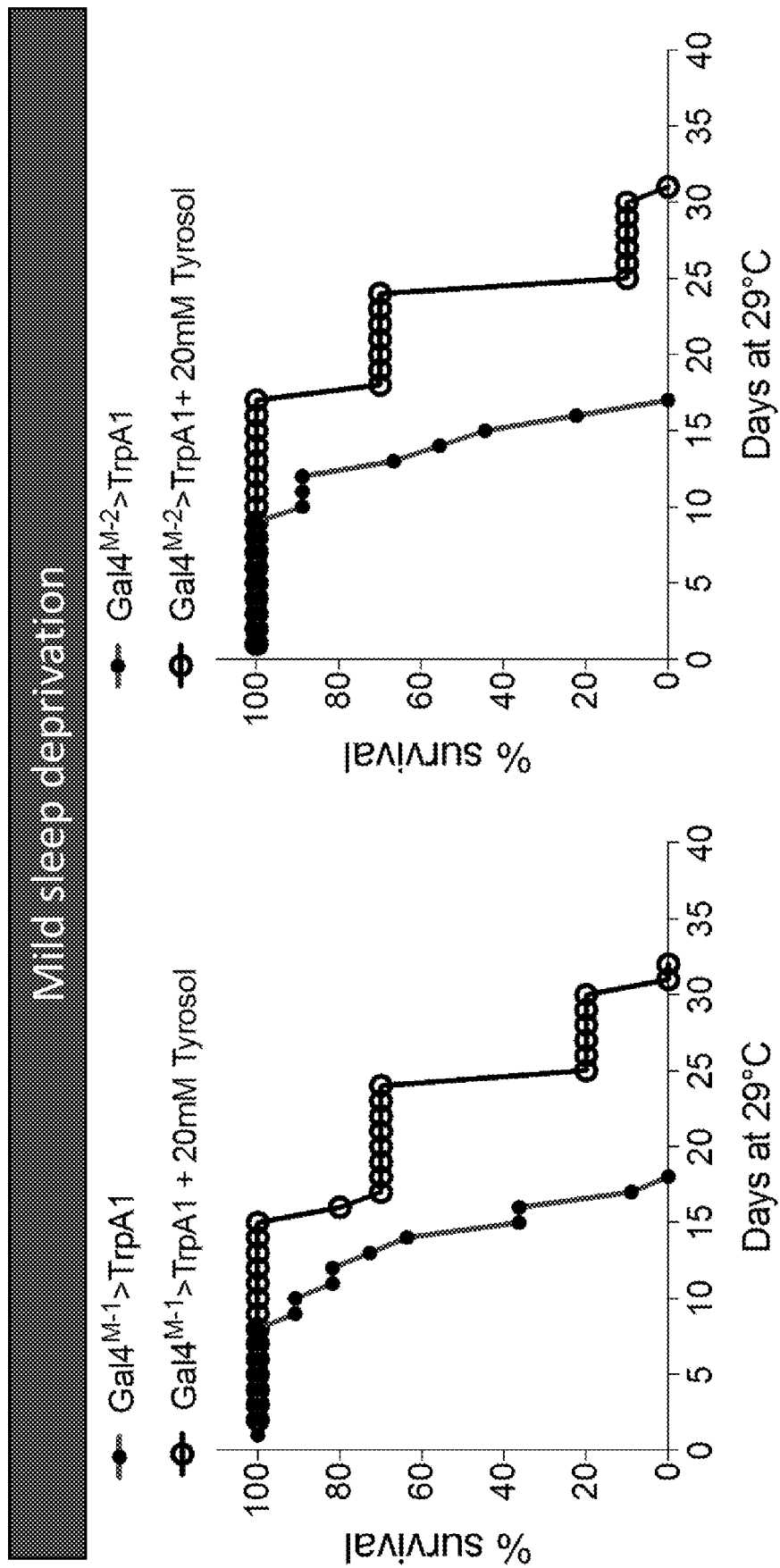
FIG. 26 shows the survival of a mildly sleep deprived animal following administering Tyrosol.
Figure 27:
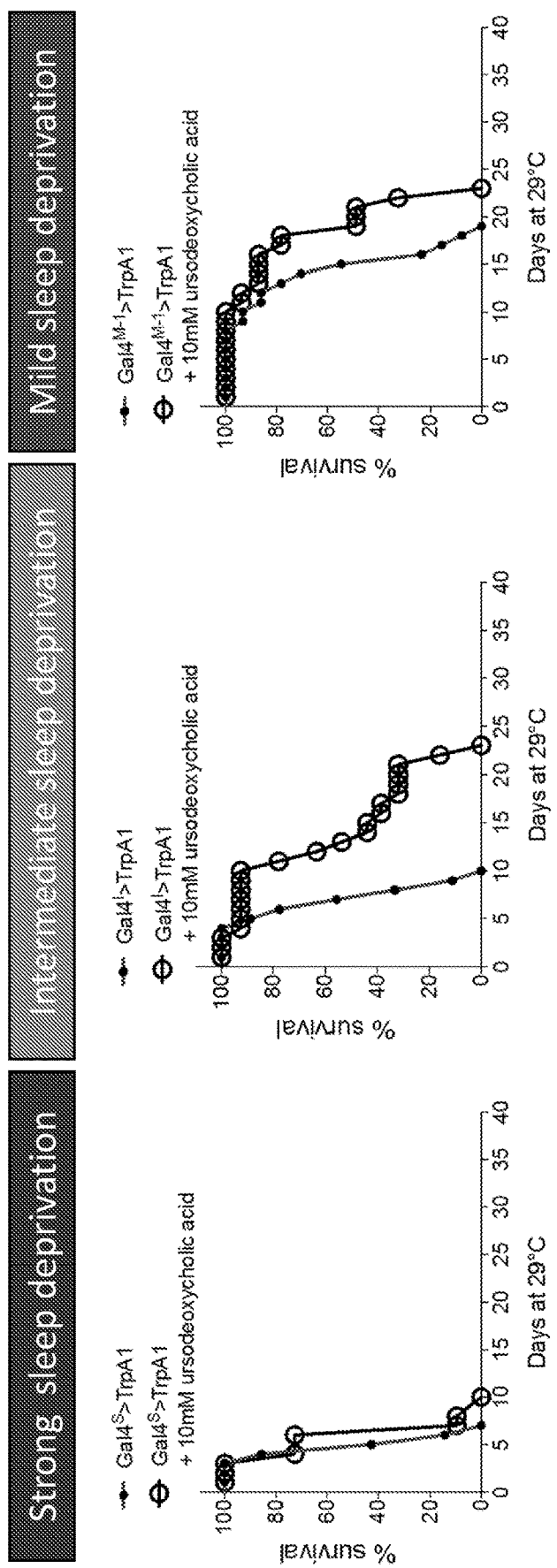
FIG. 27 shows the survival of a strongly sleep deprived (left), an intermediately sleep deprived (middle), and mildly sleep deprived (right) animal following administering Ursodeoxycholic acid.
Figure 28:
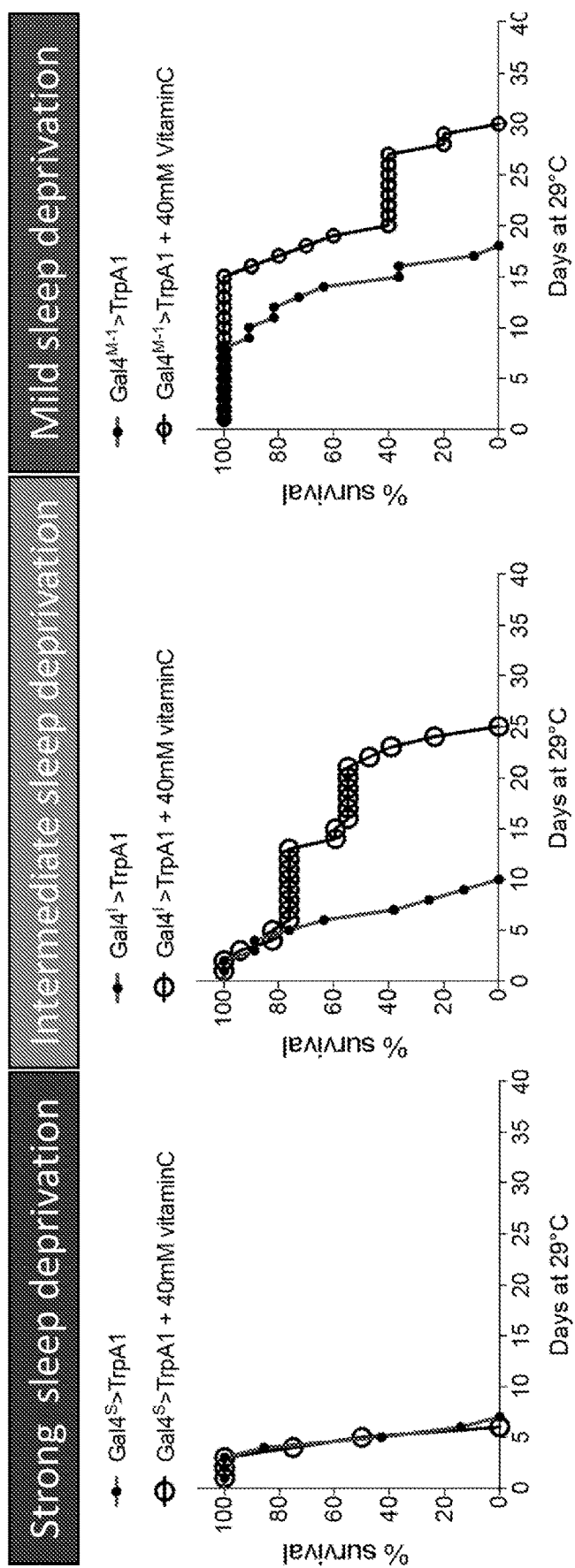
FIG. 28 shows the survival of a strongly sleep deprived (left), an intermediately sleep deprived (middle), and mildly sleep deprived (right) animal following administering Vitamin C.
Figure 29:
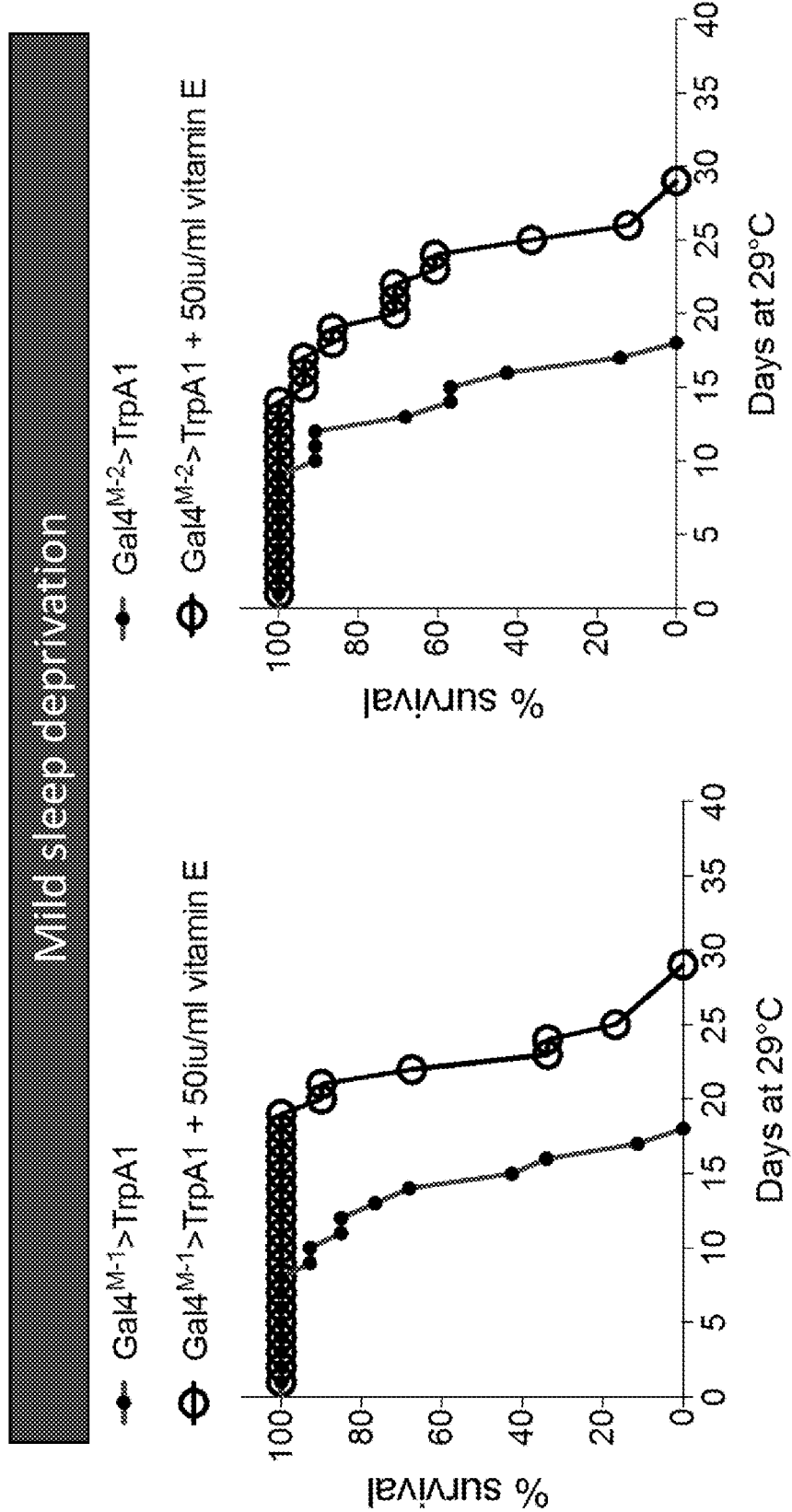
FIG. 29 shows the survival of a mildly sleep deprived animal following administering Vitamin E.
Figure 30:
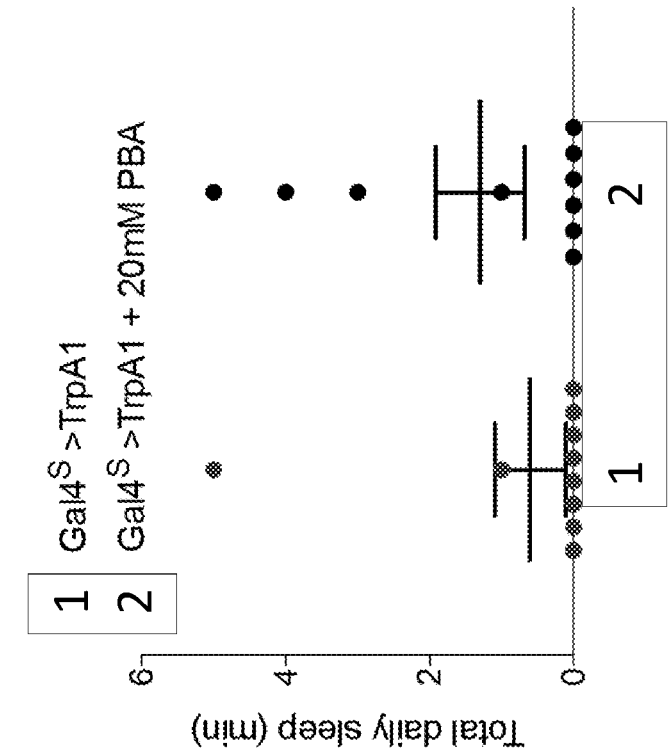
FIG. 30 shows the total sleep of animals treated with PBA.
Figure 30:
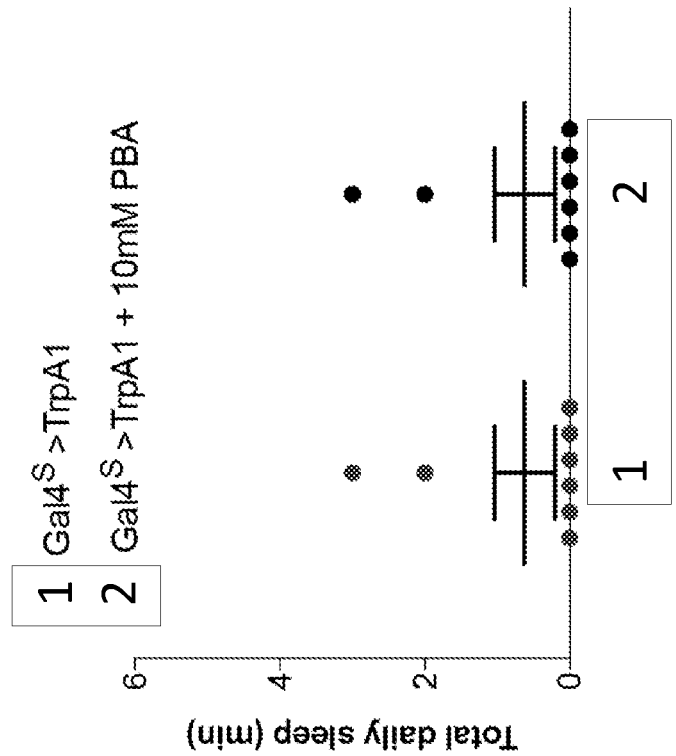
Figure 31:
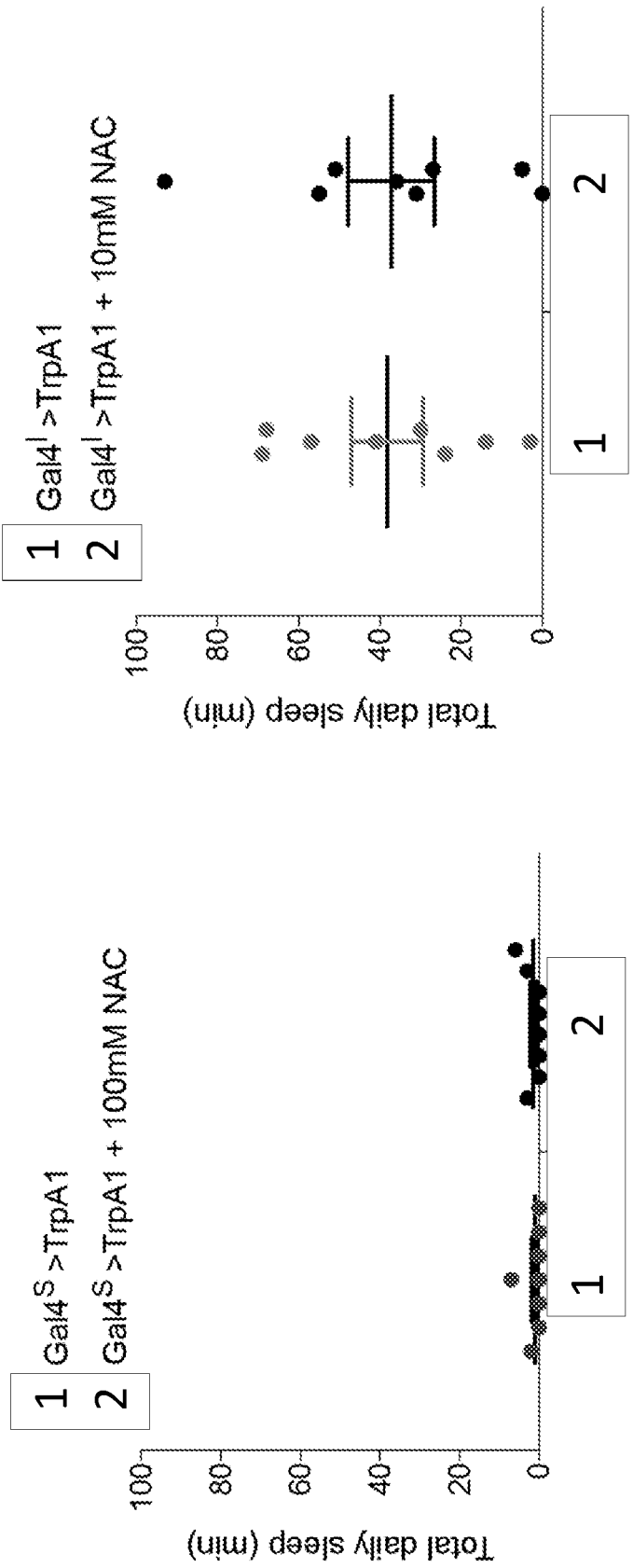
FIG. 31 shows the total sleep of animals treated with NAC.
Figure 32:
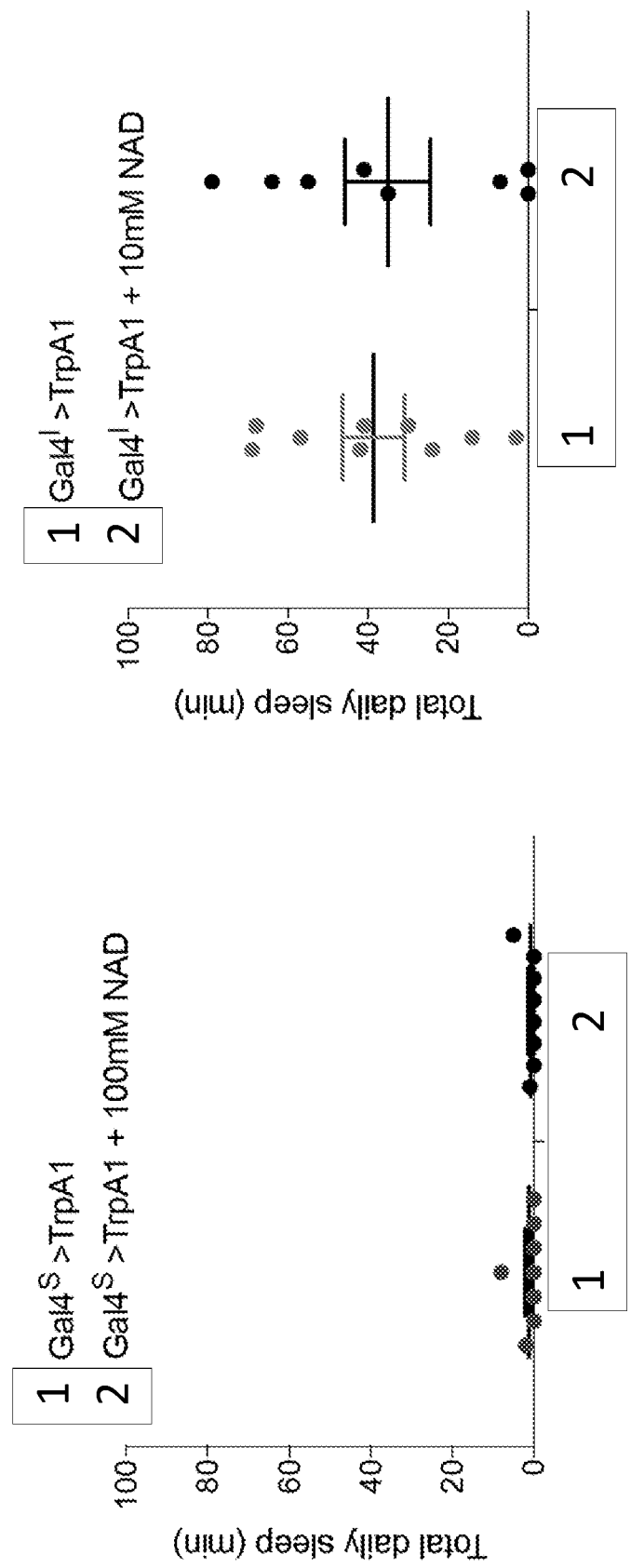
FIG. 32 shows the total sleep of animals treated with NAD.
Figure 33:
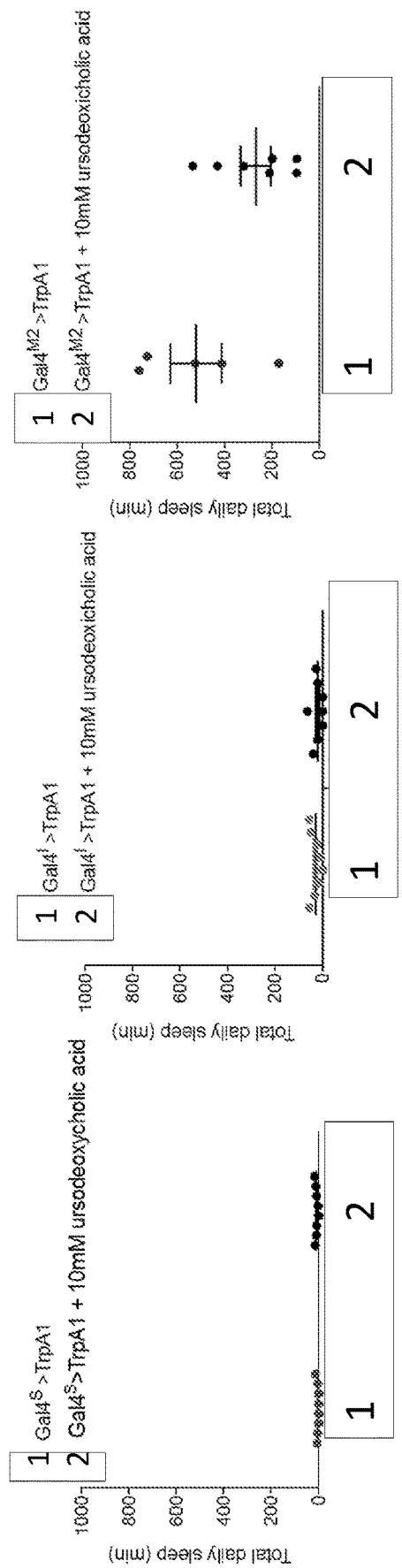
FIG. 33 shows the total sleep of animals treated with ursodeoxicholic acid.
Figure 35:
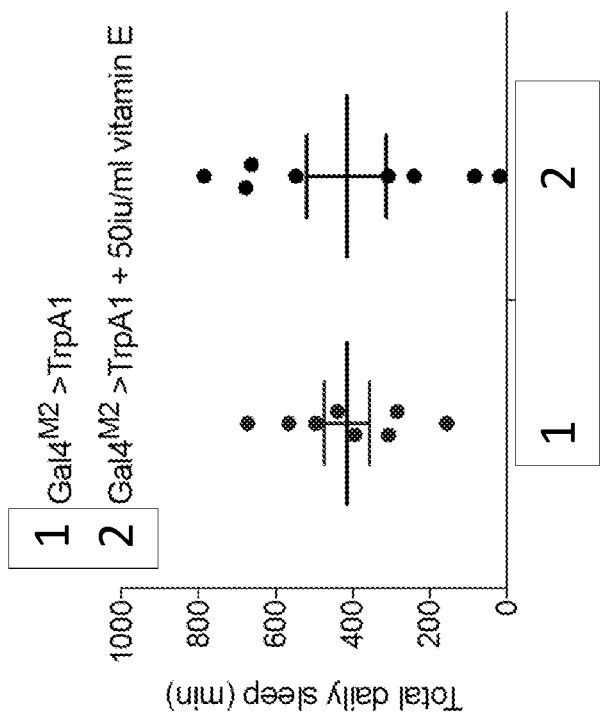
FIG. 35 shows the total sleep of animals treated with vitamin E.
Figure 34:
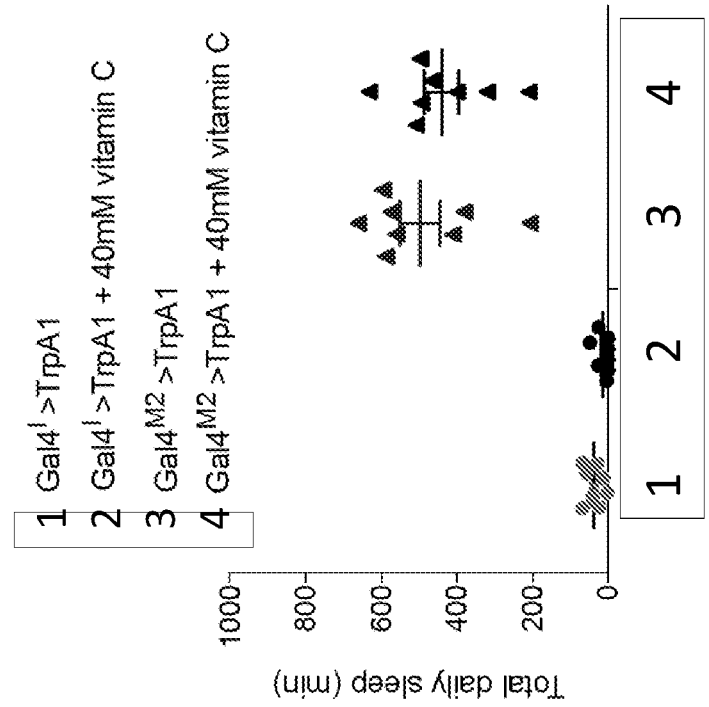
FIG. 34 shows the total sleep of animals treated with vitamin C.
Figure 36:
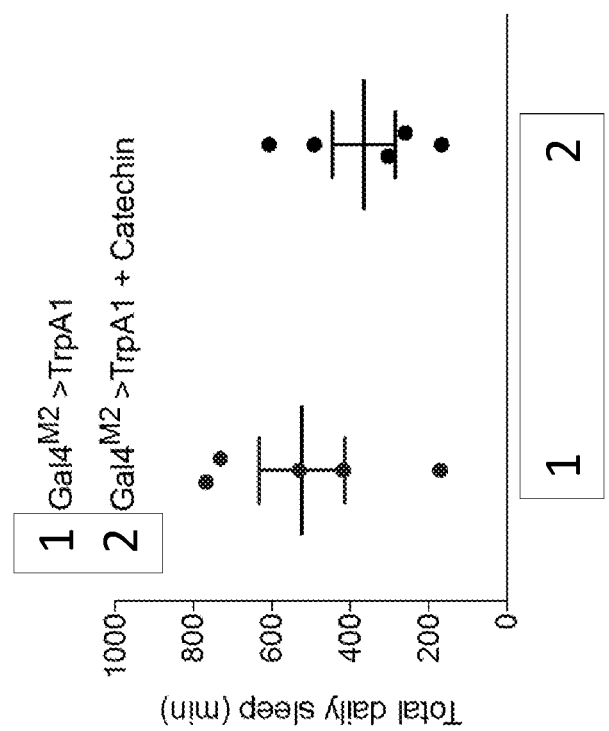
FIG. 36 shows the total sleep of animals treated with β-Carotene.
Figure 37:
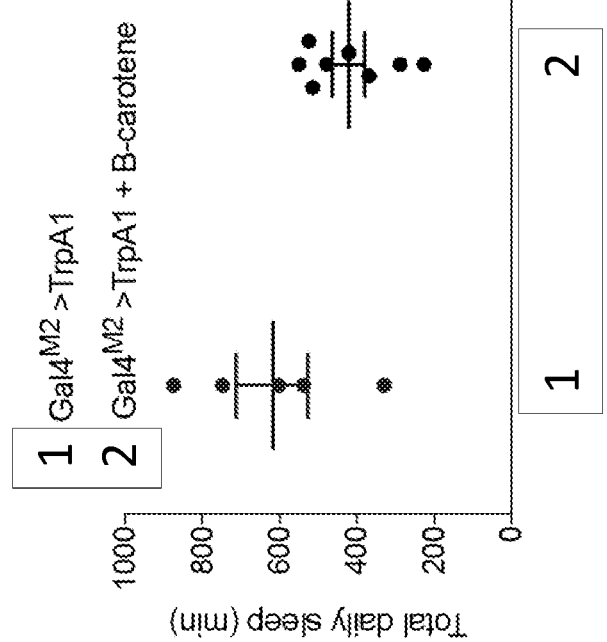
FIG. 37 shows the total sleep of animals treated with Catechin.
Figure 39:
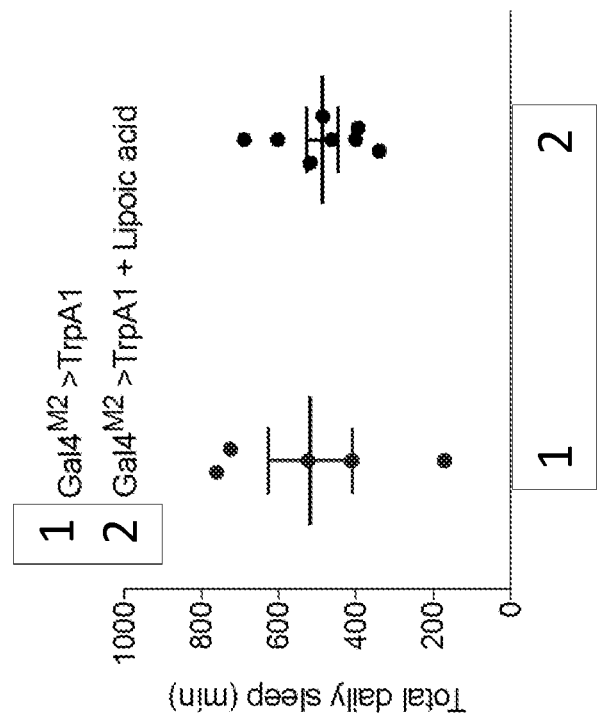
FIG. 39 shows the total sleep of animals treated with Lipoic acid.
Figure 38:
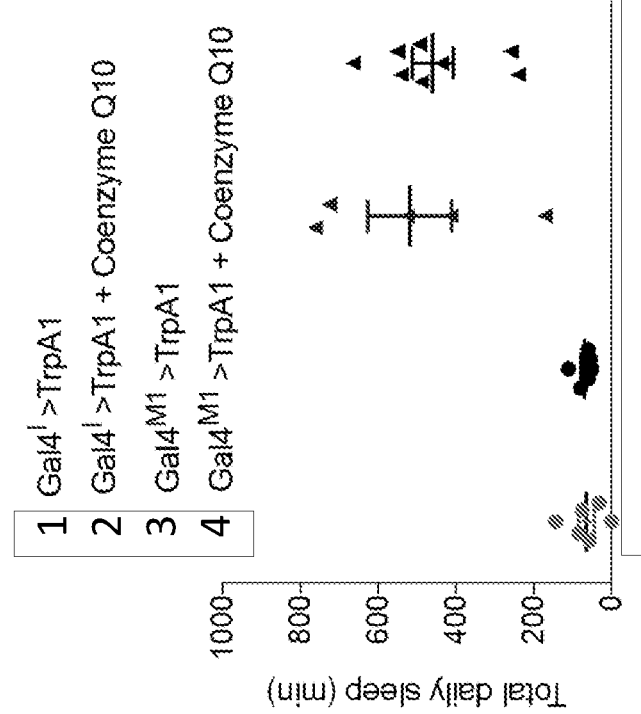
FIG. 38 shows the total sleep of animals treated with Coenzyme Q10 (ubiquinone).
Figure 41:
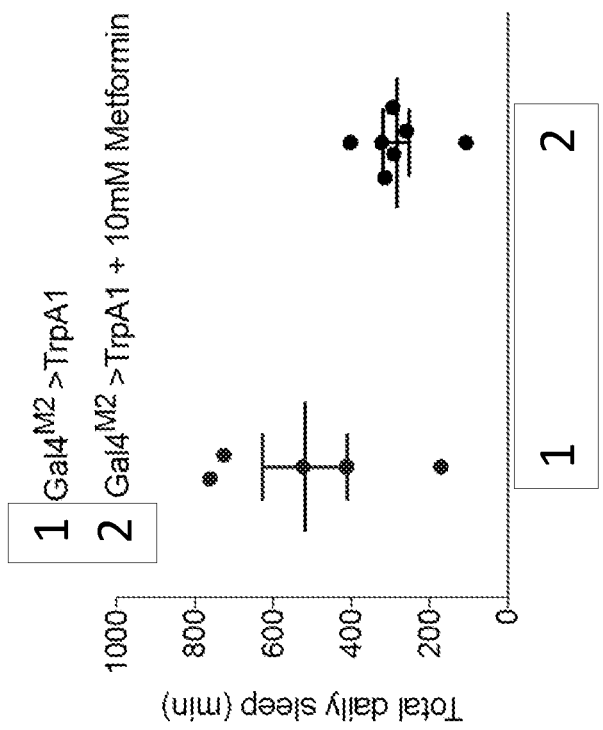
FIG. 41 shows the total sleep of animals treated with Metformin.
Figure 40:
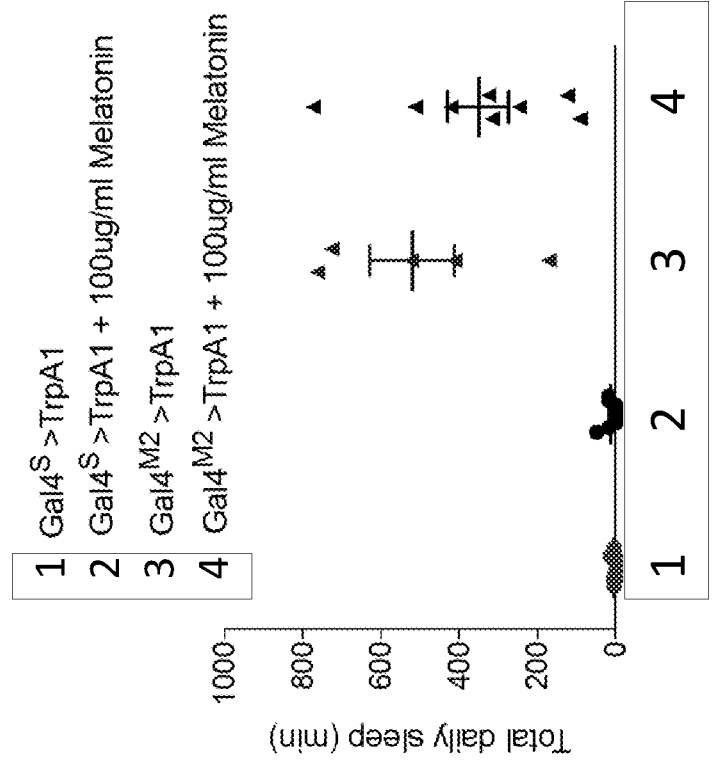
FIG. 40 shows the total sleep of animals treated with Melatonin.
Figure 42:
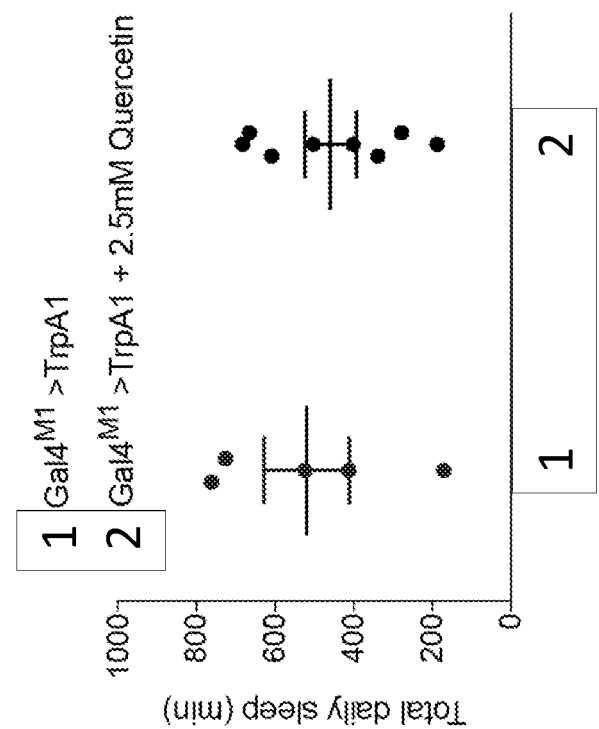
FIG. 42 shows the total sleep of animals treated with NDGA.
Figure 43:
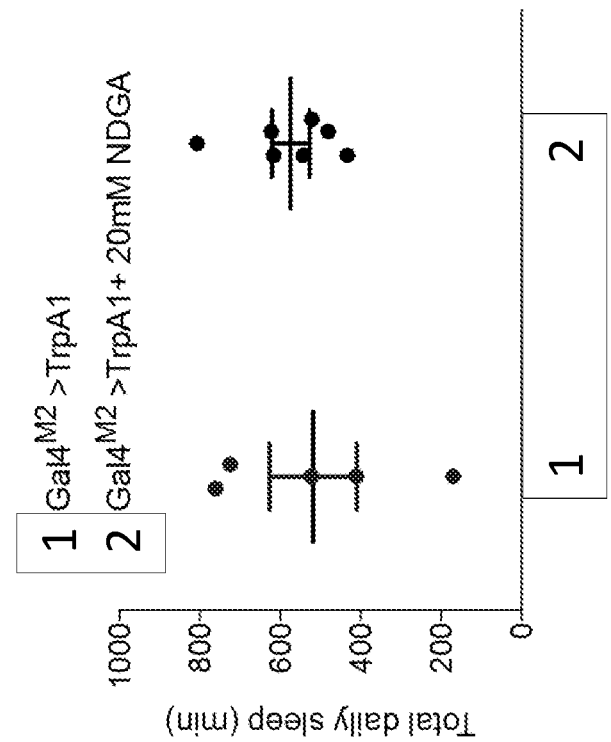
FIG. 43 shows the total sleep of animals treated with Quercetin.
Figure 44:
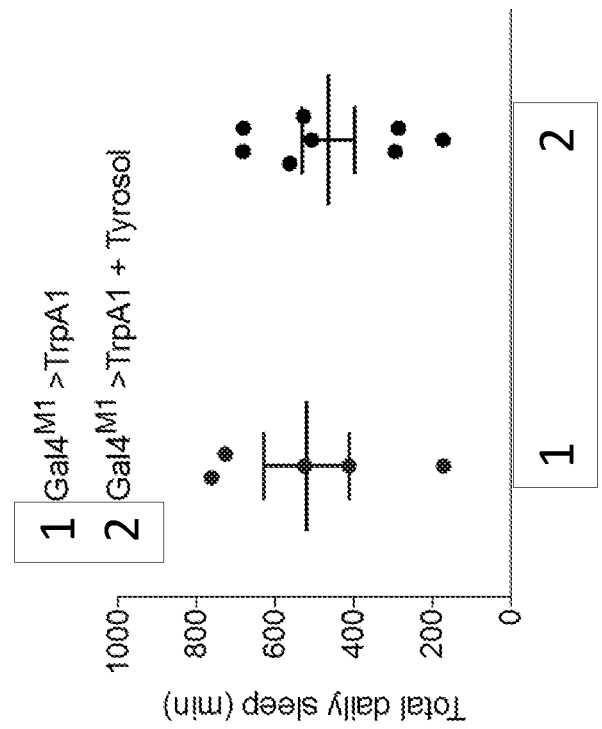
FIG. 44 shows the total sleep of animals treated with Tyrosol.
Figure 45:
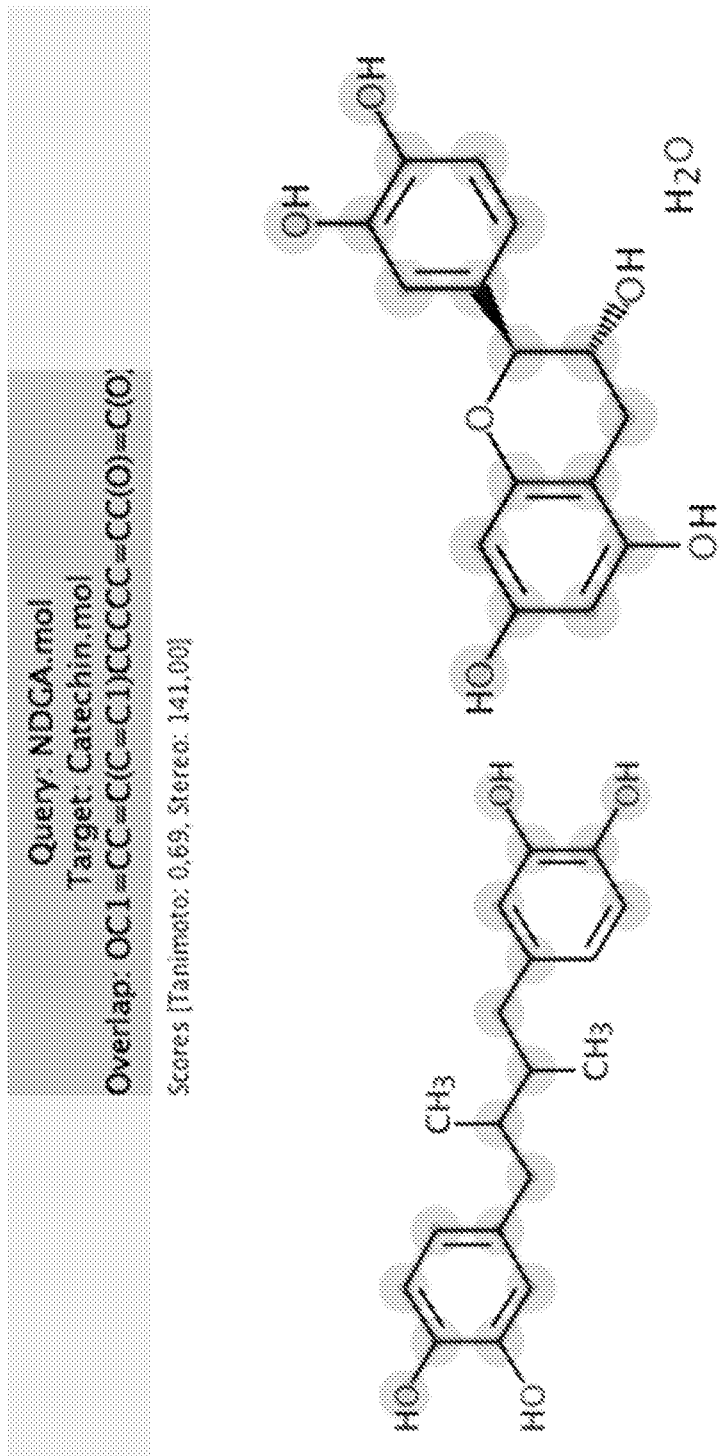
FIG. 45 shows the chemical structure comparison of NDGA and Catechin. The Tanimoto coefficient varies in the range 0.0-1.0, with a score of 1.0 indicating that the two structures are very similar (i.e. their fingerprints are the same). The stereo score denotes quality of MCS (Maximum common subgraph) score (Highest preferred), e.g., see Rahman et al., 2009.
Figure 46:
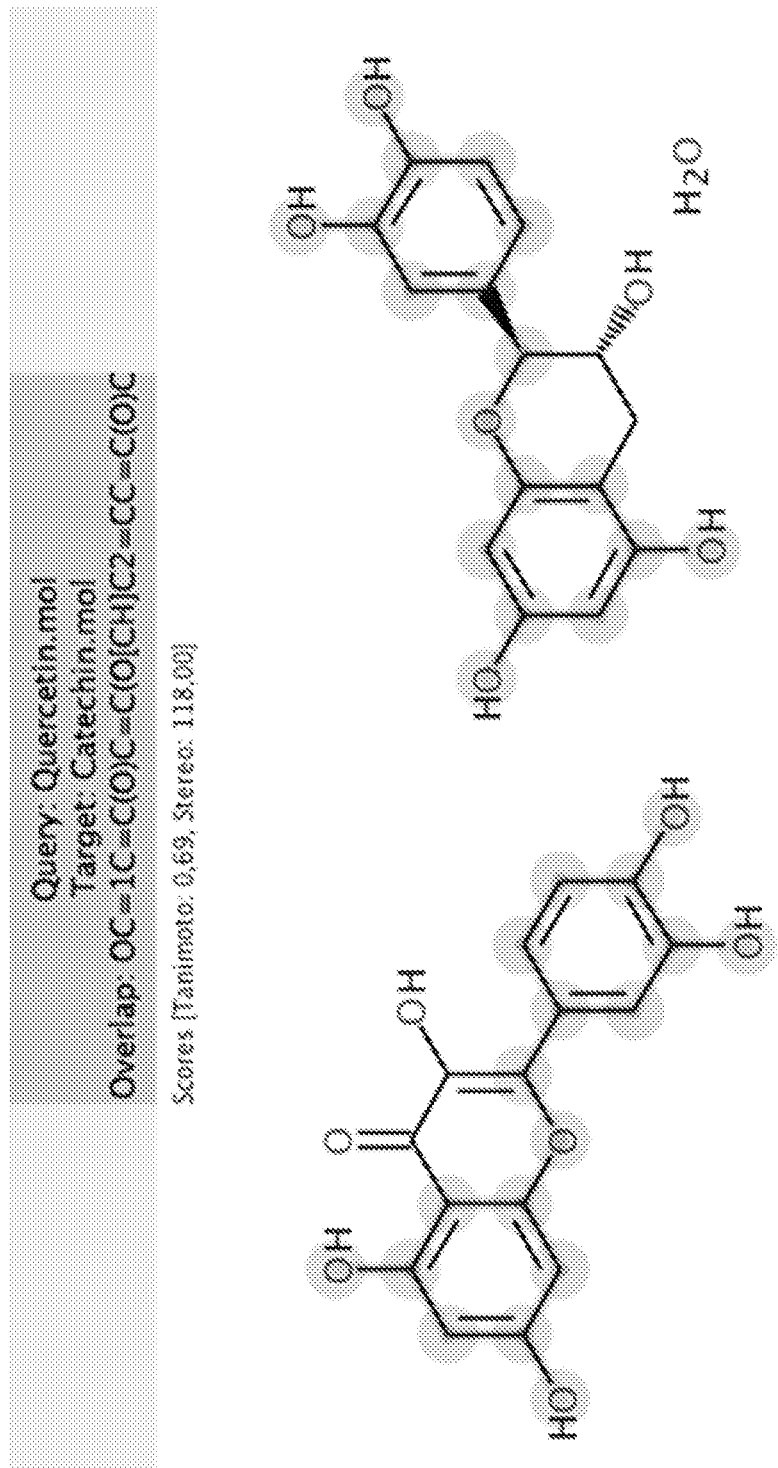
FIG. 46 shows the chemical structure comparison of Quercetin and Catechin. The Tanimoto coefficient varies in the range 0.0-1.0, with a score of 1.0 indicating that the two structures are very similar (i.e. their fingerprints are the same). The stereo score denotes quality of MCS (Maximum common subgraph) score (Highest preferred), e.g., see Rahman et al., 2009.
Figure 47:
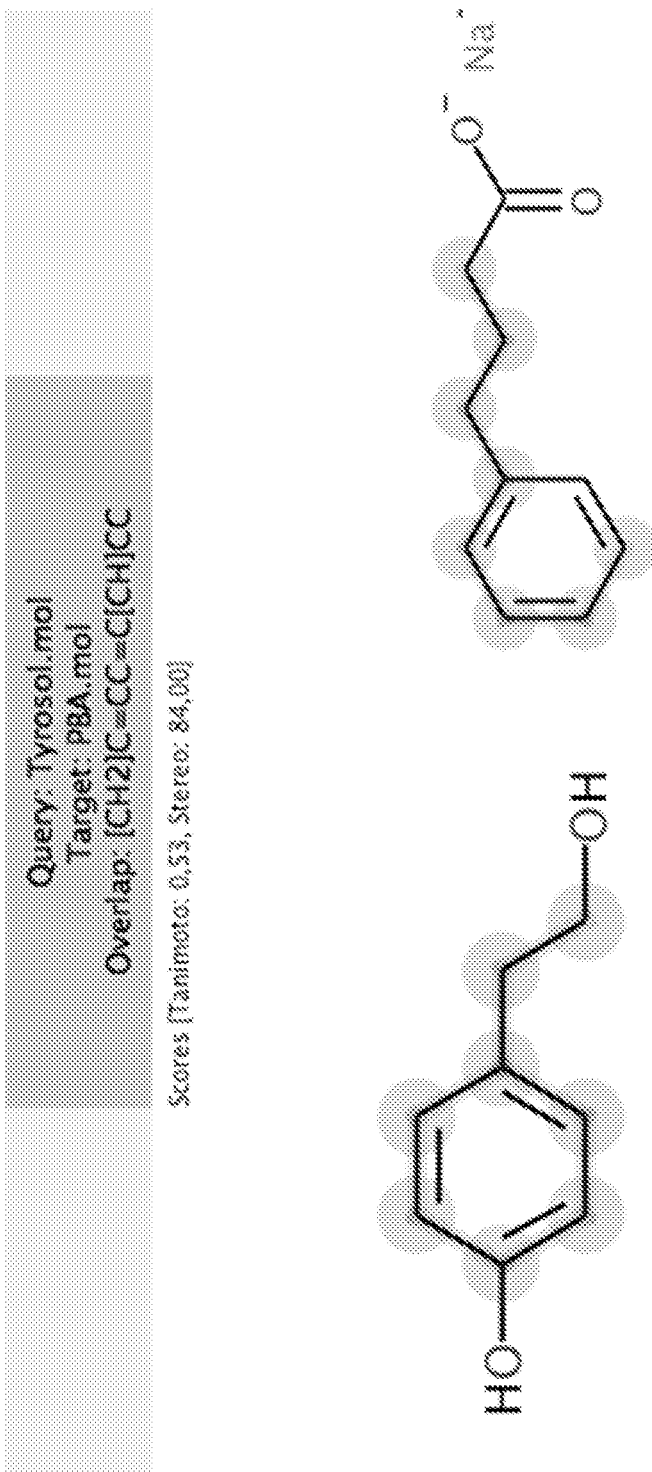
FIG. 47 shows the chemical structure comparison of Tyrosol and PBA.
Figure 48:
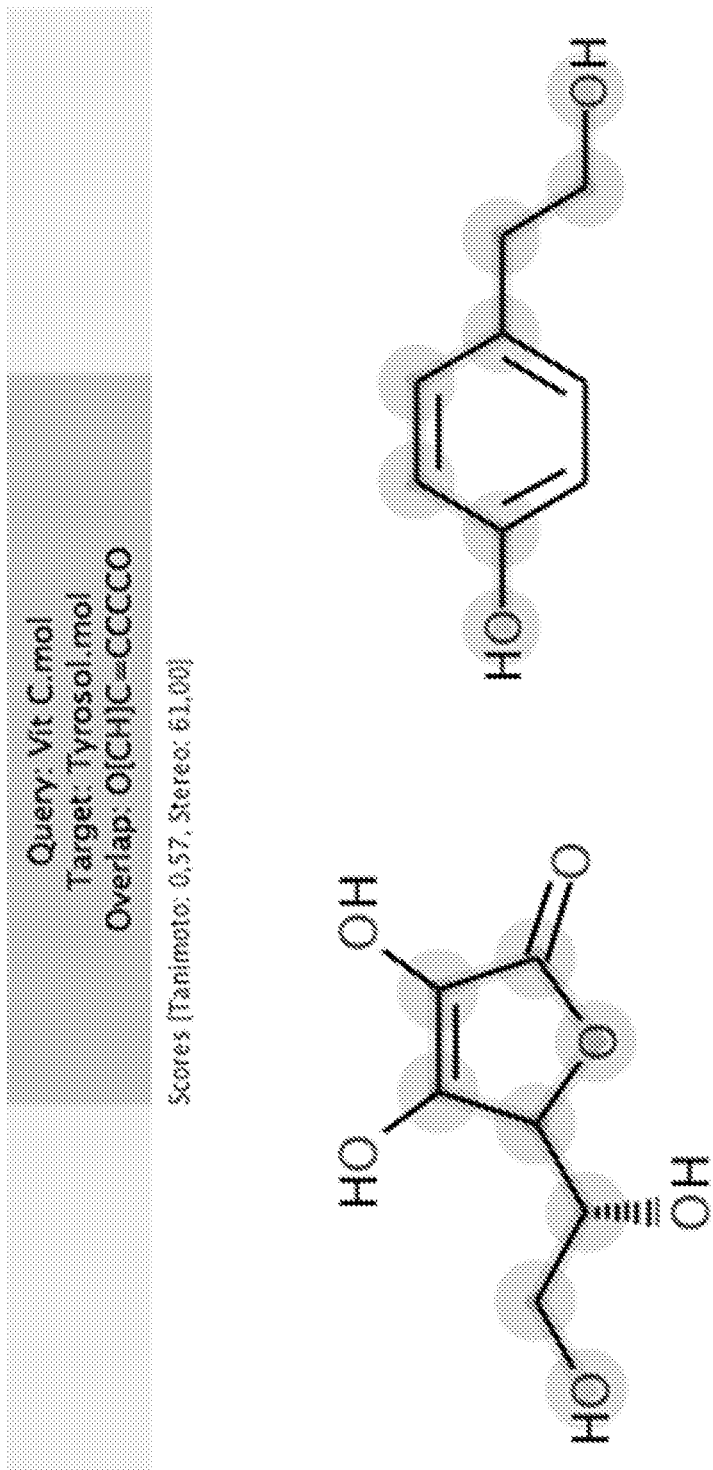
FIG. 48 shows the chemical structure comparison of vitamin C and Tyrosol.
Figure 49:
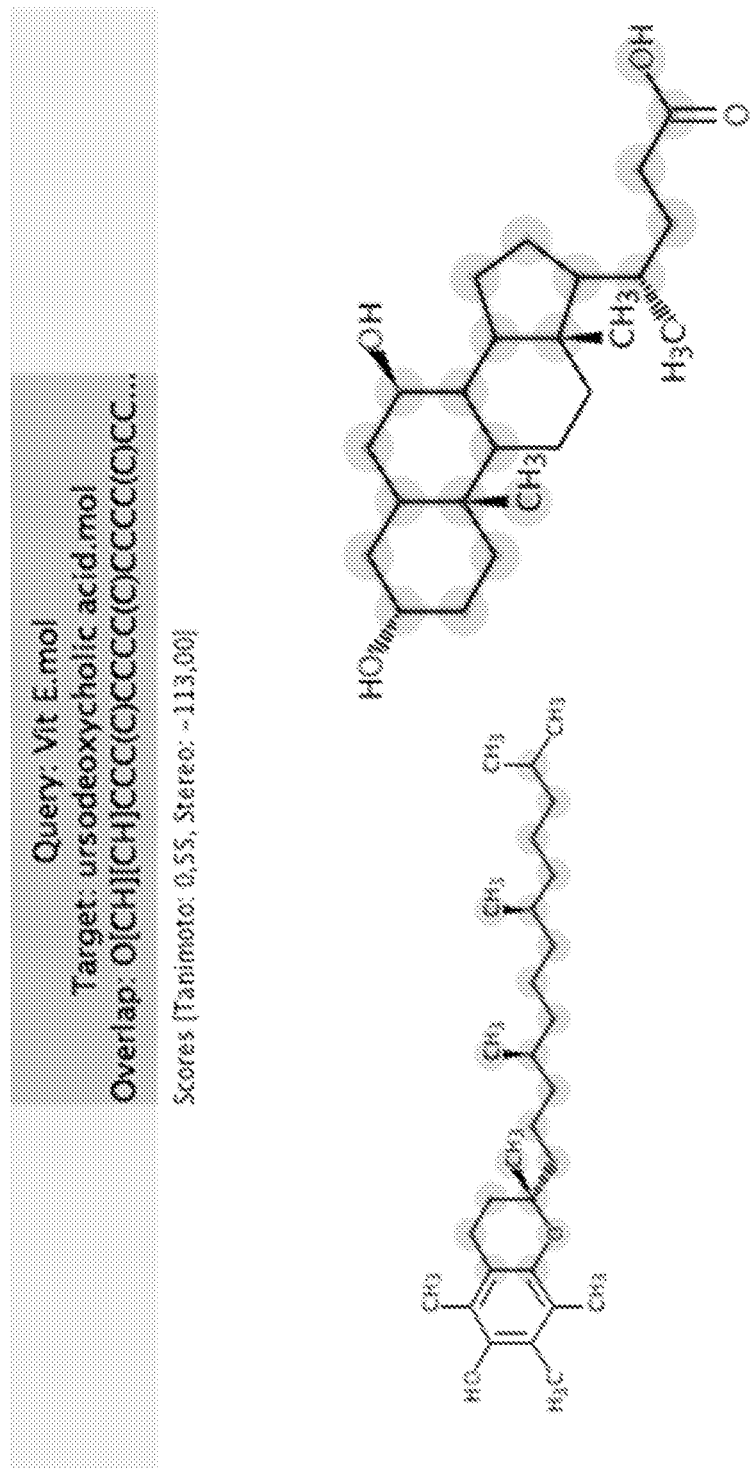
FIG. 49 shows the chemical structure comparison of vitamin E and ursodeoxycholic acid.
Figure 50:
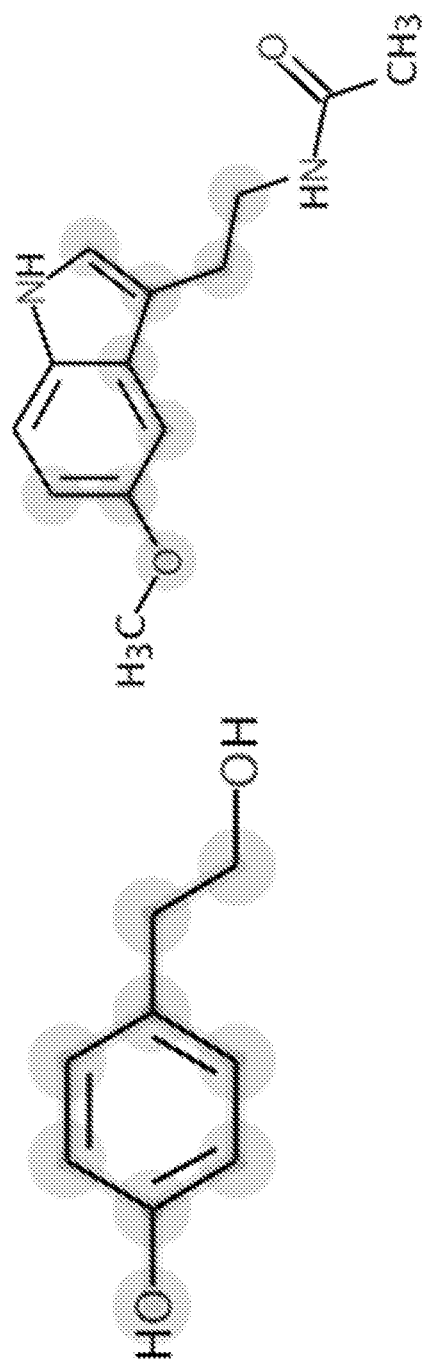
FIG. 50 shows the chemical structure comparison of Tyrosol and melatonin.
Figure 51:
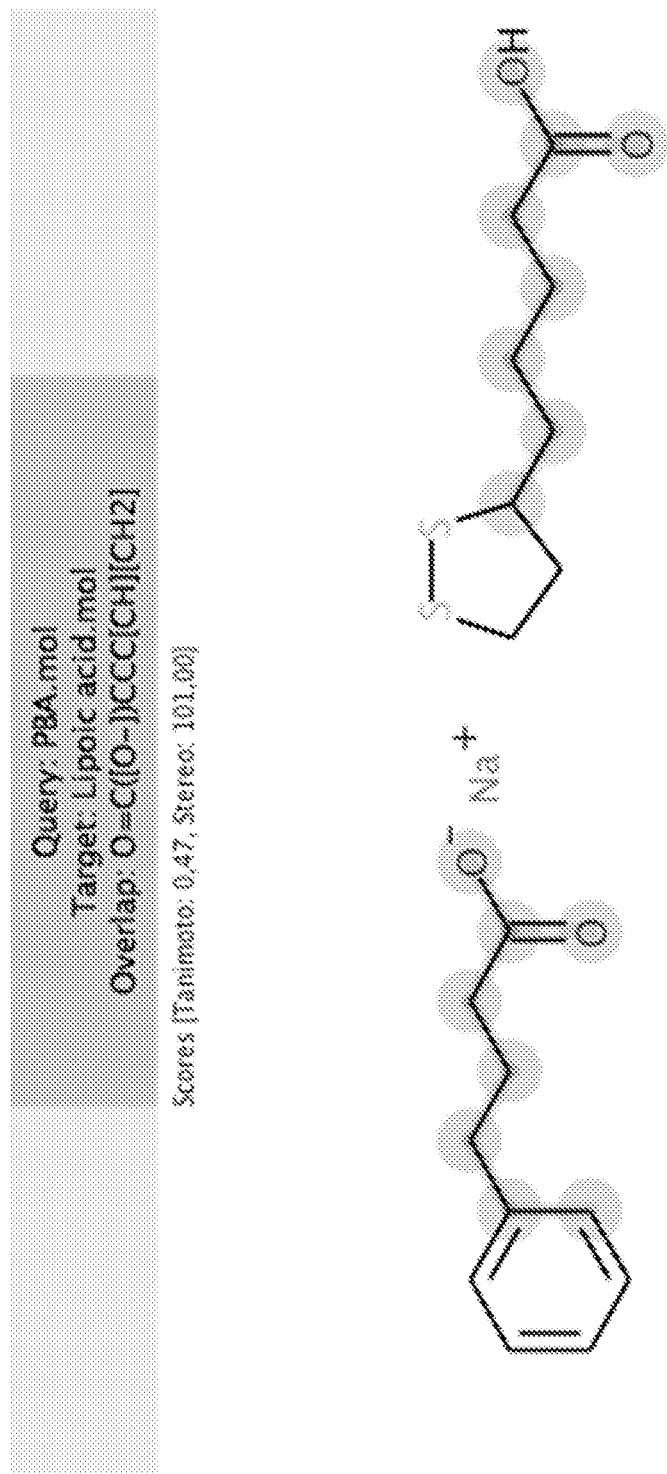
FIG. 51 shows the chemical structure comparison of PBA and Lipoic acid.
Figure 52:
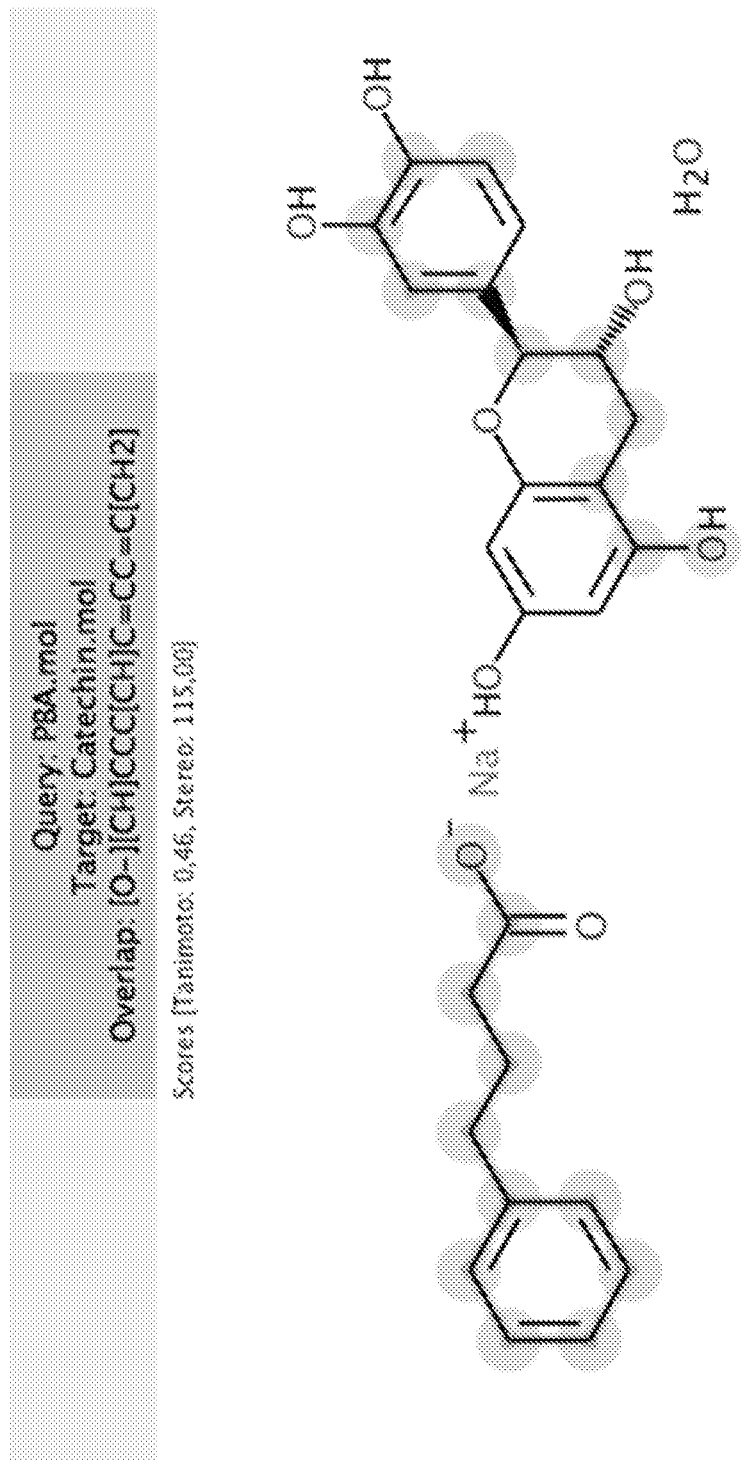
FIG. 52 shows the chemical structure comparison of PBA and Catechin.

Pathology reveals changes in the gut upon SD: The entire body was examined for signs of damage after SD, using markers of cell damage and apoptosis. Most organs examined appear normal. This includes the brain, which is in agreement with mammalian data (i.e. SD does not cause obvious brain degeneration[13]). One tissue showed a dramatic change upon SD: the gut. Dihydroethidium (DHE) staining, used to evaluate reactive oxygen species (ROS)[14], increased dramatically in the gut. To make sure this observation is not specific to SD induced with P1-Gal4 other SD-inducing Gal4 lines were tested. The change in the gut was seen in all cases, it preceded death, and its timing was correlated with the severity of the SD phenotype. For example, in the case of $Gal4^M$ line shown in FIG. 3, elevated DHE staining is detected on day 11. The possibility that the gut becomes leaky was ruled out by feeding flies blue food and showing that it remains contained in the gut. This accords with the finding that the effects of SD can be quickly reversed (see FIG. 5). In fact, when SD is stopped and flies have returned to the normal lifespan trajectory, gut DHE staining disappears (FIG. 8).

All publications cited herein expressly incorporated herein by reference in their entire tics.

REFERENCES FOR EXAMPLE 1

(1) Ancoli-Israel, S. & Roth, T. Characteristics of insomnia in the United States: results of the 1991 National Sleep Foundation Survey. I. *Sleep* 22 Suppl 2, S347-353 (1999).
(2) Becker, P. M. Insomnia: prevalence, impact, pathogenesis, differential diagnosis, and evaluation. *Psychiatr Clin North Am* 29, 855-870; abstract vii (2006).
(3) Taylor, D. J. et al. Comorbidity of chronic insomnia with medical problems. *Sleep* 30, 213-218 (2007).
(4) Thompson, C. L. et al. Short duration of sleep increases risk of colorectal adenoma. *Cancer* 117, 841-847.
(5) Hendricks, J. C. et al. Rest in *Drosophila* is a sleep-like state. *Neuron* 25, 129-138 (2000).
(6) Shaw, P. J., Cirelli, C., Greenspan, R. J. & Tononi, G. Correlates of sleep and waking in *Drosophila melanogaster*. *Science* 287, 1834-1837 (2000).
(7) Sehgal, A. & Mignot, E. Genetics of sleep and sleep disorders. *Cell* 146, 194-207, doi:10.1016/j.cell.2011.07.004 (2011).
(8) Cirelli, C. et al. Reduced sleep in *Drosophila* Shaker mutants. *Nature* 434, 1087-1092, doi:10.1038/nature03486 (2005).
(9) Koh, K. et al. Identification of SLEEPLESS, a sleep-promoting factor. *Science* 321, 372-376, doi: 10.1 126/science. 1155942 (2008).
(10) Rogulja, D. & Young, M. W. Control of sleep by cyclin A and its regulator. *Science* 335, 1617-1621, doi:10.1126/science.1212476 (2012).
(11) Hamada, F. N. et al. An internal thermal sensor controlling temperature preference in *Drosophila*. *Nature* 454, 217-220 (2008).
(12) Zhang, S. X., Rogulja, D. & Crickmore, M. A. Dopaminergic Circuitry Underlying Mating Drive. *Neuron* 91, 168-181, doi:10.1016/j.neuron.2016.05.020 (2016).
(13) Cirelli, C., Shaw, P. J., Rechtschaffen, A. & Tononi, G. No evidence of brain cell degeneration after long-term sleep deprivation in rats. *Brain research* 840, 184-193 (1999).

(14) Owusu-Ansah, E., Yavari, A., Mandal, S. & Banerjee, U. Distinct mitochondrial retrograde signals control the G1-S cell cycle checkpoint. *Nature genetics* 40, 356-361, doi:10.1038/ng.2007.50 (2008).
(15) Circu, M. L. & Aw, T. Y. Reactive oxygen species, cellular redox systems, and apoptosis. *Free radical biology & medicine* 48, 749-762, doi:10.1016/j.freeradbiomed.2009.12.022 (2010).
(16) Ramanathan, L., Gulyani, S., Nienhuis, R. & Siegel, J. M. Sleep deprivation decreases superoxide dismutase activity in rat hippocampus and brainstem. *Neuroreport* 13, 1387-1390 (2002).
(17) Roux, K. J., Kim, D. I., Raida, M. & Burke, B. A promiscuous biotin ligase fusion protein identifies proximal and interacting proteins in mammalian cells. *The Journal of cell biology* 196, 801-810, doi:10.1083/jcb.201112098 (2012).
(18) Li, X., Yu, F. & Guo, A. Sleep deprivation specifically impairs short-term olfactory memory in *Drosophila*. *Sleep* 32, 1417-1424 (2009).

Example 2

Sleep-Deprivation (SD) in Mice.

To confirm that the results presented herein in flies is conserved in higher organisms, experiments were performed to assess the level of reactive oxygen species in the brain and gut following SD in mice.

2-month-old male C57BL/6J (JAX 000664) mice were housed according to protocols approved by the Harvard University Standing Committee on Animal Care in accordance with federal guidelines. For continuous sleep deprivation, mice were placed into a restriction chamber (Pinnacle Technologies 9000-K-S) in which a rotating bar is gently kept under constant motion to limit sleep. Age-matched control, non-deprived mice were placed into a similar sized chamber but without the rotating bar. Control and sleep restricted mice were fed ad libitum and had unrestricted access to water.

To assess accumulation of reactive oxygen species, control and sleep restricted mice were sacrificed at 1, 2, and 5 days post the onset of sleep restriction and tissues (small intestine, large intestine, brain) were collected in room temperature 1× phosphate buffered saline (PBS) before embedding in O.C.T (Tissue Tek). 30 µm sections were incubated for 30 min at 37° C. with 10 µM dihydroethidium (DHE, Sigma-Aldrich) and then washed 3 times with PBS 1× for 10 min. Sections were mounted with Dapi Fluoromount-G (Southern Biotech, 0100-20) and imaged with identical intensity on a Leica SP8 confocal and/or using an Olympus VS120 slide scanner.

Figure 60A:
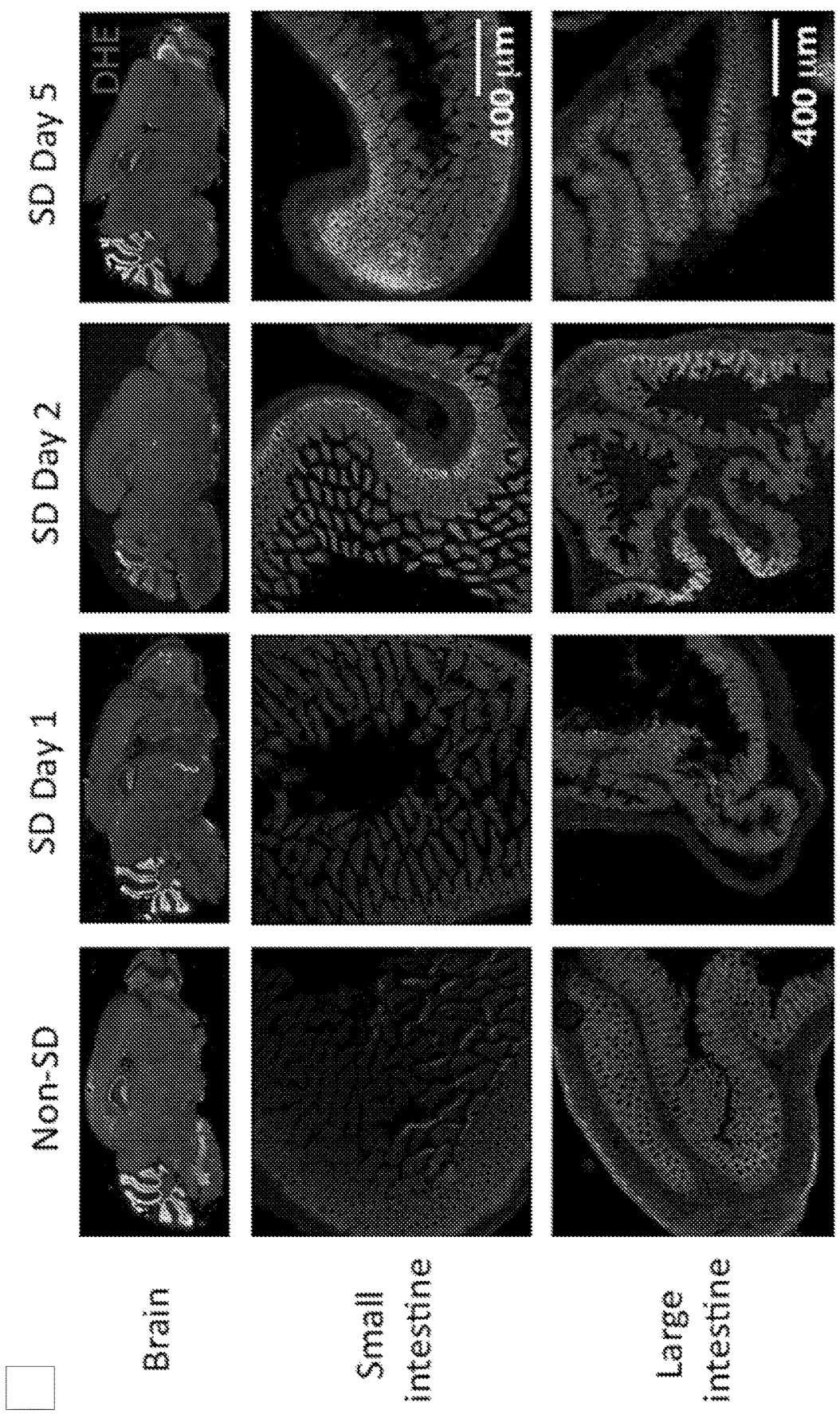
FIG. 60A-60C show the effects of sleep deprivation in mice.

Similar to observations presented herein in flies, the guts from sleep deprived mice also showed a large increase in reactive oxygen species and subsequently oxidative stress starting 2 days after sleep restriction (FIG. 60A), indicating the the findings presented herein are conserved in mammals. Moreover, consistently with data presented herein, no change in reactive oxygen species levels were detected in the brain upon sleep deprivation (FIG. 60A).

For immunostaining of tissues, samples were collected after 4 days of sleep restriction. Mice were perfused with ice-cold phosphate buffered saline followed by 4% paraformaldehyde (Ted Pella). Individual organs (brain, small intestine, large intestine) were dissected, post-fixed for 24 hours in 4% PFA followed by 20% sucrose cryoprotection before embedding in O.C.T (Tissue Tek). 30 m sections were immunostained for 48 hours with following primary antibodies: anti-53BP1, a marker of DNA damage (1:1000; Novus Biologicals); anti-Cleaved Caspase-3, a marker of apoptotic cell death (1:400; Cell Signaling Technology); and anti-TIA1, a marker of stress granules formation (1:300; Santa-Cruz, SC-166247). Sections were mounted with Dapi Fluoromount-G (Southern Biotech, 0100-20) and imaged as previously described.

Figure 53:
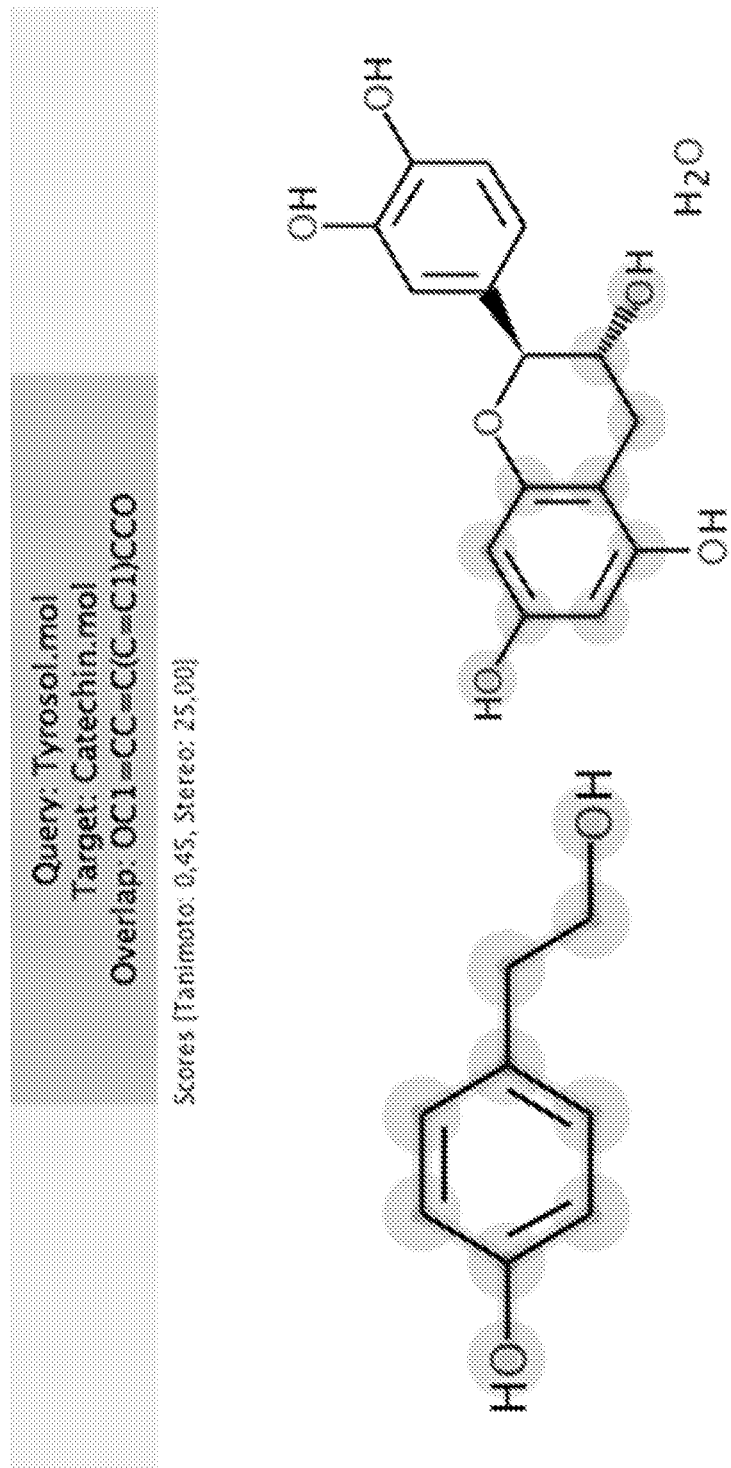
FIG. 53 shows the chemical structure comparison of Tyrosol and Catechin.
Figure 54:
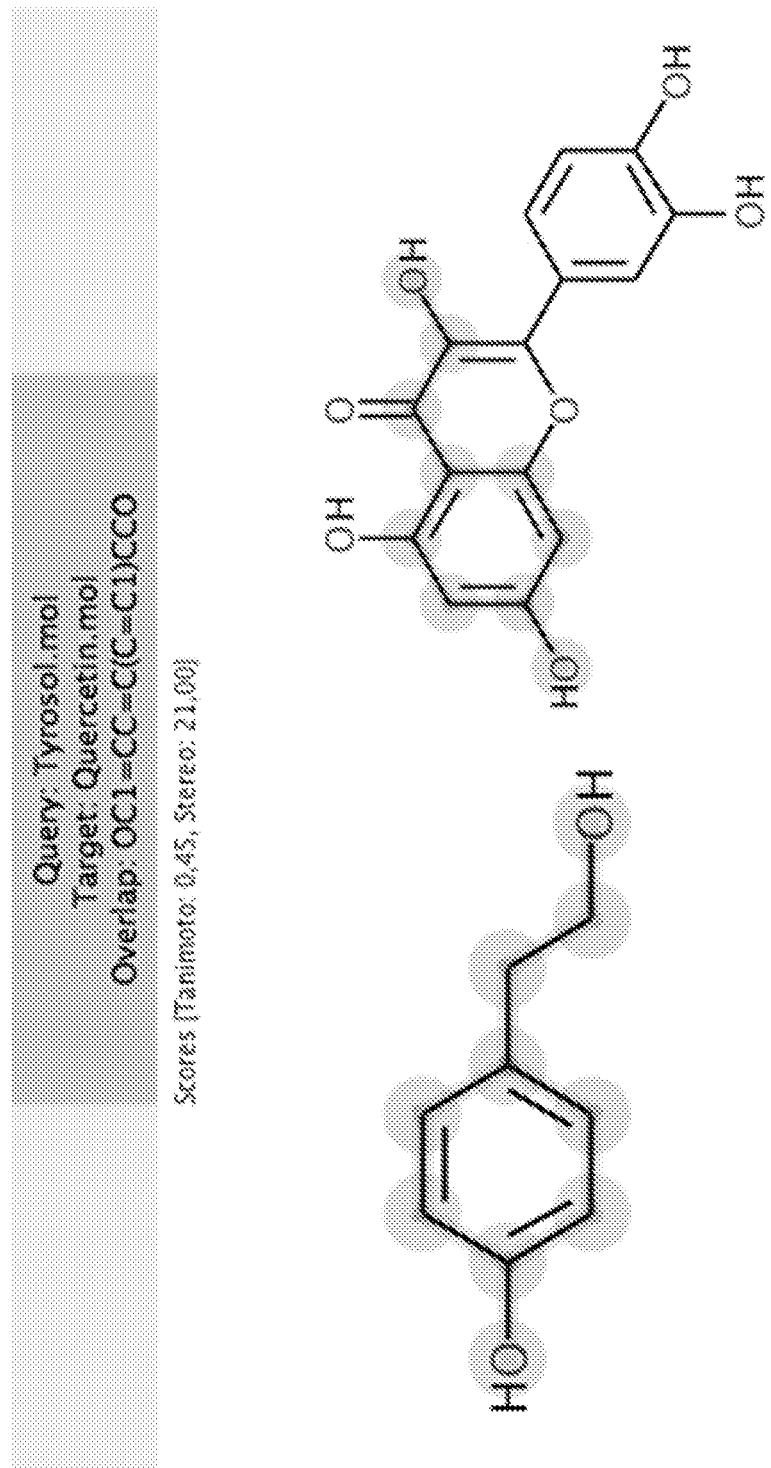
FIG. 54 shows the chemical structure comparison of Tyrosol and Quercetin.
Figure 55:
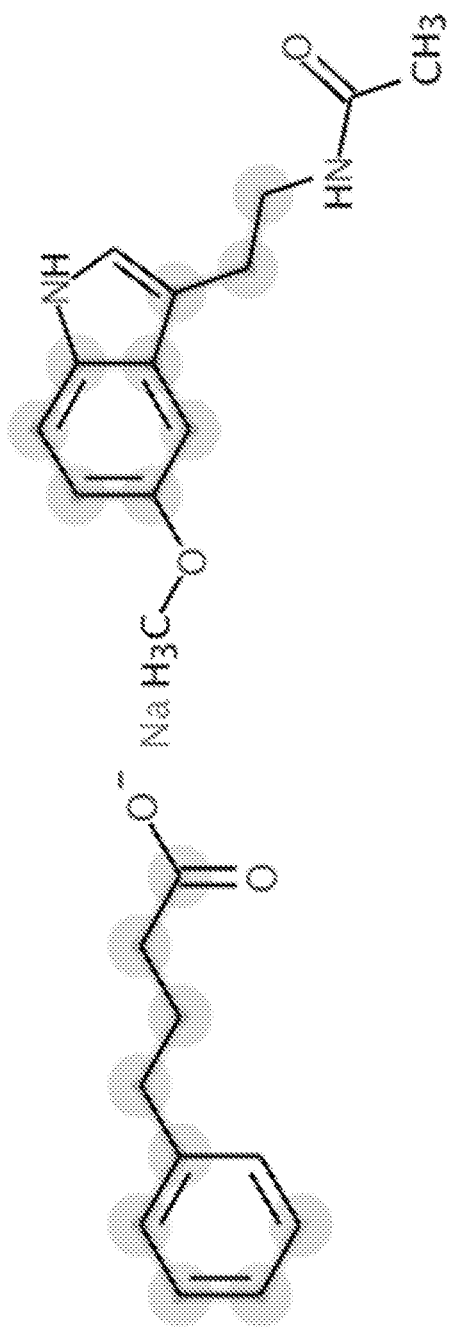
FIG. 55 shows the chemical structure comparison of PBA and melantonin.
Figure 56:
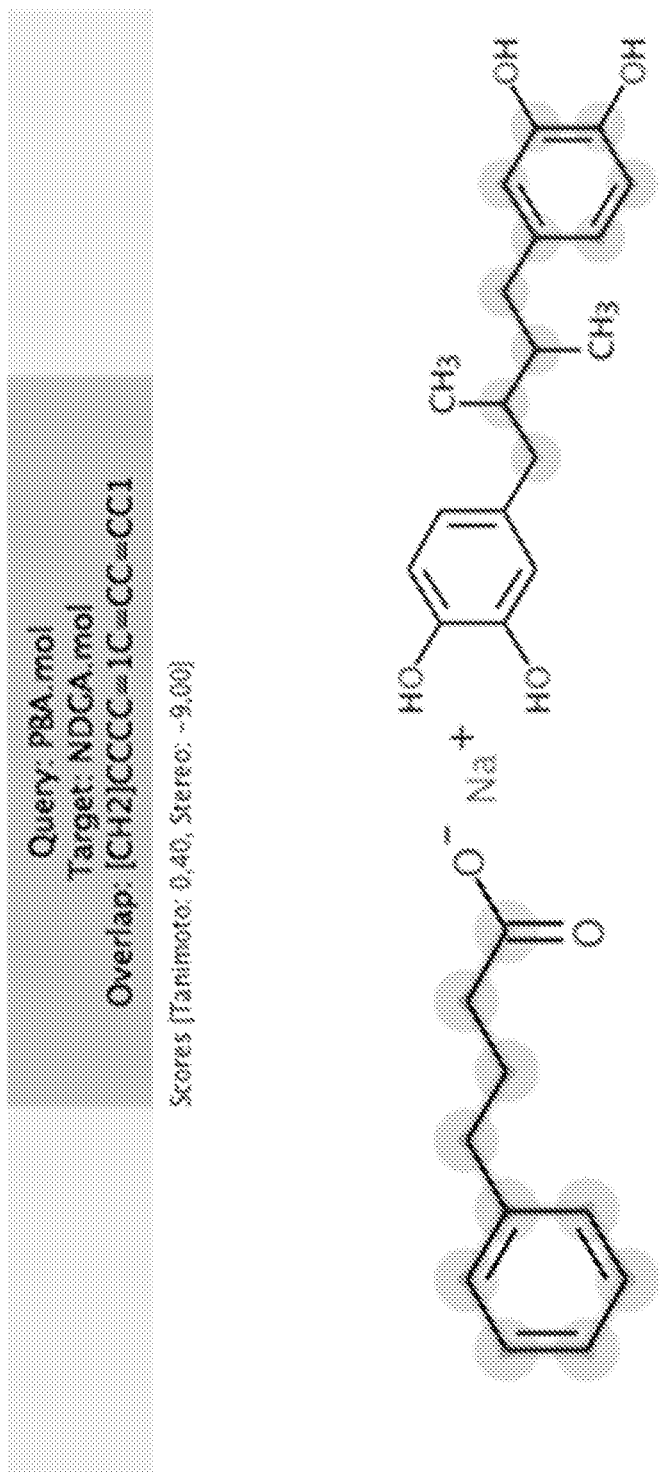
FIG. 56 shows the chemical structure comparison of PBA and NDGA.
Figure 57:
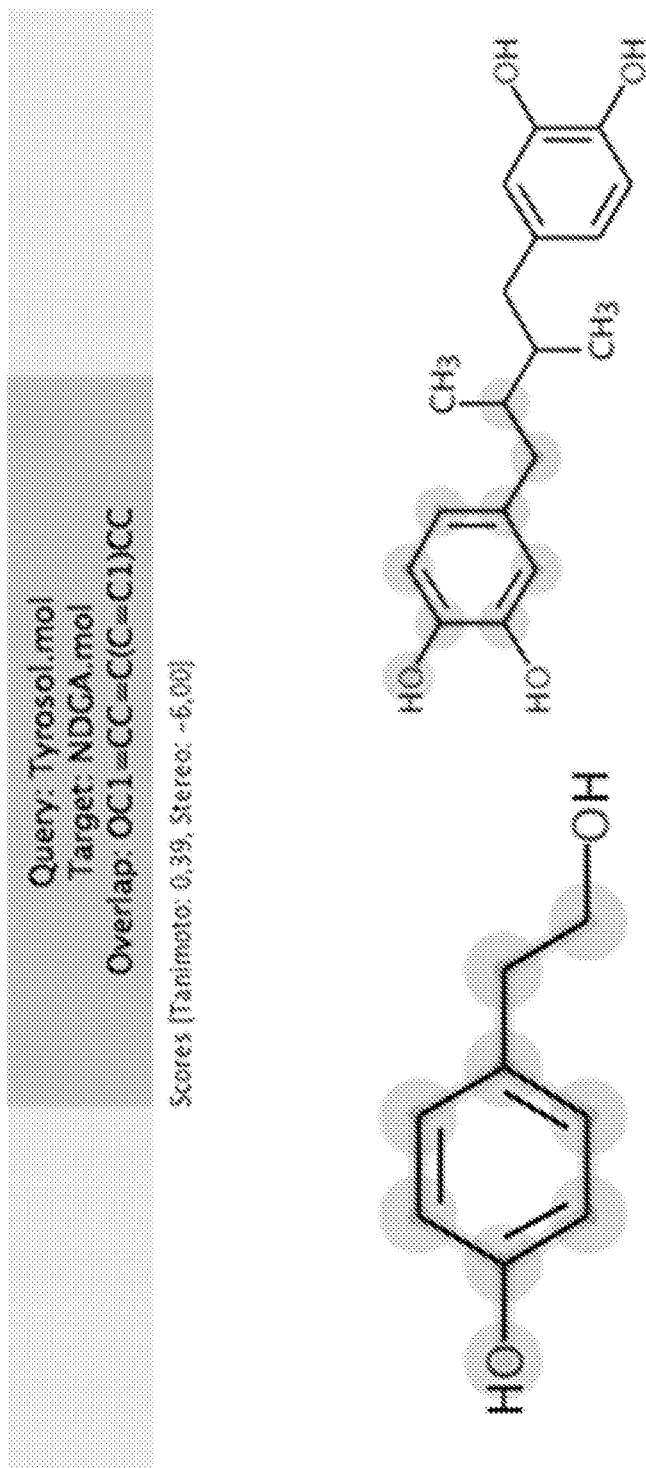
FIG. 57 shows the chemical structure comparison of Tyrosol and NDGA.
Figure 58:
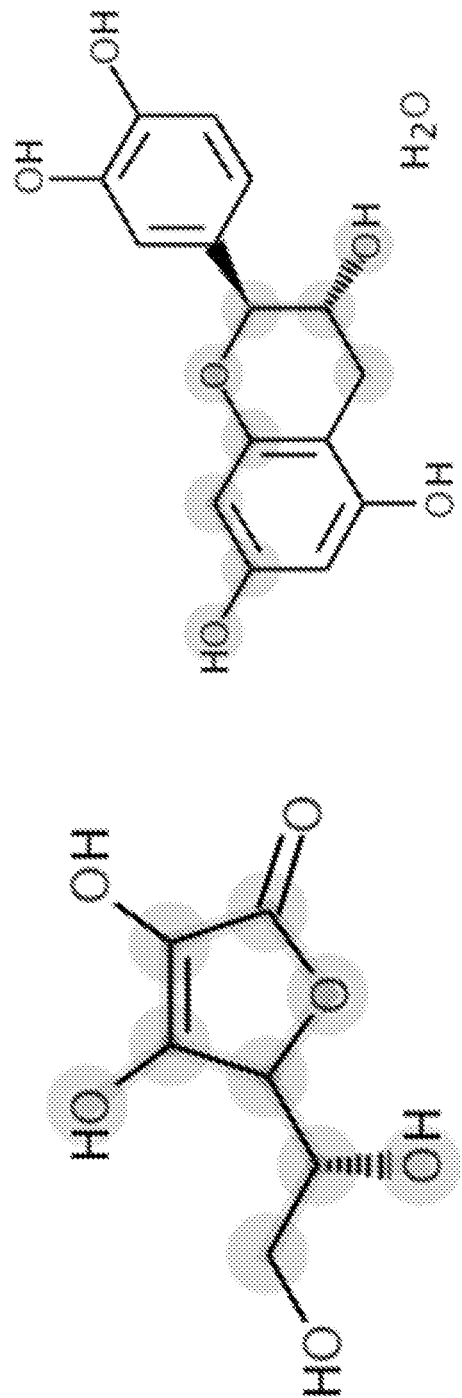
FIG. 58 shows the chemical structure comparison of vitamin C and Catechin.
Figure 59:
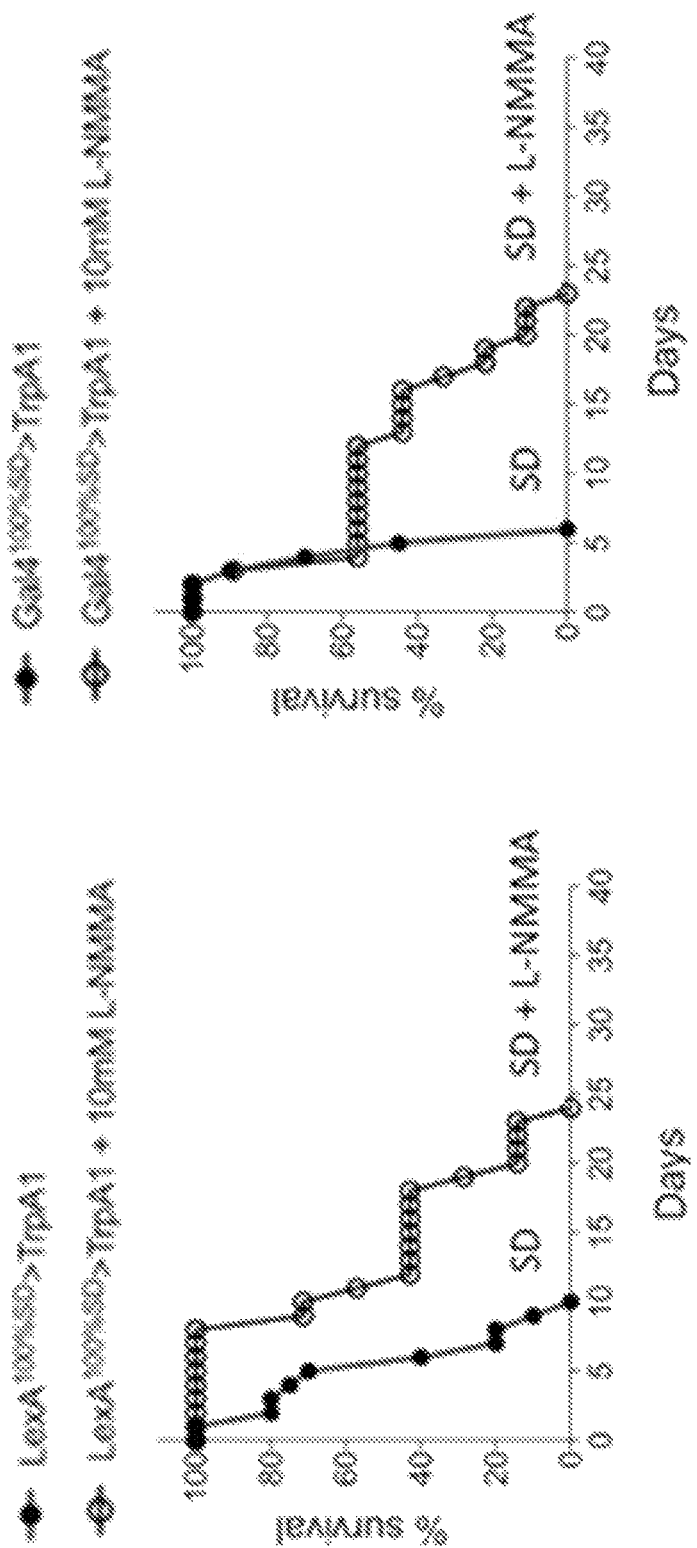
FIG. 59 shows survival following administration of L-NMMA, e.g., an inhibitor of nitric oxide synthase.
Figure 60C:
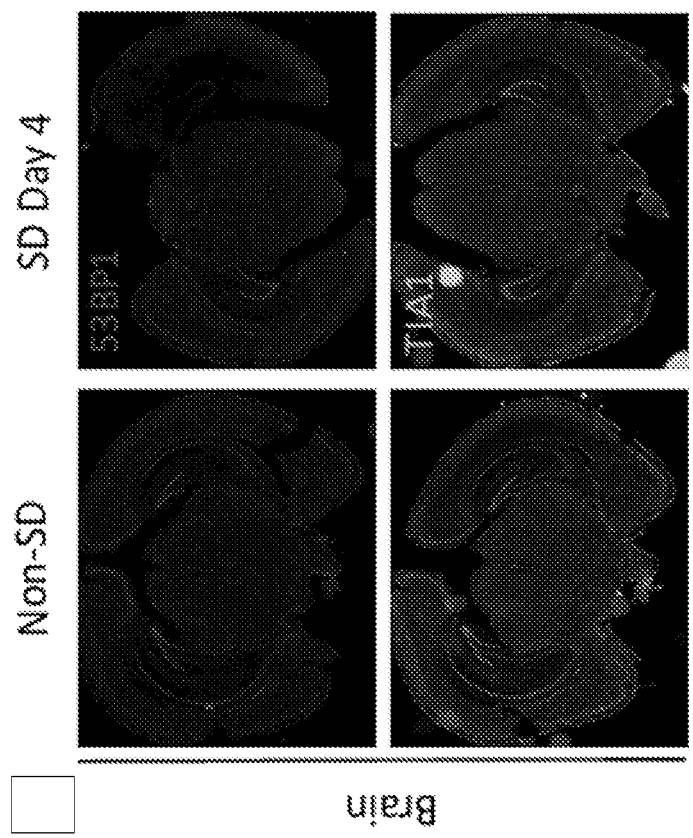
Figure 60B:
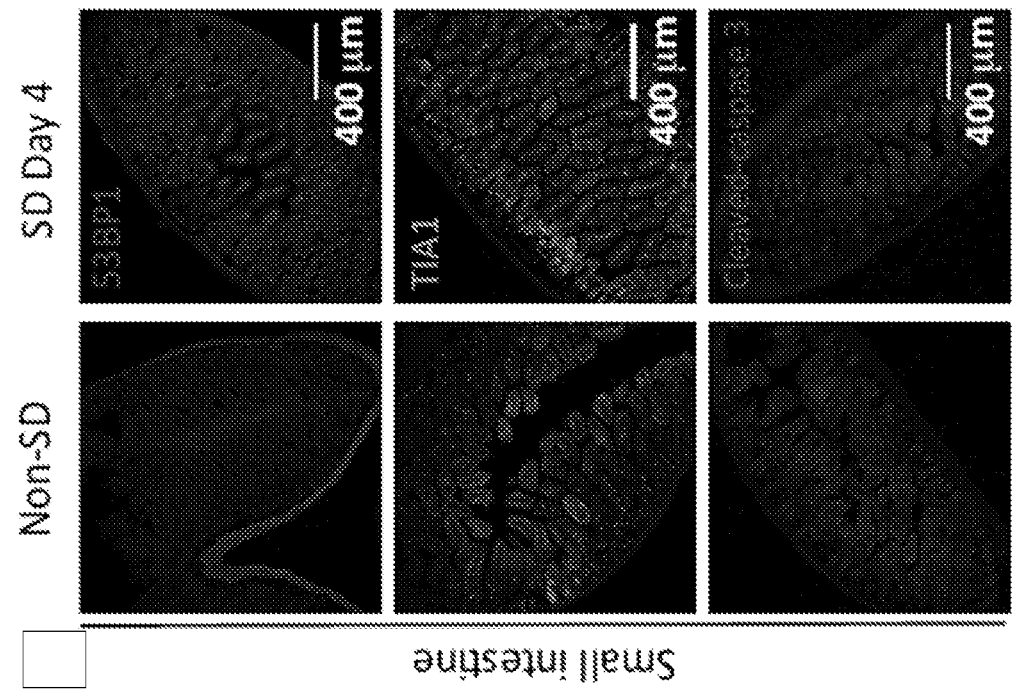
Figure 61A:
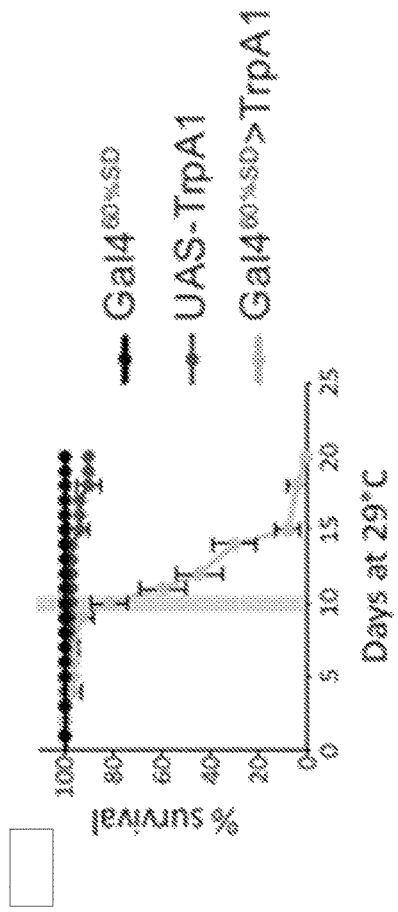
FIGS. 61A and 61B show reactive oxygen species levels after mild SD (60% SD).
Figure 61B:
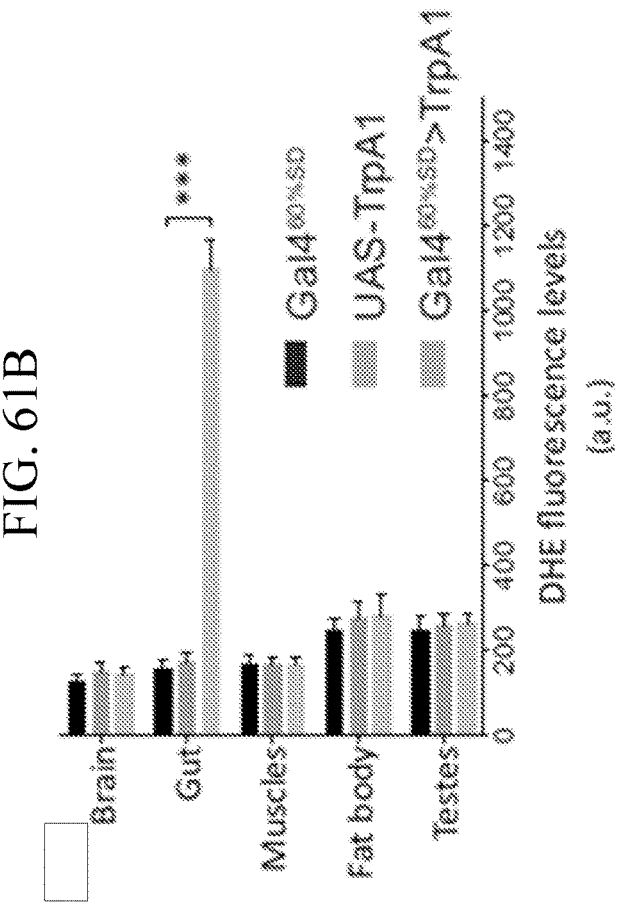
Figure 62A:
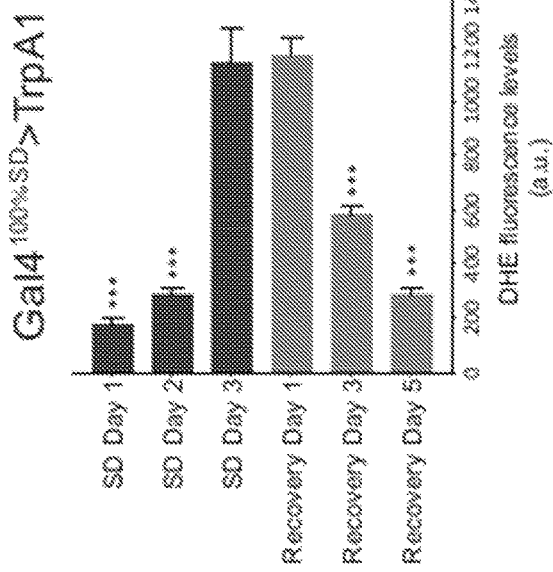
FIGS. 62A and 62B show reactive oxygen species (D.H.E. levels) with strong (100%) SD following recovery.
Figure 62B:
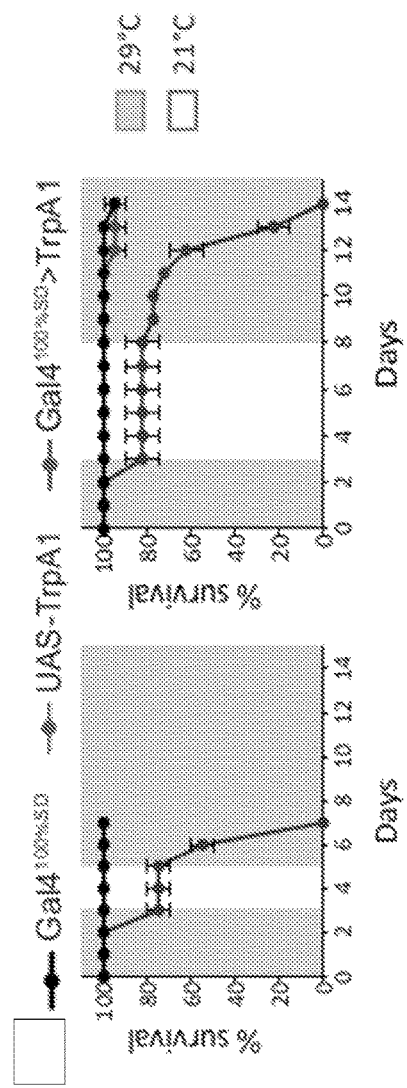

Using these markers of cell damage and cell death, increased DNA damage (FIG. 60B, 53BP1) and stress granules formation (FIG. 60B, TIA1) was observed in the guts of 4 days sleep deprived mice, however no increase in apoptois was observed at this time point. In contrast, these changes in DNA damage and stress granules were not observed in the brain at this time point (FIG. 60C).

What is claimed is:

1. A method for treating gastrointestinal tract damage induced by sleep deprivation (SD), the method comprising: administering to an individual who is sleep deprived and has gastrointestinal damage a therapeutically effective amount of a composition comprising a probiotic that reduces reactive oxygen species, wherein the probiotic is selected from the group consisting of: *Streptococcus thermophilus*, *Lactobacillus casei*, *Lactococcus lactis*, and *Lactobacillus paracasei*, or wherein the probiotic is a probiotic with a 16S rRNA sequence having at least 90% sequence identity to a 16S rRNA sequence from *Lactococcus lactis*.

2. The method of claim 1, wherein the SD is chronic or acute.

3. The method of claim 1, wherein the subject is further administered a sedative or a stimulant.

4. The method of claim 3, wherein the sedative is selected from a group consisting of: a barbiturate, a benzodiazepine, a non-benzodiazepine hypnotic, a methoaqualone, a first generation antihistamine, an antidepressant, an antipsychotics, an herbal sedative, alcohol, an opioid, a general anesthetic, a melatonin agonist, a orexin antagonists, and a skeletal muscle relaxant.

5. The method of claim 3, wherein the stimulant is selected from a group consisting of: an herbal stimulant, an amphetamine, a methamphetamine, cocaine, a methylxanthine, ephedrine, a cathinone, mephedrone, methylenedioxypyrovalerone, methylenedioxymethamphetamine, nicotine, propylhexedrine, and pseudoephedrine.

6. The method of claim 1, wherein the probiotic expresses a superoxide dismutase polypeptide.

7. The method of claim 6, wherein the superoxide dismutase polypeptide is a superoxide dismutase A (SodA) polypeptide.

8. The method of claim 1, wherein the probiotic is sensitive to lysozymes.

* * * * *